United States Patent [19]

Rausch et al.

[11] Patent Number: 5,084,558
[45] Date of Patent: Jan. 28, 1992

[54] EXTRA PURE SEMI-SYNTHETIC BLOOD SUBSTITUTE

[75] Inventors: Carl W. Rausch, Providence, R.I.; Mario Feola, Lubbock, Tex.

[73] Assignee: Biopure Corporation, Boston, Mass.

[21] Appl. No.: 119,121

[22] Filed: Nov. 10, 1987

Related U.S. Application Data

[63] Continuation-in-part of Ser. No. 107,421, Oct. 13, 1987, abandoned, which is a continuation-in-part of Ser. No. 928,345, Nov. 10, 1986, abandoned.

[51] Int. Cl.$^5$ .............................................. C07K 15/14
[52] U.S. Cl. ..................................... 530/385; 530/380; 530/384; 530/395; 530/413; 530/414; 530/415; 530/416; 530/417; 530/419
[58] Field of Search ............... 530/380, 384, 385, 395, 530/413, 414, 415, 416, 417, 419; 514/2, 8, 10, 21; 424/95, 101

[56] References Cited

U.S. PATENT DOCUMENTS

| | | | |
|---|---|---|---|
| 3,959,128 | 5/1976 | Harris | 424/101 |
| 3,991,181 | 11/1976 | Doczi | 424/101 |
| 4,001,200 | 1/1977 | Bonsen et al. | 260/112.5 R |
| 4,001,401 | 1/1977 | Bonsen et al. | 424/177 |
| 4,053,590 | 10/1977 | Bonsen et al. | 424/177 |
| 4,059,512 | 11/1977 | Harris | 424/101 |
| 4,061,736 | 12/1977 | Morris et al. | 424/177 |
| 4,061,736 | 12/1977 | Morris et al. | |
| 4,136,093 | 1/1979 | Bonhard et al. | 160/112.5 R |
| 4,314,997 | 2/1982 | Shanbrom et al. | 424/101 |
| 4,336,248 | 6/1982 | Bonhard et al. | 424/101 |
| 4,401,652 | 8/1986 | Simonds et al. | |
| 4,439,357 | 3/1984 | Bonhard et al. | 260/112 B |
| 4,473,494 | 9/1984 | Tye | 260/112 B |
| 4,526,715 | 7/1985 | Kothe et al. | 260/112 B |
| 4,529,719 | 7/1985 | Tye | 514/6 |
| 4,584,130 | 4/1986 | Bucci et al. | |
| 4,826,811 | 5/1989 | Sehgal et al. | 514/6 |

OTHER PUBLICATIONS

Issekutz, J. Immunol. Methods, 61, pp. 275–281 (1983).
Breepoel, P. M. et al., *Pflugers Arch.*, 389:219–225 (1981).
Bunn, H. F., *Science*, 172:1049–1050 (1971).
Feola, M. et al., *Surgery, Gynecology & Obstetrics*, pp. 211–221 (Mar. 1988).
Fronticelli, C. et al., *J. Biol. Chem.*, 259:10841–4 (1984).
International Drug and Device Regulatory Monitor, Appendix D, U. S. Gobt. Print. Office: 1988-20-1-874/83629 (1987).
KabiVitrum Brochure (1987).
Shanbrom, E. et al., *Endotoxins and Their Detections with Limulus Amebocyte Lysate Test*, pp. 105–113, Allan R. Liss Inc. (1982).
Nachum and Neely, "Clinical Diagnostic Usefulness of the Limulus Amoebocyte Lysate Assay", *Laboratory Medicine*, 13(2):112–117 (1982).
Pearson III and Weary, "The Limulus Amebocyte Lysate Test for Endotoxin", *BioScience*, 30(7):461–464 (1980).
Feola et al., *Surgery, Gynecology & Obstetrics*, 157:399–408, Nov. 1983.
Sofer, Gail, "Chromatographic Removal of Pyrogens", *Bio/Technology*, 1035–1038, Dec. 1984.

Primary Examiner—Esther L. Kepplinger
Assistant Examiner—Jeff Kushan
Attorney, Agent, or Firm—Hamilton, Brook, Smith & Reynolds

[57] ABSTRACT

A blood substitute and plasma expander comprising a cross-linked, substantially endotoxin-free homoglobin solution and process for preparing same. The process comprises fractionating whole blood, separating out a stromal-free, sterile hemoglobin solution, chromatographically separating endotoxins from said hemoglobin solution and crosslinking the resulting endotoxin-free hemoglobin solution.

20 Claims, 31 Drawing Sheets

EXTRA PURE SEMI-SYNTHETIC BLOOD SUBSTITUTE

CROSS-REFERENCE TO RELATED APPLICATIONS

This application is a continuation-in-part of application Ser. No. 107,421, filed Oct. 13, 1987, now abandoned, which is a continuation-in-part of application Ser. No. 928,345, filed Nov. 10, 1986 now abandoned.

FIELD OF THE INVENTION

This invention relates to a process for producing a novel semi-synthetic blood substitute and the novel semi-synthetic blood substitute resulting therefrom. The novel semi-synthetic blood substitute is a hemoglobin preparation characterized by its purity, its exceptionally low levels of endotoxin, the absence of non-hemoglobin proteins, and its molecular cross-linking profile. The semi-synthetic blood substitute has no toxic activity when used in a substitute fashion and possesses the property of reversibly binding gaseous ligands such as oxygen and is useful for transporting and supplying oxygen to vital tissues and organs. Additionally, the blood substitute serves as a blood plasma expander for management of disease and for maintaining circulatory integrity. A further aspect of the invention is the preursor or intermediate, the substantially pure, phospholipid-free, endotoxin-free hemoglobin solution in uncross-linked form.

DESCRIPTION OF BACKGROUND MATERIALS

Complex multicellular organisms are equipped with specialized tissues which are concerned with the processes of nutrition and excretion. It is the primary function of blood to provide a link between various organs and cells of the body. Blood, red cells, plasma and other components maintain a constant cellular environment by circulating through every tissue and continuously delivering nutrients to the tissues and removing waste products and various tissues which are concerned with the tissue secretions from them. PHYSIOLOGY, Third Edition, Edited by Edward E. Selkurt, Page 223 (1971). Blood is a viscous fluid composed of cells and plasma. More than 99% of the cells are red blood cells. The major function of red blood cells is to transport hemoglobin, which in turn carries oxygen from the tissues to the lungs and $CO_2$ from the tissues to the lungs. Normal red blood cells contain approximately 34 grams of hemoglobin per 100 ml of cells. Each gram of hemoglobin is capable of combining with approximately 1.33 ml of oxygen. See Guyton, A. C., BASIC HUMAN PHYSIOLOGY: NORMAL FUNCTION IN MECHANISMS OF DISEASE, Pages 84-85 (1971).

Because of the critical and ongoing need for a therapeutic agent useful as a blood substitute for carrying and supplying oxygen and as a blood plasma expander, intense research efforts have been directed to the development of an adequate blood substitute. The need for a blood substitute exists for replacing blood lost by acute hemorrhage, blood losses occuring during surgical operations, resuscitation procedures after acidental blood loss, and the like. Further, as a plasma expander, a blood substitute serves as a therapeutic to treat volume deficiency shock, as an alleviant in anaphylactic and allergic shock, and for replacing plasma lost after burns and as a result of severe diarrhea.

Hemoglobin in solution has the capabiliy to transport oxygen and, theoretically, could be used as a substitute for red blood cells. Because hemoglobin solutions are oncotically active, these solutions also expand plasma volume, thereby providing a function as a plasma expander as well. Thus the ability to be oncotically active and transport oxygen suggests that hemoglobin solutions would be desirable for a resuscitation fluid where rapid initial treatment of hypovolemia and tissue hypoxia is required. However, in order to function as an adequate resuscitation fluid, hemoglobin solutions must be capable of maintaining tissue oxygenation for specified periods of time.

Hemoglobin present in the blood of mammals has a fundamental property in solution of reversible oxygenation. In its natural form, mammalian hemoglobin is a conjugated, non-crosslinked protein having a molecular weight of approximately 68,000 and structurally comprised of two pairs of sub-units. Each sub-unit contains a heme group and a polypeptide chain, called globin. In mammals, hemoglobin is present in erythrocytes, along with stroma which consists of proteins, phospholipids and cholesterol. See CLINICAL HEMATOLOGY, By Wintrobe, 6 Ed. Pages 138-199, (1967).

The reversible binding of oxygen requires the interaction between four chains of hemoglobin (tetrameric hemoglobin) which results from the ability of the protein to exist as two different quarternary structures (relaxed and tense) that have different oxygen affinities (Perutz, M. F., *Prog. Clin. Biol. Res.* 1: 3 (1975)). The two different oxygen affinities permit hemoglobin to on-load oxygen when the oxygen tension is high (approximately 100 mm Hg p02) and to off-load oxygen when the oxygen tension is low (approximately 40 mm Hg p02) and give rise to a characteristic sigmoidal shape to the oxygen-hemoglobin dissociation curve. It is now known that the tense state of some hemoglobin in red cells is stabilized by the presence of organic phosphates such as 2,3-diphosphoglycerate (2,3-DPG), with the tense state of hemoglobin in solution not stabilized due to the absence of 2,3-DPG. Accordingly, hemoglobin in solution has a lower $P_{50}$ than hemoglobin in its natural form (Arnone, A., *Nature* 237: 146 (1972).

Aqueous hemoglobin exists in equilibrium between the tetrameric (MW 68,000) and dimeric (MW 34,000) forms (Bunn, H. F. et al., *Trans. Assn. Am. Physicians* 81: 187 (1968)). The dimers are excreted by the kidney and result in rapid intravascular elimination of hemoglobin solutions, with such solutions having a 2-4 hour plasma half-life. Accordingly, efforts have been directed to overcome the inherent limitations of hemoglobin solutions by molecular modification of the hemoglobin. The purpose of the molecular modification is to stabilize hemoglobin to prevent dimer formation and to maintain the tense conformational state. Bunn et al., supra, demonstrated that cross-linking hemoglobin reduced renal elimination and increased intravascular retention time. Bunn et al. utilized bis (Nmaleimidomethyl) ether; however, the resulting hemoglobin solution had a high oxygen affinity, i.e., a P50 of 3 mm Hg. Pyridoxal-5-phosphate has been demonstrated to have an analogous effect to 2,3-DPG in lowering oxygen affinity, resulting in a $P_{50}$ of 26-30 mm Hg (Benesch, R. E., *Biochem.* 11: 2568 (1972)). However, unlike 2,3-DPG, pyridoxal phosphate does not act as a cross-linking agent, resulting in intravascular retention times similar to that of unmodified hemoglobin (Greenburg, A. G. et al., *Surgery* 86: 13 (1979)). Thus it was thought that pyridoxylation and cross-linking would be required to produce a blood substitute having low oxygen affinities ($P_{50}$ equal to 20–30 mm Hg) and adequate intravascular retention times (half disappearance times of 20 or more hours).

In 1985, the Congress of the United States, Office of Technology Assessment (OTA), issued a report entitled "Blood Policy and Technology." At chapter 6 of this report, alternative sources of blood products were discussed, with the conclusion that the impetus to develop alternative blood sources and substitutes based on economic, safety, and availability considerations was a necessity. According to the report, the ideal red blood cell substitute would have six properties: 1) an oxygen dissociation curve and oxygen-carrying capacity similar to that of intact red blood cells; 2) be non-toxic and non-antigenic; 3) have good flow characteristics; 4) remain in the circulation for a long period of time; 5) have a long shelf life; and 6) be cost effective in comparison to present red blood cell transfusions. The report also concluded that no substitute yet developed fulfills all these criteria.

Four basic approaches have been utilized to develop an adequate blood substitute. In one approach, a class of synthetic compounds called perfluoro chemicals are being developed. In a second approach, synthesized analogues of hemoglobin are being developed. Investigators are also attempting to assemble a red cell by encapsulating hemoglobin in lipid vesicles called liposomes. Finally, purified hemoglobin has been chemically modified to prolong its circulation and enhance its oxygen binding-dissociation properties.

According to the OTA report, supra, to date, none of these approaches has proven satisfactory. The fluorocarbons are removed by the circulatory system as foreign substances, and they become lodged in the liver, spleen, and other tissues. Artificial cells made of membrane encapsulated hemoglobin have not been used for many reasons. The use of microcapsules made from synthetic polymers such as polystyrene, ethylcellulose, and silicone rubber introduces biologically incompatable materials into a living system. The cell walls of the capsules tend to leak, it is difficult to control permeability of the wall, and these capsules are too rigid and too large to pass through the capillary bed.

The use of blood and blood fractions is fraught with disadvantages. For example, the use of whole blood often is accompanied by the risk of transmission of hepatitis-producing virus and AIDS-producing virus which complicate the patient's recovery in the first instance and is fatal in the second. Additionally, the use of whole blood requires blood-typing and cross-matching to avoid immunohematological problems and inter-donor incompatibility.

The blood fraction plasma (BFP) which is a physiologically balanced colloidal solution that fulfills many of the requirements of a blood volume expander, cannot be safely used for this purpose. The high incidence and the risk of transmitting homologous serum hepatitis associated with plasma is so great, that its use is no longer warranted.

The blood component hemoglobin possesses osmotic activity and the ability to transport and exchange oxygen, but it has the disadvantage of rapid elimination from circulation by the renal route and through vascular walls, resulting in a very short, and therefore, unsatisfactory half-life.

The literature, both patent and non-patent, is replete with efforts to produce a satisfactory blood substitute from polymerized, cross-linked, stromal free hemoglobin. Bonsen et al., U.S. Pat. No. 4,001,200, and Bonsen et al., U.S. Pat. No. 4,001,401 disclose polymerized, cross-linked, "stromal-free" hemoglobin and pharmaceutical compositions (and methods for using same) comprising the polymerized, cross-linked, "stromal-free" hemoglobin. The process for producing the polymerized, cross-linked, "stromal-free" hemoglobin of Bonsen et al. comprises lysing red blood cells, filtering through diatomaceous earth to remove stroma, dialyzing to remove residual low molecular weight salts and metabolites, polymerizing to form water soluble, cross-linked, macromolecular, stromal-free hemoglobin, with a final sterilization by filtering through a filter having a pore size of about 0.20 to 0.45 microns. Included among the cross-linking agents disclosed by Bonsen et al. are dialdehydes such as glyoxal, malonic dialdehyde, succinic dialdehyde, glutaraldehyde, adipaldehyde, 3-methyl glutaraldehyde, propyladipaldehyde, phthalic dialdehyde, terephthaldehyde and malonic dialdehyde.

Bonsen et al. (III, U.S. Pat. No. 4,053,590), extends the disclosure of Bonsen et al. ('200) and Bonsen et al. ('401) with a discussion of physiologically acceptable polymeric plasma substitutes as carriers for the blood substitute. Further, applications for use as an artificial oxygen exchange solution in conventional oxygenators such as cardiac by-pass, extracorporeal circulatory assist devices, and hollow-fiber and sheet type membrane devices for use in assisting the circulation in ill patients, is suggested. Additionally, the polyhemoglobin is suggested as a source of protein and oxygen in the microbiological assay of foods for aerobic bacillus and staphyllococcus to ensure the food is safe for animal and human consumption and as a storing and preserving solution for viable isolated perfused mammalian organs for their eventual transplant into a recipient.

Bonhard et al., U.S. Pat. No. 4,136,093 discloses a hemoglobin preparation suitable for intravenous injection comprising a substantially pyrogen-free condensation product of hemoglobin and pyridoxal phosphate. The hemoglobin preparation is claimed to have a retention time in the blood system of from 2 to 9 hours. The product is produced by washing red blood cells with a weakly alkaline solution, hemolyzing, and treating the resulting material with a cation exchange resin. The material is separated from the resin, diluted to a hemoglobin concentration of about 5–9%, adjusted to a pH of about 7 to 9, treated with pyridoxal-5-phosphate and, optionally, treated with a solution of a borohydride and then a dialdehyde to cross-link the hemoglobin molecules. The non-pyrogenic nature of the infusion solution is obtained by, as a minimum, repeated washings with the weakly alkaline solution.

In Bonhard et al., U.S. Pat. No. 4,336,248, hemoglobin molecules were coupled to increase their intravascular residence time without significantly diminishing the oxygen transport ability of the molecule. The hemoglobin molecules are coupled to one another and/or to serum proteins and gelatin derivatives using dialdehydes such as aliphatic dialdehydes of 3–8 carbon atoms. Optionally, pyridoxal phosphate may be added subsequently. The coupled hemoglobin molecules are recovered by ammonium sulphate precipitation.

In Simmonds et al., U.S. Pat. No. 4,401,652, there is disclosed a process for preparing a "stromal-free" hemoglobin solution. The Simmonds et al. process is particularly adapted for large scale production of "stromal-free" hemoglobin, with reduced methemoglobin formation. The process comprises washing blood cells to remove non-cellular components, removing leukocytes, typically by filtration through a suitable adsorbent which preferentially retains the leukocytes, lysing the remaining red blood cells ultrasonically or mechanically, precipitation of the hemoglobin by mixture with a polyvalent cation, a polysulphate, and a polyvalent anion, and final purification by filtration and dialysis. The resulting hemoglobin solution is "substantially pure" and "free of stroma" and other lipoprotein cellular constituents and contains less than 5% methemoglobin.

Tye, U.S. Pat. No. 4,529,719 discloses "stromal-free" tetrameric hemoglobin which is cross-linked with certain bis-disalicyl esters and modified with pyridoxyl-5'-phosphate followed by reduction to produce bis-diamide covalently cross-linked, pyridoxyl-5'-phosphate covalently modified, tetrameric hemoglobin. The modified cross-linked "stromal-free" tetrameric hemoglobin is disclosed to be disease-free and capable of transporting oxygen to perfused tissue and remains in the intravascular space. Additionally, the product is suggested to be free from cell surface antigens, making it suitable for transfusion in place of red blood cells.

The modified cross-linked, "stromal-free" tetrameric hemoglobin of Tye is produced by starting with red blood cells of freshly drawn, outdated, or frozen packed cells or whole blood. The blood is drawn in sterile fashion into containers with sufficient anticoagulant activity to prevent clot formation. Hemoglobin from a variety of mammalian sources, such as human, bovine, ovine, or porcine are disclosed to be useful. Any non-heme protein is removed, preferably by zinc precipitation. Hemoglobin is released from the red blood cells by hypotonic lysis followed by ultrafiltration. The filtered hemoglobin is passed through a subsequent filtration step to remove virus particles, protein aggregates, and stromal elements. The typical filter has a nominal pore size of 0.020 microns and an exclusion for globular proteins of 1,000,000 Daltons. Zinc iron is added to precipitate the hemoglobin and the precipitate concentrated by filtration. The non-heme protein is removed in the filtrate. The resulting hemoglobin is then cross-linked using the bis-disalicyl esters and treated with pyridoxyl-5'-phosphate, followed by reduction of the reversible Schiff base covalent bond.

Kothe et al., U.S. Pat. No. 4,526,715 discloses a method for producing highly purified hemoglobin solutions free of plasma proteins and residual stromal lipids prepared from human blood or from animal blood in quantities large enough for clinical applications. The disclosed process comprises contacting red blood cells with a washing solution, hemolysing by introduction of the concentrated red blood cells into 2-3 times the volume of water, separating the stroma from the hemoglobin by ultrafiltration, and concentration in a third filtration stage utilizing a second ultrafiltration unit having a permeability of 10,000 to 50,000 Daltons.

However, in spite of the recent advances in the preparation of "stromal-free," cross-linked hemoglobin origin blood substitutes, the need has continued to exist for a blood substitute which is substantially free of endotoxins, phospholipids, and non-hemoglobin proteins, which is capable of 1) transporting adequate amounts of oxygen to tissue under ambient conditions; 2) having an oncotic activity equivalent to that of whole blood; 3) having an adequate intravascular retention time; 4) transfusible to all recipients without cross-matching or sensitivity testing; 5) free from disease agents such as bacteria and virus particles (hepatitis, AIDS, etc.); and 6) storable with minimum amounts of refrigeration.

SUMMARY OF THE INVENTION

Recognizing the long-standing need in the field to develop a blood substitute comprising an oncotically active protein solution capable of transporting oxygen and readily available when massive transfusions are required, the inventors endeavored to develop a blood substitute based on a hemoglobin solution. Further, recognizing that the massive demands for such a blood substitute would require volumes of starting material far in excess of that which could potentially be made available as discarded human blood, a further goal of the present invention was to generate a process for creating such a blood substitute wherein nonhuman mammalian blood sources would be suitable as starting materials.

With these goals in mind, the following invention has resulted, a semi-synthetic blood substitute comprising monomeric mammalian hemoglobin in cross-linked form, said semi-synthetic blood substitute being substantially free of endotoxins, phospholipids and non-hemoglobin proteins such as enzymes. An additional aspect of the present invention comprises the process by which the aforementioned blood substitute is prepared. Essentially, the blood substitute is prepared from a mammalian blood fraction by a process comprising 1) separation of red blood cells from the mammalian blood fraction; 2) hemolysis of the red blood cells to produce a composite of monomeric hemoglobin and stroma, including phospholipids; 3) separation by filtration of the hemoglobin, contaminated with at least a portion of the phospholipid; 4) purification of the monomeric hemoglobin by high performance liquid chromatography (HPLC) to separate the hemoglobin from all other proteins residual of the red blood cells, as well as the phospholipid, enzyme and endotoxin contaminants; 5) cross-linking (polymerizing or aggregating) the monomeric hemoglobin; and 6) partially separating the cross-linked hemoglobin from the non-cross-linked hemoglobin. An essential aspect of the present process comprises conducting the above steps under conditions which result in a product which is substantially free of endotoxins, phospholipids and non-hemoglobin proteins such as enzymes, and has a defined molecular weight distribution of greater than about 90% between 68,000 daltons and 500,000 daltons.

The resulting product (hereinafter "Invention Hemoglobin") is a blood substitute which is substantially free of endotoxins, has vascular persistence of at least two days, has the property of reversibly binding gaseous ligands such as oxygen and is useful for transporting and supplying oxygen to vital tissues and organs. As such, the blood substitute of the present invention is useful as a blood expander and resuscitating fluid in the management of disease and for maintaining circulatory integrity where needed, i.e., in response to sudden and massive blood loss.

BRIEF DESCRIPTION OF THE DRAWINGS

FIG. 1A refers to the blood collection phase. FIG. 1B refers to the blood separation phase. FIG. 1C refers to the microporous filtration phase. FIG. 1D refers to the ultrafiltration phase. FIG. 1E refers to the column chromatography phase. FIGS. 1F and 1G refer to the cross-linking phase. FIG. 1H refers to the storage and process fluid preparation phase.

In FIG. 16, the ordinate represents arterial oxygen content while the abscissa represents hematocrit.

FIG. 21 is a graphic representation of experimental data collected during the course of Example X. FIG. 21(A) is data collected from four test dogs, while

In FIG. 22, the ordinate represents the liters per minute of cardiac output (flow) while the abscissa represents time in minutes.

In FIG. 23, the ordinate represents arterial oxygen content while the abscissa represents time in minutes.

DESCRIPTION OF THE PREFERRED EMBODIMENTS

Figure 1A:
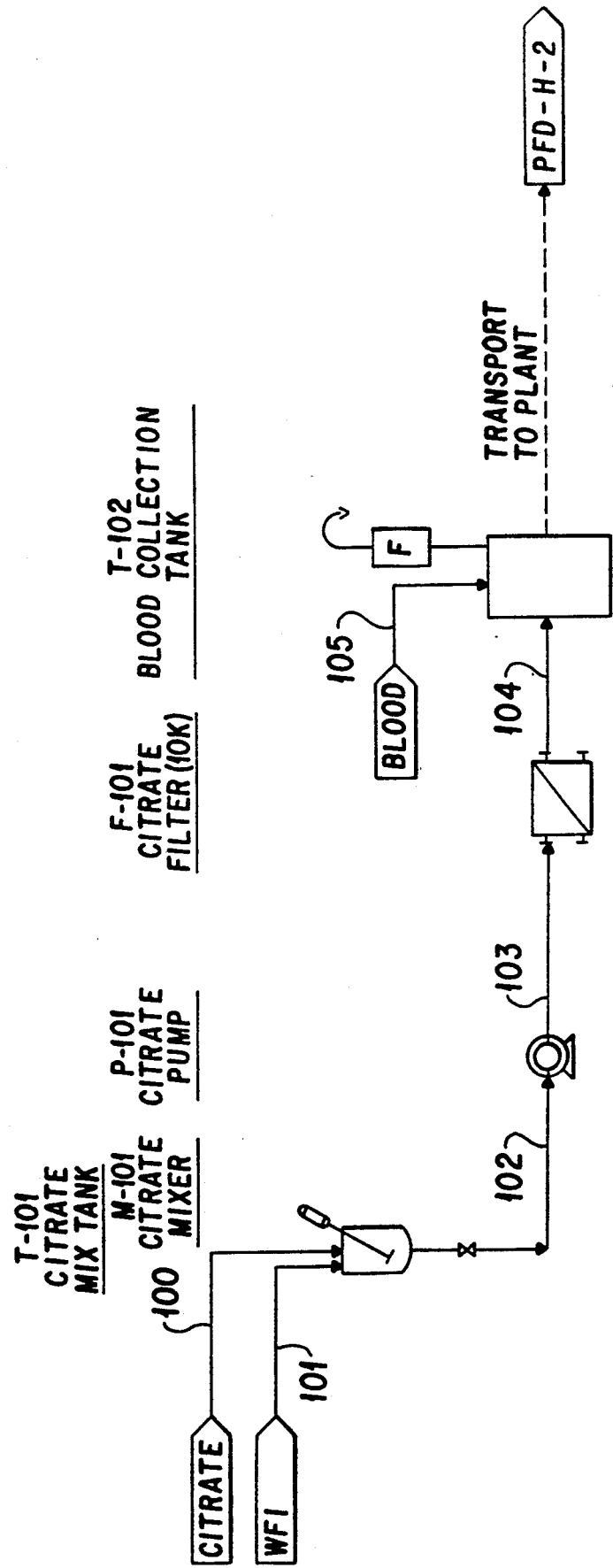
FIGS. 1A-1H are flow sheets describing the process of Example I.
Figure 1B:
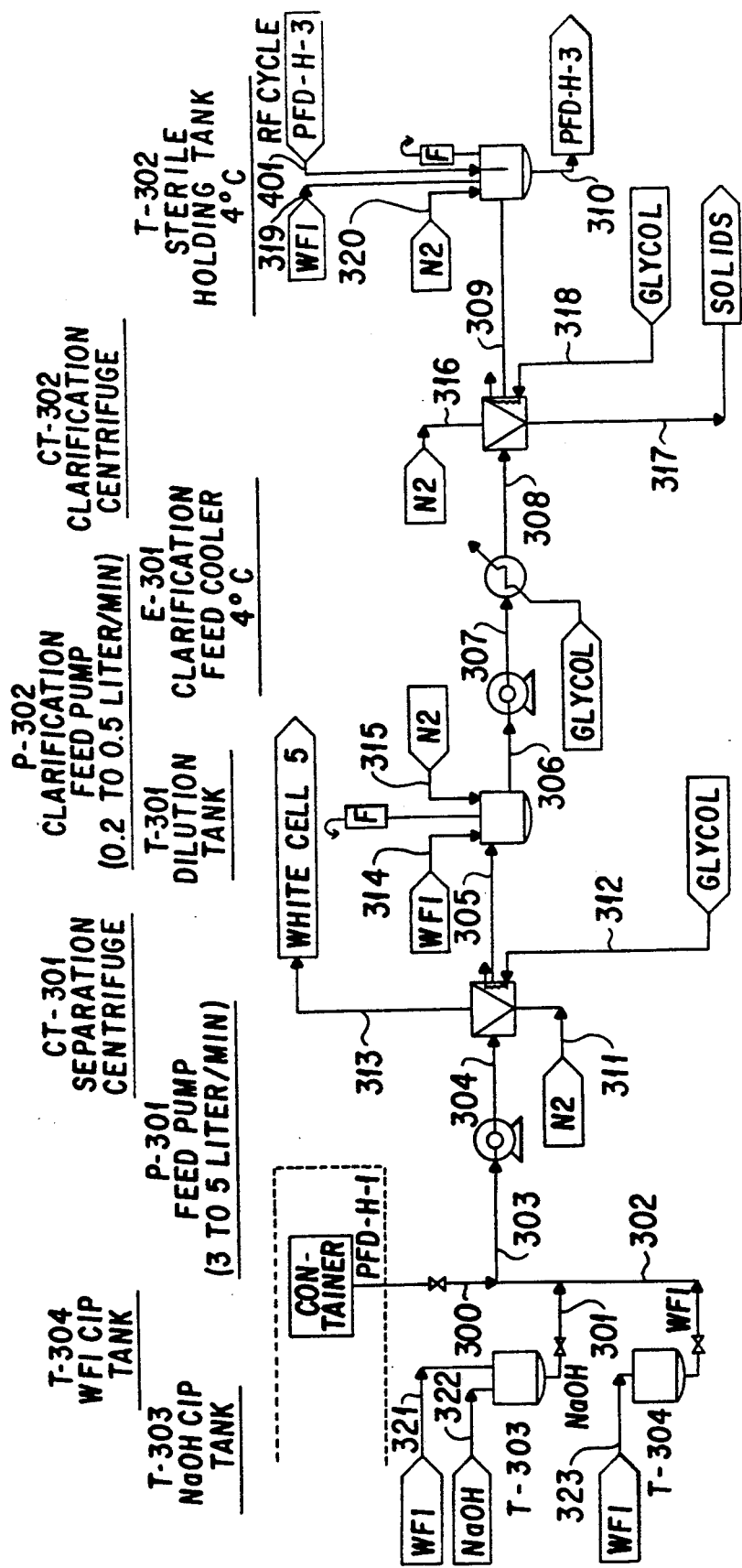
Figure 1C:
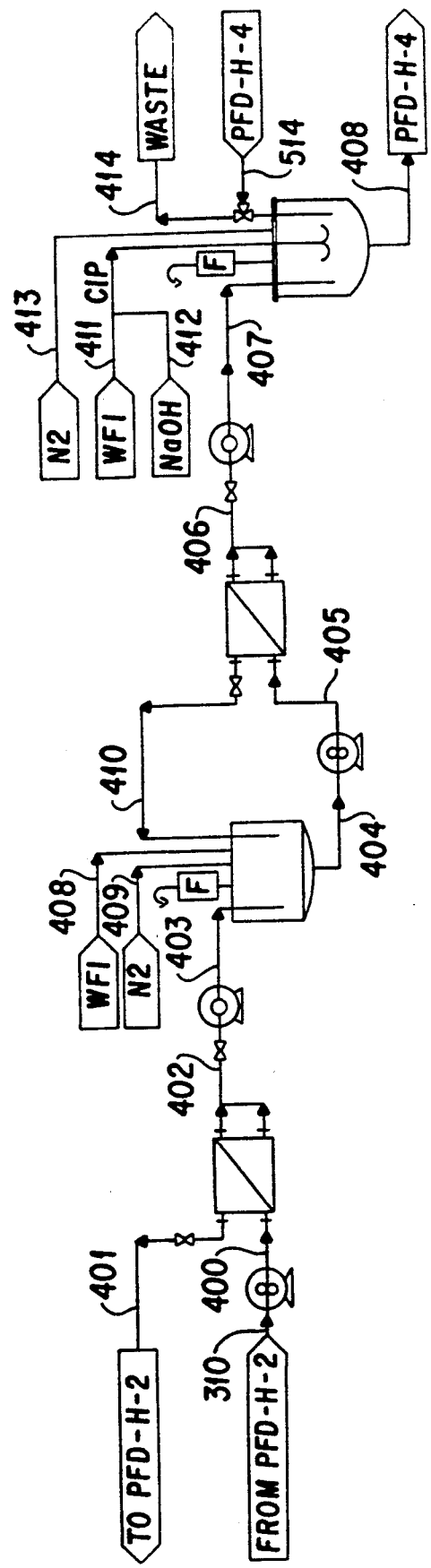
Figure 1D:
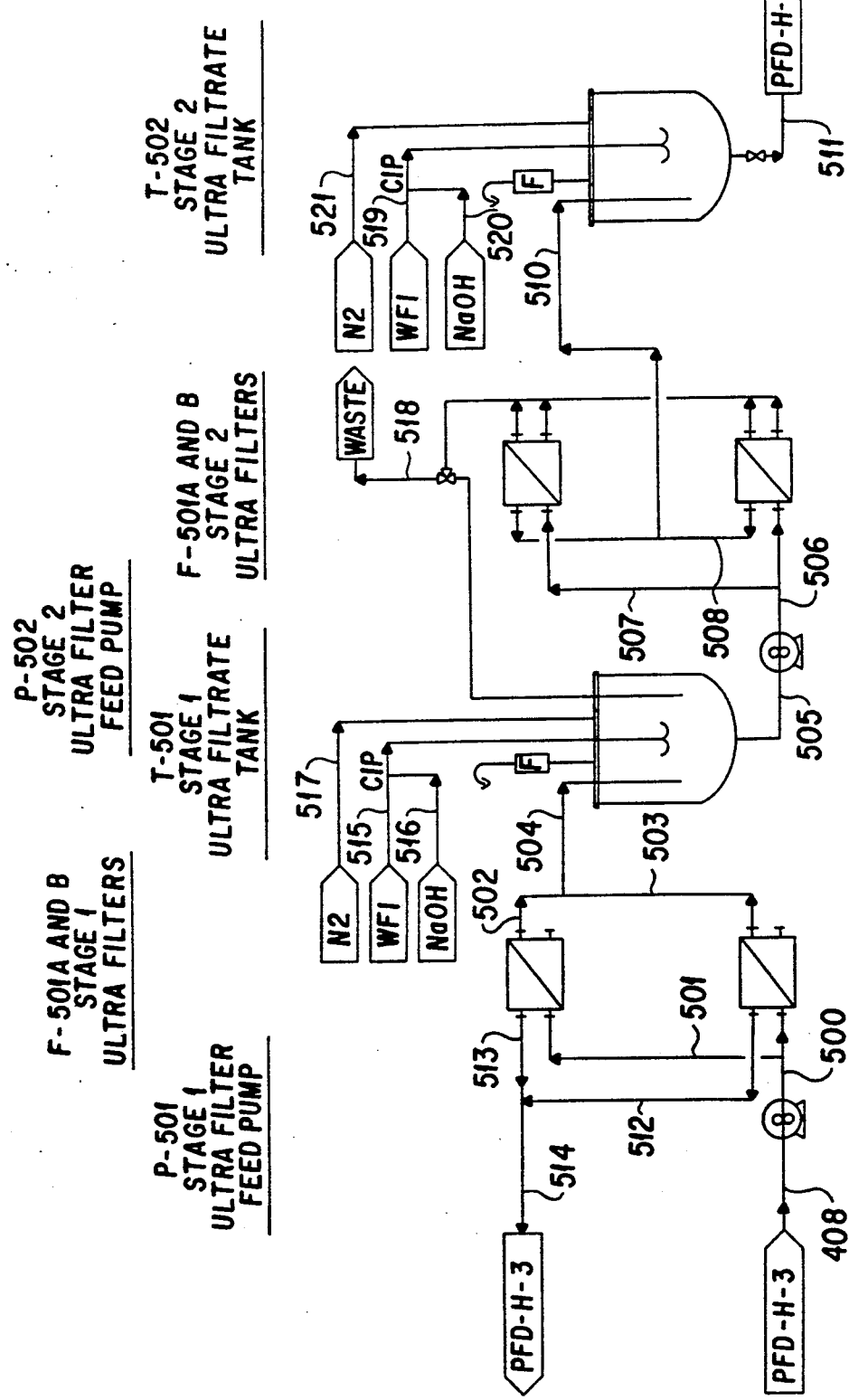
Figure 1E:
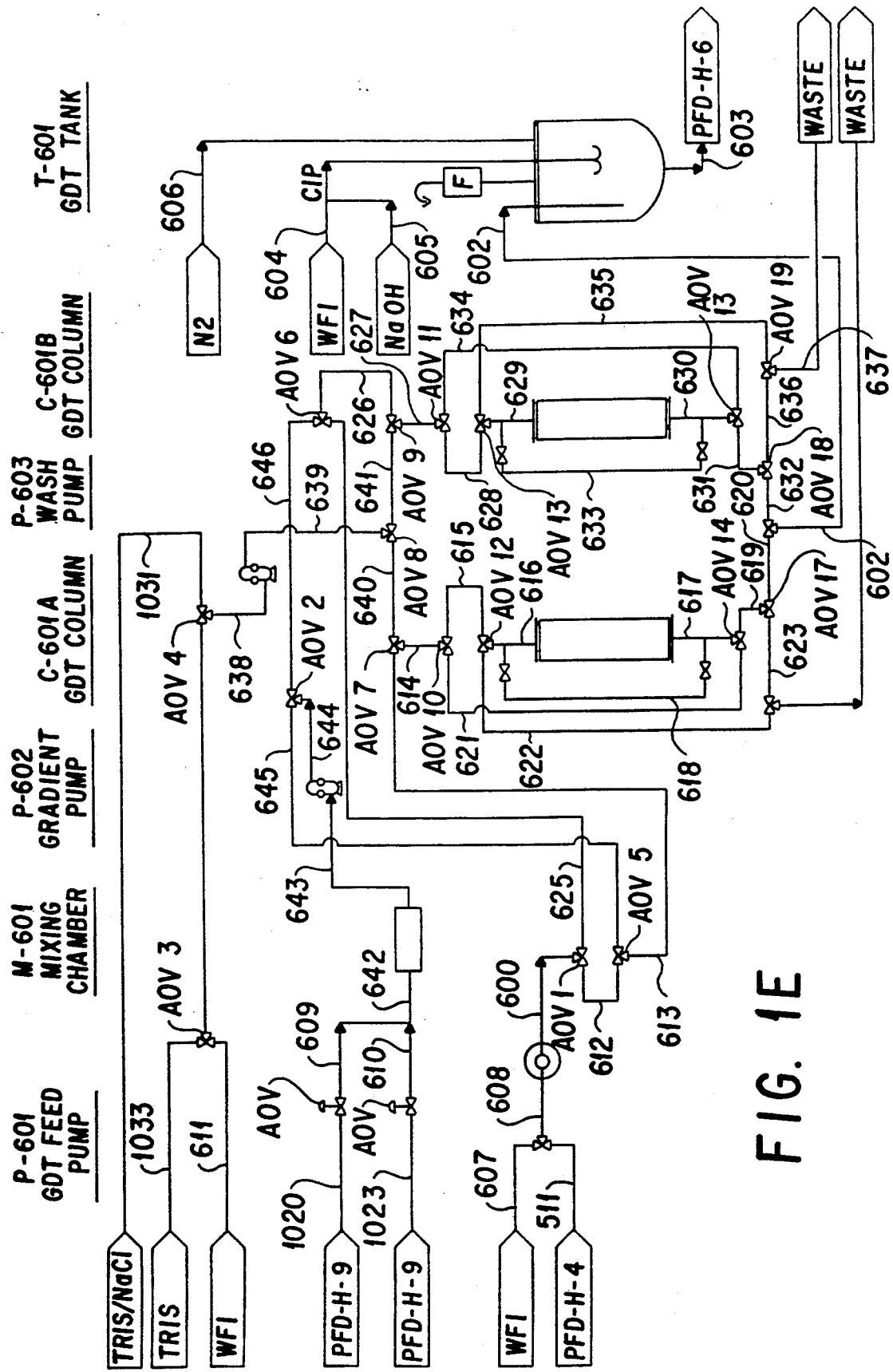
Figure 1F:
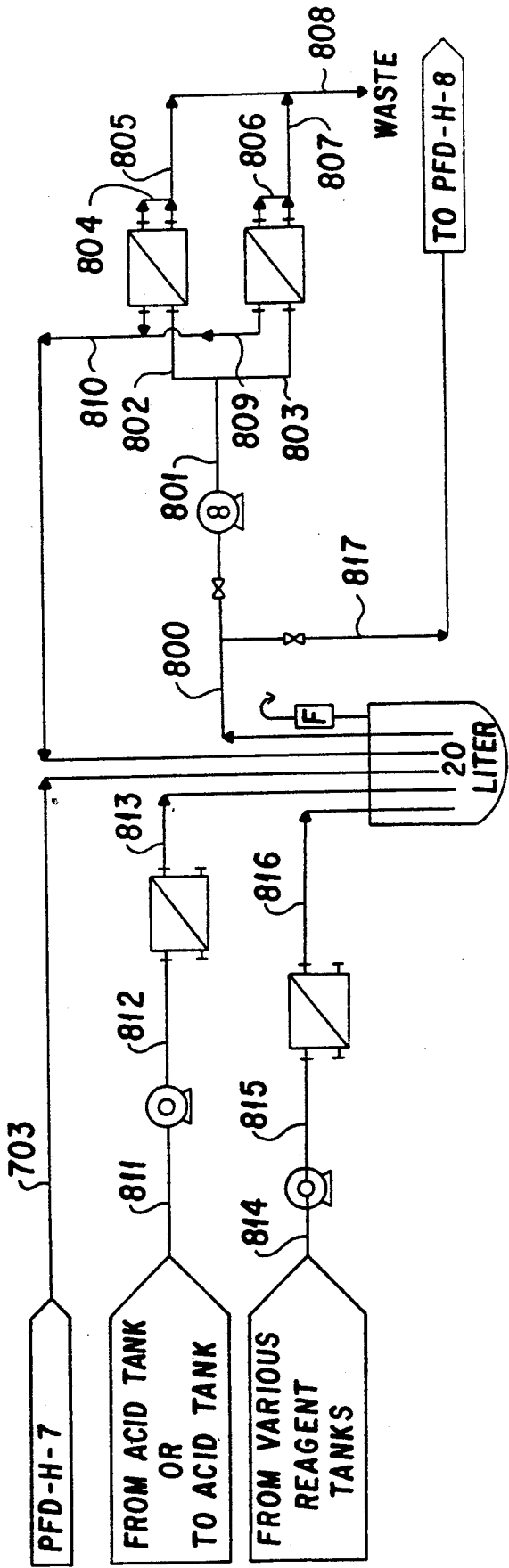
Figure 1G:
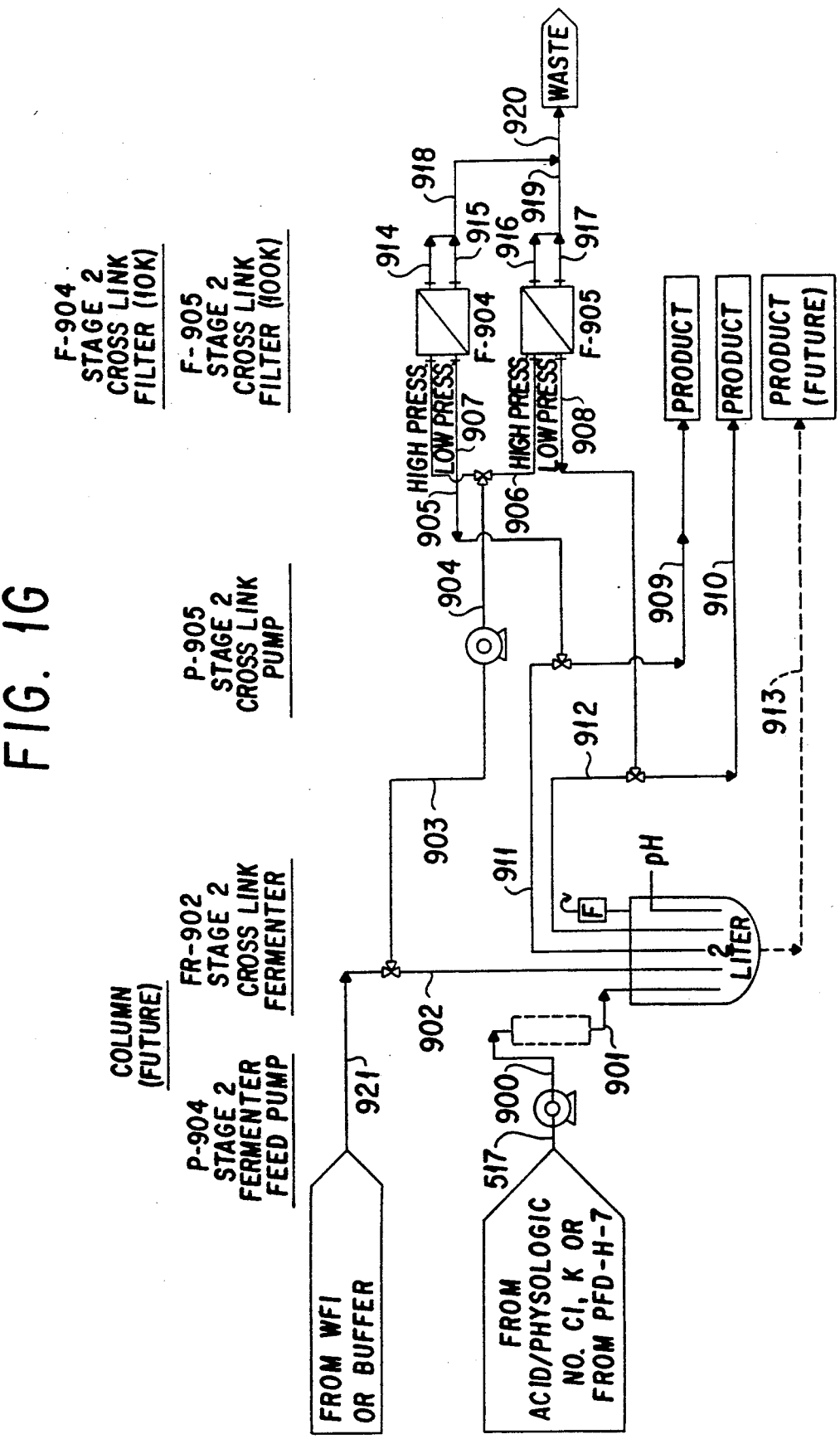
Figure 1H:
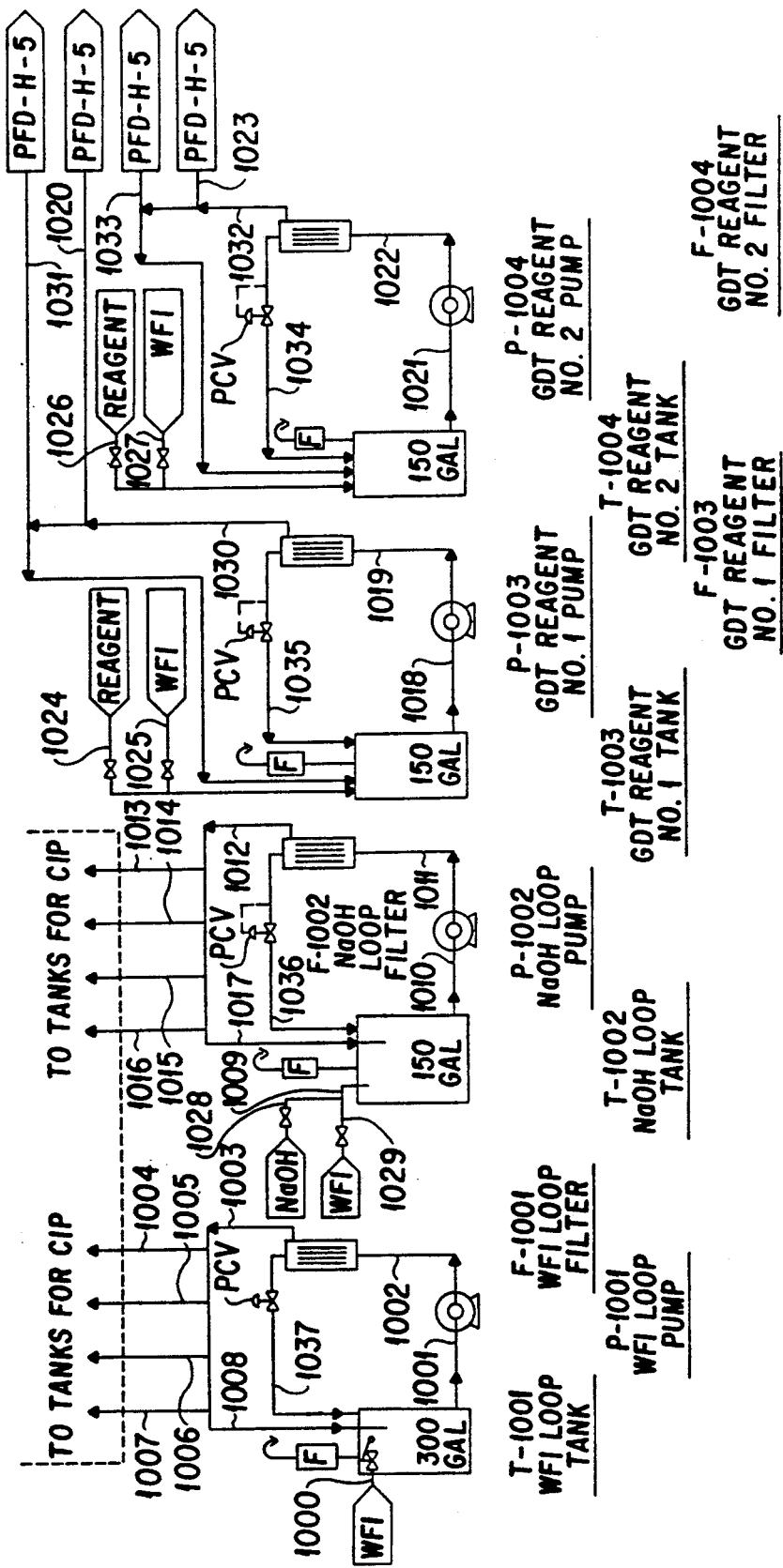

The product of the present invention comprises a mammalian blood substitute which is a cross-linked hemoglobin solution having a molecular weight distribution of greater than about 90% in the range of 68,000 to 500,000 Daltons, osmolarity as measured by freezing point depression in the range of 180–320 milliosmoles per liter of solution, a final hemoglobin content of 5-25, preferably 9-13 grams per deciliter, a methemoglobin content of less than about 20% and preferably less than about 1 0%, physiologic levels of sodium chloride and potassium chloride, less than about 1 nanomole of phospholipid per milliliter, less than about 1 part per million of cross-linking agent, a $P_{50}$ in the range of about 18-36, preferably about 24-32 mm Hg, and an intravascular half-life of at least 4 days, with at least a portion of the material remaining in the body for at least 6 to 8 days.

The term "$P_{50}$" is recognized in the art to describe the interaction between oxygen and hemoglobin and represents the partial pressure of oxygen (pO2) at a 50% saturation of hemoglobin. This interaction is frequently represented as an oxygen dissociation curve with the percent saturation of hemoglobin plotted on the ordinate axis and the partial pressure of oxygen in millimeters of mercury (mm Hg) or torrs plotted on the abcissa.

By the term "intravascular half-life" is intended the period of time in which the initial amount of hemoglobin in an in vivo environment falls to half its initial value.

The blood substitute is further characterized by a cross-linking profile on gel permeation chromatography of 50-70% cross-linking, with no material having a molecular weight of less than 68,000 being detectable.

The profile for gel permeation chromatography of the blood substitute can be characterized by integration from low molecular weight to total excluded volume where the amount of cross-linking is from 50% to 75 or 80%. A preferred embodiment of the invention shows a molecular weight distribution of greater than about 90% in the range from 68,000 MW to 500,000 MW where no more than 10 to 15% of the material is in the excluded volume which is in the range of 400,000 to 500,000 MW and higher. After careful filtration, the gel permeation chromatogram also shows that almost none of the material, if any, is below the 68,000 MW level. The initial 68,000 molecular weight peak of pure hemoglobin as measured by gel permeation chromatography is broadened after polymerization such that the retention time of 68,000 MW is somewhat complexed so that it is larger—up to 90,000 MW. Integration can be performed on this final peak such that it is found that at least 20% will be in the 68,000 MW range. This fraction does not cause a toxic response in the animal, but is merely excreted by the kidneys and can be shown in the urine upon sampling.

Additionally, the blood substitute is substantially endotoxin free and pyrogen free as well, and does not cause any of the following abnormal and detrimental chemical and physiologic functions in vivo: (1) does not activate complement; (2) does not cause hemorrhagic disorders; (3) does not cause abnormal platelet function or aggregation; (4) does not cause abnormal prothrombin times (PT); (5) does not cause abnormal partial thromboplastin times; (6) does not interfere with blood typing or cross-matching; (7) is non-toxic to the kidneys in 3.5 grams per kilogram per body weight or 8 grams per deciliter circulating blood volume; (8) exhibits circulating persistence of at least seven days; and (9) acts as a stimulus to accelerated erythropoiesis.

By the term "blood substitute" is intended to be a material having the ability to transport and supply oxygen to vital organs and tissues and to maintain intravascular oncotic pressure. Accordingly, the term encompasses materials known in the art as "plasma expanders" and "resuscitation fluids" as well.

The term "cross-linked" or "polymerized" is intended to encompass both inter-molecular and intramolecular polyhemoglobin, with at least 50% of the polyhemoglobin of greater than tetrameric form.

Figure 2:
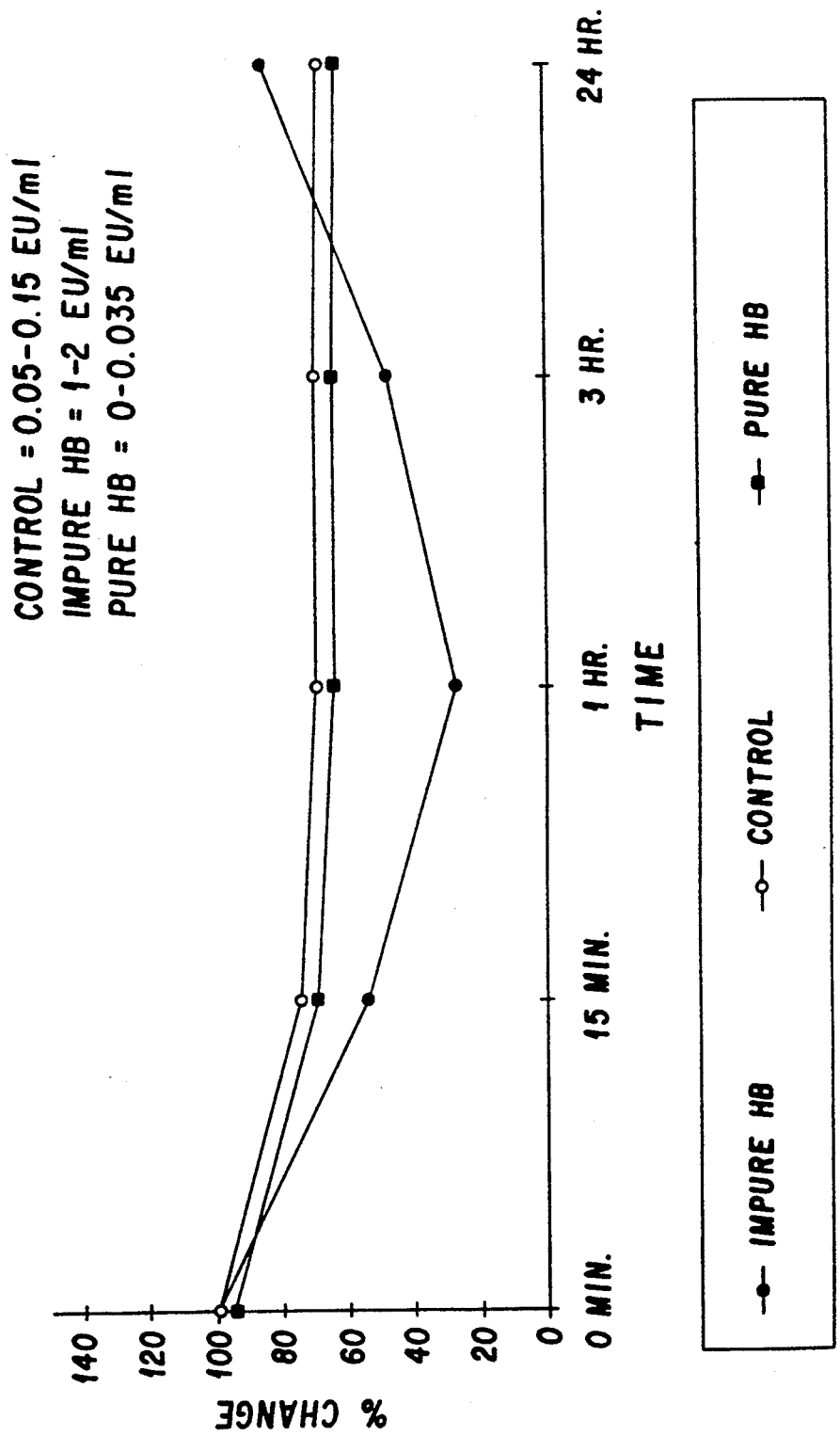
FIG. 2 is a graphic comparison of platelet numbers between three groups of rabbits, with percent change from baseline represented on the ordinate and time represented on the abscissa $T_1$ represents the baseline platelet level; $T_2$ represents the platelet level at 15 minutes post-transfusion; $T_3$ represents the platelet level at 1 hour post-transfusion; $T_4$ represents platelet level at 3 hours post-transfusion; and $T_5$ represents platelet level at 24 hours post-transfusion. The solid circles represent the mean value ± standard error for platelet levels for six rabbits having one-third of estimated blood volume replaced with a hemoglobin solution containing between one and two endotoxin units (EU)/ml; the clear circles represent the mean value ± standard error for platelet levels of four rabbits that had one-third of blood volume replaced with 5% Plasma Protein Fraction (commercial product found to contain 0.05–0.15 EU/ml); and the squares represent the mean value ± standard error for six rabbits that had one-third of the estimated blood volume replaced with pure polymerized hemoglobin according to the present invention, said hemoglobin containing 0–0.35 EU/ml.
Figure 3:
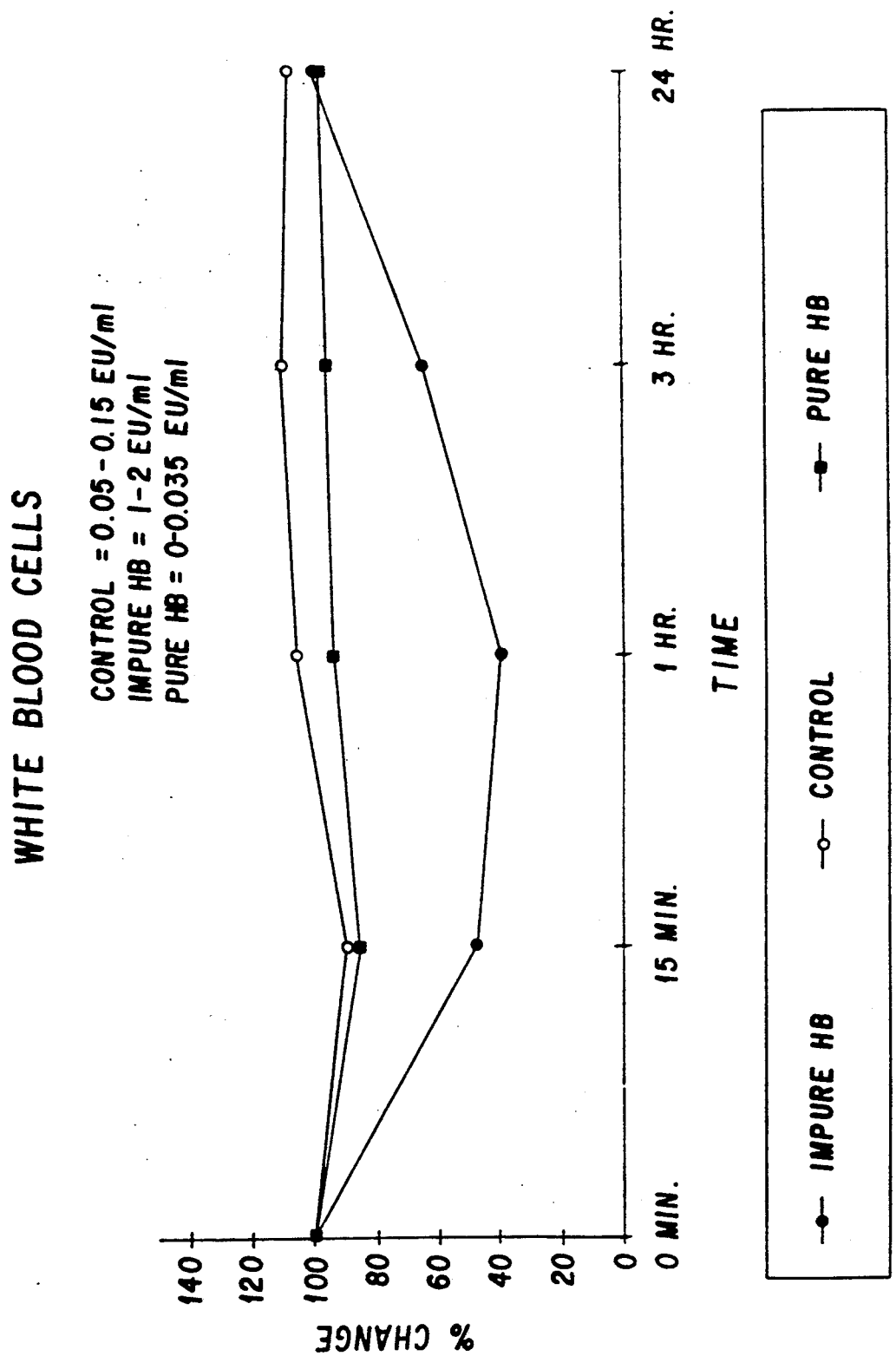
FIG. 3 is a graphic representation comparing white blood cell levels for one-third transfused rabbits from baseline to 24 hours. As in FIG. 2, the ordinate represents percent change, with the abscissa representing time. $T_1$ represents the baseline platelet level; $T_2$ represents the platelet level at 15 minutes post-transfusion; $T_3$ represents the platelet level at 1 hour post-transfusion; $T_4$ represents platelet level at 3 hours post-transfusion; and $T_5$ represents platelet level at 24 hours post-transfusion. The solid circles represent the mean value ± standard error of 6 rabbits that had one-third of the estimated blood volume replaced with a hemoglobin solution containing between 1 and 2 EU/ml; the clear circles represent the mean value ± standard error of four rabbits that had one-third of the estimated blood volume replaced with 5% Plasma Protein Fraction (commercial product found to contain 0.05–0.15 EU/ml); and the squares represent the mean value ± standard error of 6 rabbits that had one-third of the blood volume replaced with pure polymerized hemoglobin according to the present invention, containing 0–0.35 EU/ml.
Figure 4:
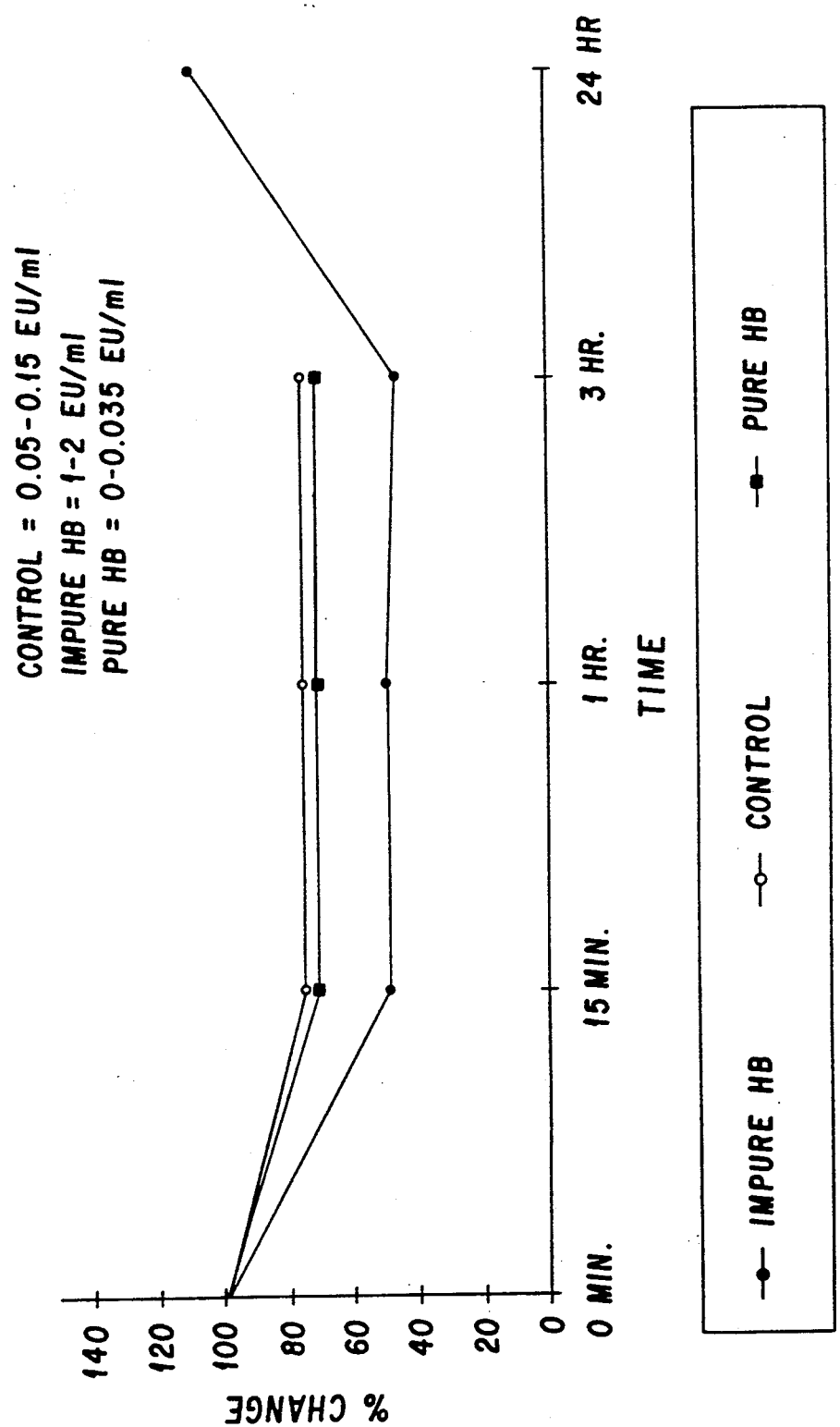
FIG. 4 is a graphic comparison of serum fibrinogen levels between three groups of rabbits. The ordinate represents the percent change in fibrinogen levels; the abscissa represents the time period, with $T_1$ representing baseline; $T_2$ the value at 15 minutes post-transfusion; $T_3$ the value at one hour post-transfusion; $T_4$ the value at 3 hours post-transfusion and $T_5$ the value at 24 hours post-transfusion. The solid circles represent the mean value ± standard error for six rabbits with one-third of the estimated blood volume replaced with a hemoglobin solution that contained between 1 and 2 EU/ml; the clear circles represent the mean value ± standard error for four rabbits that had one-third of blood volume replaced with 5% Plasma Protein Fraction (commercial product found to contain 0.05–0.15 EU/ml); and the squares represent the mean value ± standard error of six rabbits that had one-third of blood volume replaced with pure polymerized hemoglobin, containing 0–0.35 EU/ml.
Figure 5:
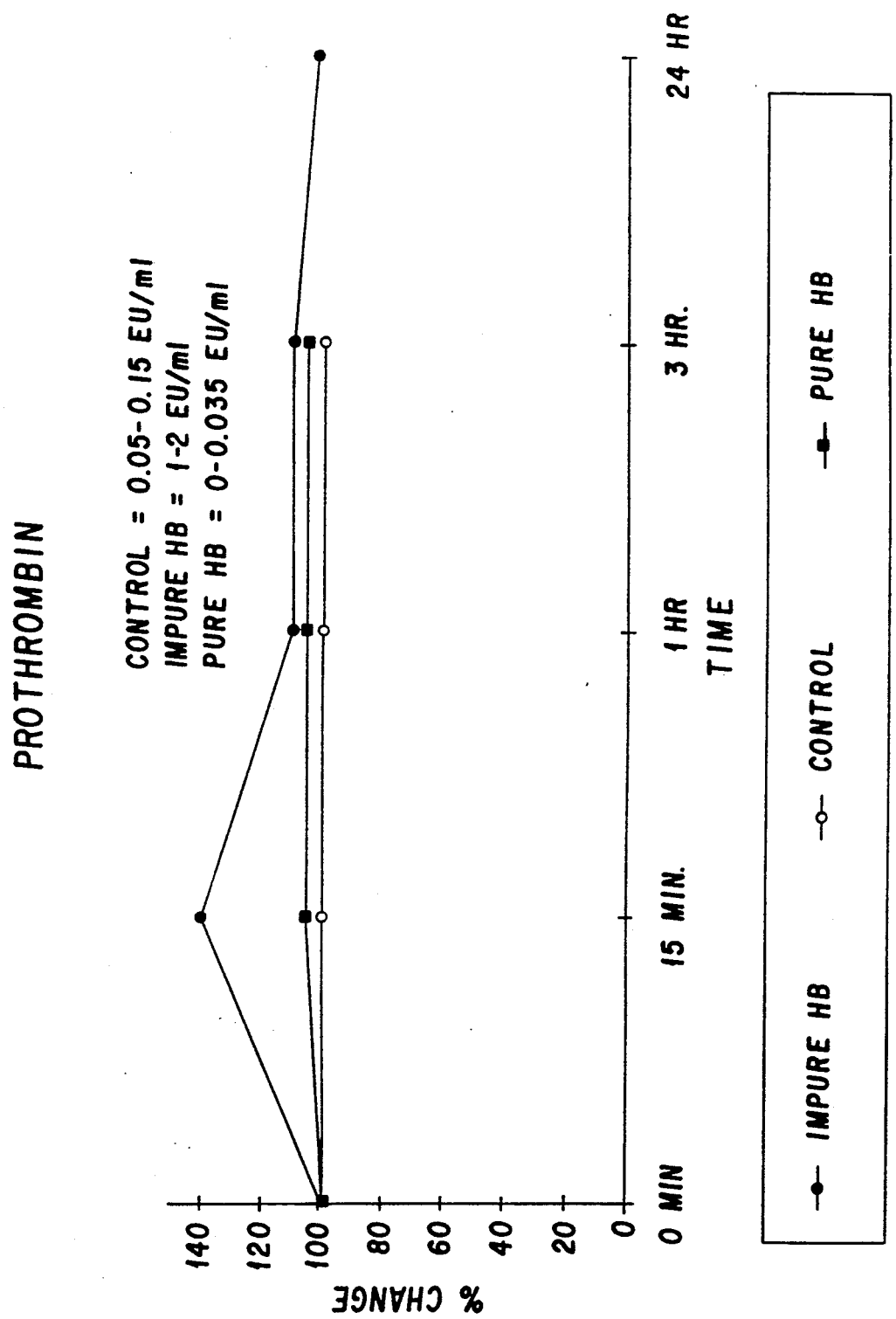
FIG. 5 represents a graphic comparison of prothrombin levels between three groups of rabbits. The ordinate represents the percent change in prothrombin levels, with the abscissa representing time. $T_1$ represents the baseline prothrombin level; $T_2$ represents prothrombin levels at 15 minutes post-transfusion; $T_3$ represents prothrombin levels at 1 hour post-transfusion; $T_4$ represents prothrombin levels at 3 hours post-transfusion; and $T_5$ represents prothrombin levels at 24 hours post-transfusion. Solid circles represent the mean value ± standard error of six rabbits that had one-third of the estimated blood volume replaced with a hemoglobin containing between 1 and 2 EU/ml; the clear circles represent the mean value ± standard error of four rabbits that had one-third of the estimated blood volume replaced with 5% Plasma Protein Fraction (commercial product found to contain 0.05–0.15 EU/ml); and the squares represent the mean value ± standard error of six rabbits that had one-third of the estimated blood volume replaced with pure polymerized hemoglobin, containing 0–0.35 EU/ml.
Figure 6:
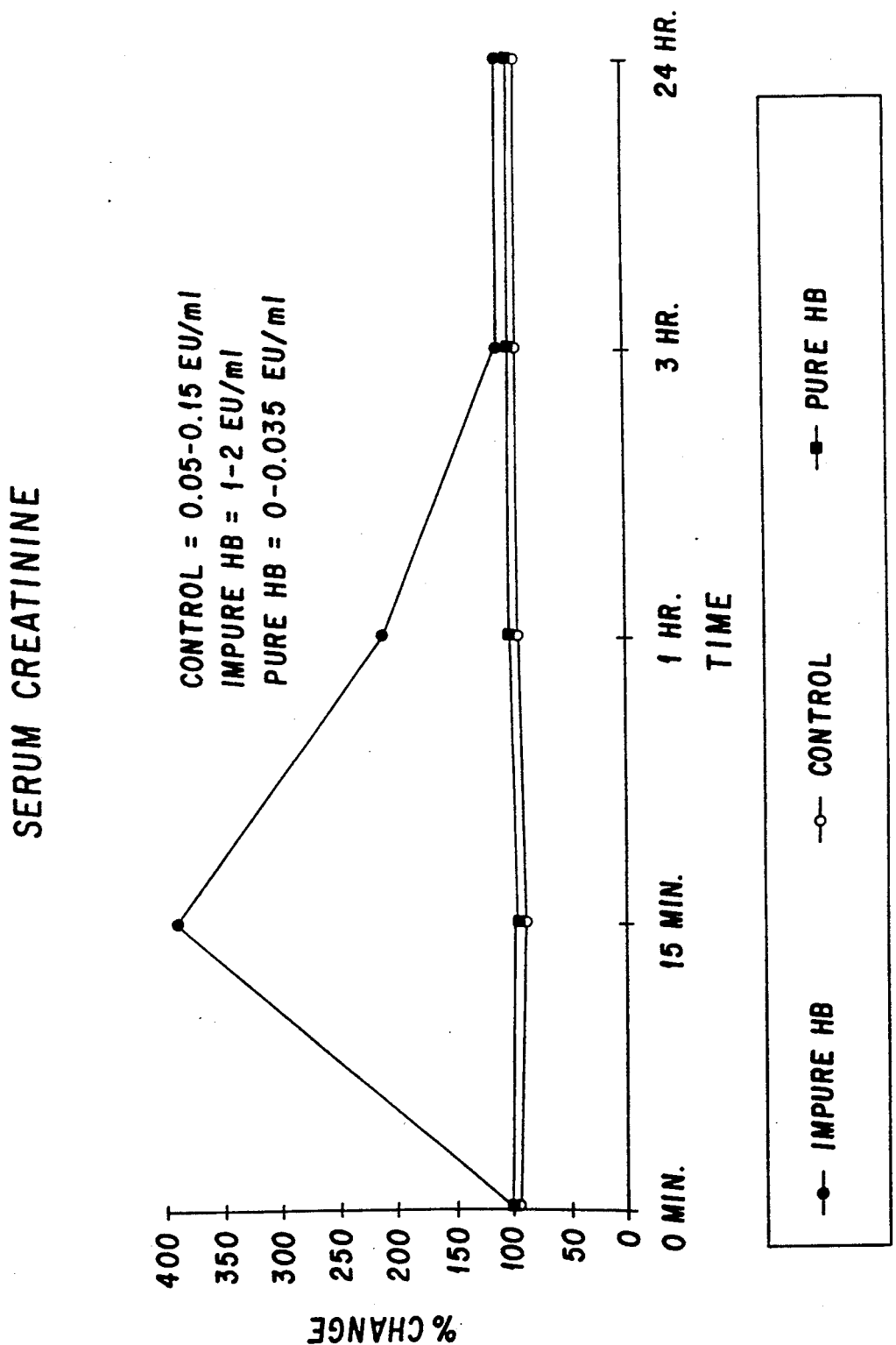
FIG. 6 is a graphic representation comparing serum creatinine levels between three groups of rabbits. The ordinate represents the percent change in serum creatinine levels, with the abscissa representing time. $T_1$ represents the baseline serum creatinine level; $T_2$ represents serum creatinine levels at 15 minutes post-transfusion; $T_3$ represents serum creatinine levels at 1 hour post-transfusion; $T_4$ represents serum creatinine levels at 3 hours post-transfusion; and $T_5$ represents serum creatinine levels at 24 hours post-transfusion. Solid circles represent the mean value ± standard error of six rabbits that had one-third of the estimated blood volume replaced with a hemoglobin solution containing between 1 and 2 EU/ml (Chromogenic LAL test); the clear circles represent the mean value ± standard error of four rabbits that had one-third of the estimated blood volume replaced with 5% Plasma Protein Fraction (commercial product found to contain 0.05–0.15 EU/ml); and the squares represent the mean value ± standard error of six rabbits that had one-third of the estimated blood volume replaced with pure polymerized hemoglobin, containing 0–0.35 EU/ml.
Figure 7:
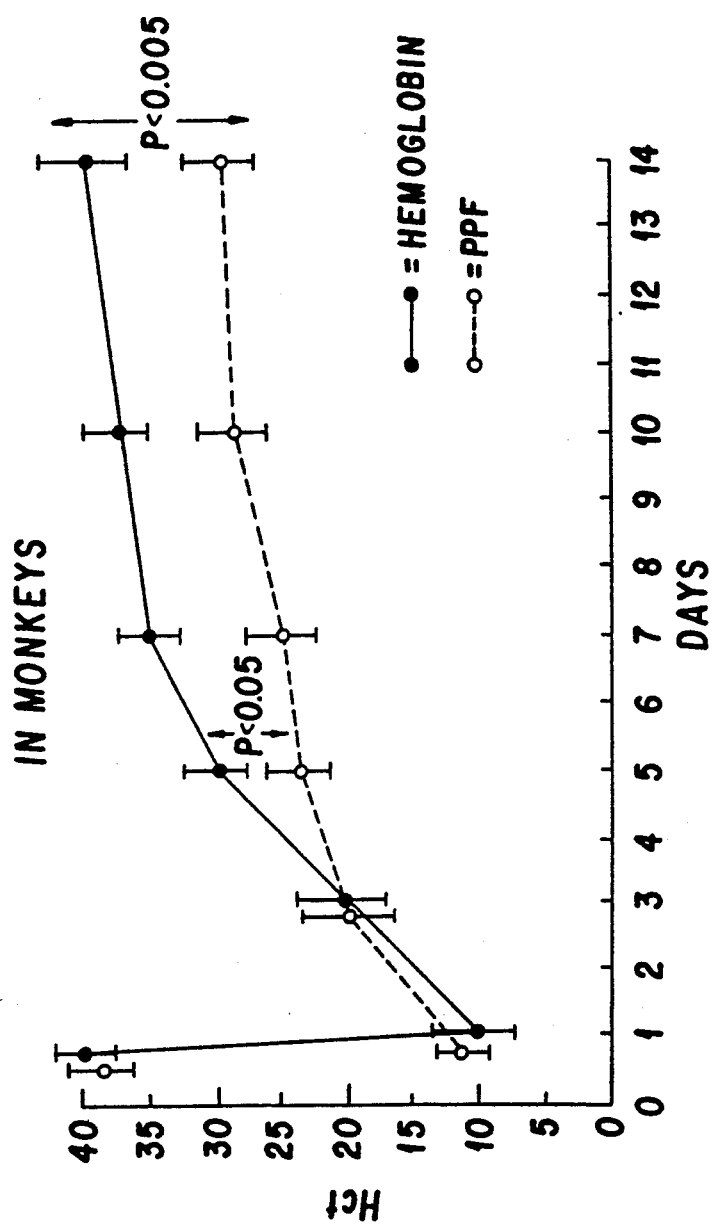
FIG. 7 represents a graphic comparison of the changes in hematocrit (Hct) following a 50% hemorrhage-transfusion in monkeys. The ordinate represents the hematocrit with the abscissa representing the time in days. Hematocrits of hemoglobin-transfused monkeys are noted with the solid circles; hematocrits of Plasma Protein Fraction are denoted with the open circles.

The term "substantially endotoxin free", for the purposes of the present invention, may be described functionally as a blood substitute which contains less than 1.0 endotoxin units per milliliter of solution, at a concentration of 10 grams of hemoglobin per deciliter of solution. This blood substitute, when used as a replacement for approximately one-third of the total blood volume of a rabbit, produces a percent change in blood platelet levels, over time, which is substantially similar to Curve delta-delta of FIG. 2, or a percent change in white blood cell levels, over time, which is substantially similar to Curve delta-delta of FIG. 3, or a percent change in fibrinogen levels, over time, which is substantially similar to Curve delta-delta of FIG. 4, or a percent change in pro-thrombin levels, over time, which is similar to Curve delta-delta of FIG. 5, or a percent change in serum creatinine levels, over time, which is substantially similar to Curve delta-delta of FIG. 6.

In a preferred embodiment, the "substantially endotoxin free" blood substitute of the invention will contain less than 0.5, and preferably less than 0.25, most preferably less than 0.02 endotoxin units per milliliter of solution (EU/ml) as measured by the Limulus Amebocytic Lysate (LAL) assay. The LAL assay is described by Nachum et al., *Laboratory Medicine*, 13: 112-117 (1982) and Pearson III et al., *Bioscience*, 30: 461-464 (1980), incorporated by reference herein.

By the term "endotoxin(s)" is intended the generally cell-bound lipopolysaccharides produced as a part of the outer layer of bacterial cell walls, which under many conditions are toxic. When injected into an animal, endotoxins cause fever, diarrhea, hemorrhagic shock, and other tissue damage.

By the term "endotoxin unit" (EU) is intended that meaning given by the United States Pharmacopeial Convention of 1983, Page 3014, which defined EU as the activity contained in 0.2 nanograms of the U.S. reference standard lot EC-2. One vial of EC-2 contains 5,000 EU.

The present invention further involves the process for producing the semi-synthetic, substantially stromal-free blood substitute. The process comprises the steps of (1) obtaining the blood raw product, (2) fractionating the blood raw product to produce a red blood cell fraction which is substantially free from white blood cells and platelets, (3) mechanically disrupting the red blood cell fraction to produce a hemoglobin-containing solution, (4) clarifying the hemoglobin-containing solution to produce a hemoglobin solution which is substantially free of cellular debris, (5) microporously filtering the hemoglobin solution which is substantially free of cellular debris to produce a partially sterilized hemoglobin-containing solution, (6) ultrafiltering the partially sterilized hemoglobin-containing solution to produce a size-separated hemoglobin-containing solution, (7) chromatographically separating the size-separated hemoglobin-containing solution to produce a hemoglobin substantially free of phospholipids and non-hemoglobin proteins, said hemoglobin retained on the chromatographic column, (8) eluting the substantially phospholipid-free hemoglobin from the column to produce a substantially endotoxin-free hemoglobin solution, (9) cross-linking said substantially endotoxin-free hemoglobin solution to produce the cross-linked blood substitute, and (10) partially separating the cross-linked blood substitute by filtration, all steps done in a substantially endotoxin-free environment.

Each of the process steps will be described in greater detail below.

I. THE PROCESS

A. Blood Collection

Starting point in the present invention is an erythrocyte (red blood cell) source. As such, the starting material may be freshly drawn human blood, outdated old blood from blood banks, placentas, or packed erythrocytes obtained from human donor centers. Additionally, erythrocytes obtained from animal blood are entirely suitable as well. Accordingly, blood from a variety of sources such as bovine, ovine, or porcine may be used. Because of its ready availability, bovine blood obtained from slaughterhouses is the preferred erythrocyte source.

The unique approach of the present invention has required special techniques in the collection and handling of blood in large quantities. Large collection trochars are used which extract the blood in a sterile manner. The trochars require careful insertion and handling and are connected to tubing approximately 2 feet in length. In order to insert the trochar the hide must be cut away, peeled back, and the trochar then inserted in the animal's major vessels close to the heart with care not to puncture the esophagus. Avoiding the introduction of bacteria and the maintainance of endotoxin-free or low endotoxin level material is important. This is accomplished using individual containers that are precharged with an anticoagulant and that are depyrogenated and re-checked for endotoxins. Typical anticoagulants include sodium citrate. In all cases, endotoxin levels of the containers must be less than 0.01 endotoxin units as detected by LAL.

This solution is then charged to small vessels that can hold between 2 to 10 gallons of gathered blood in a sterile manner and, therefore, maintain the blood in an endotoxin-free state. The collected blood in its container is capped off immediately to avoid exposure to the environment. Upon completion of the collection process, the material is chilled, typically to about 4° C., to limit bacterial growth. There is no pooling of blood at this time; the blood is later checked for endotoxins and sterility to ensure that (1) no one cow is sick; or (2) a bad collection technique has not contaminated the entire batch or collection for that day. Although the above collection method is preferred, there are many collection methods which are suitable and available to one with ordinary skill in the art.

B. Red Cell Separation

The blood is brought to a processing center at which time each vessel is sampled and checked by LAL analysis for endotoxin levels. If the endotoxin level is higher than 6–7 EU per ml the blood is discarded. Only if the individual blood container tests at below that endotoxin level is the material approved for secondary processing.

Typical secondary processing of the prior art was to suspend the blood (ACD anticoagulated blood) in a saline solution of physiologic salt concentration and centrifuge in order to separate effectively the plasma proteins and white cells from the red cells. This suspension process is performed through several "washing" steps, i.e., 2-4 times, in an attempt to remove all free proteins. In the process of the present invention, however, it was found that this approach was untenable for practical manufacturing scale up; in fact, to separate the hemoglobin product free from many contaminants, it is not necessary to do this washing process at all.

In the preferred process, the whole blood from the animal, once it has been checked for endotoxins, is passed through a semi-continuous type centrifuge where the red cells, white cells and plasma can be effectively separated on as large a scale as desired. The process employs a bowl-type semi-continuous centrifuge where the bowl is maintained at 15,000 to 18,000 rpms, i.e., a Sharples AS-15 unit. The bowl and the top configuration are set up with an opening at a particular radius that permits a discrete layer separation such that red cells, white cells and plasma can be removed through the operation. While the Sharples bowl-type centrifuge is preferred, typical separation apparatus also suitable include basket centrifuges such as are manufactured by Beckman Instruments.

To prepare for this operation the centrifuge is depyrogenated, i.e. using, typically, a 0.5 molar sodium hydroxide for at least 1 hour prior to installation into the machine housing container. The top spouts or collection devices are handled in a similar fashion, thus allowing for complete depyrogenation of all contact surfaces the blood may encounter. Once the parts have been put through the depyrogenating process, the system is assembled. A lobe pump or peristaltic pump with sanitary design is used to flush fluid through the entire system and collection ports; typically, a solution of 0.5 molar sodium hydroxide is used, but other depyrogenating solutions known to the art are suitable as well. At tee completion of the flush, it is necessary to reduce the pH to a range which is conducive to the handling of the hemoglobin solution. This is accomplished through a water purge which reduces the pH to a range of approximately 7-9. In some cases it has been necessary, because of density differences between the depyrogenating solution and water, to use an acid solution to help neutralize the strong base employed in the depyrogenation step. All these solutions must be depyrogenated and checked prior to use in the washes.

Once the pH level has been brought below 9, samples are obtained from the effluent streams of the centrifuge and endotoxin testing is performed. When an endotoxin level of 0.01 EU/ml or less is achieved, the system is ready for the separation of the blood. However, in this separation it is critical that the flow rate of the blood into the centrifuge be at a sufficient rate to limit the amount of sedimentation of red blood cells caused in the Sharples centrifuge. If the flow rate is too low, the red cells will settle into the bowl of the centrifuge and not be separated or collectible into a separate container. In a centrifuge with a 4" diameter bowl, a flow rate in excess of 2.5 to 3 liters per minute, but not exceeding 6 liters per minute, is required to limit sedimentation. If a larger bowl or different g forces are employed, then different flow rates are required, the particular parameters being within the skill of the art.

Once all parameters have been established, the blood from the various batches or various cows is introduced into the system and the effluent (separated red cells) is collected under sterile conditions in a separate container. However, at this point the effluent is pooled and is no longer treated on an individual animal basis. To eliminate any variations of pH or potential initial entrapment of bacteria on the centrifuge, positive pressure sterile nitrogen is applied to the chamber where the bowl is spinning. For true sterilization of the system, a steam sterilization cycle may be applied by introducing steam into the bowl spinning chamber and steaming for up to an hour prior to use. After completion of steaming, the system is cooled i.e., through glycol coolant tubes, typically to about 4° C. (After harvesting from the animal, it is important that the blood be brought to and maintained at a temperature just above freezing, typically about 4° C.)

In the separation of the red cells it is important that the collection chamber, i.e., spout area, where the red cells are collected at the top of the high speed spinning bowl, be configured such that high impact of the cells occurs. In striking these surfaces, the red cells become broken through a mechanical degradation, as opposed to using a hypotonic solution. (In a hypotonic solution, the red cells swell and cause the membrane to rupture from hydraulic forces.) This is a change from the normal operation of swelling cells to lyse them by hydraulic pressure, to one of mechanical degradation. This mechanical degradation is extremely rapid and does not generate the high degree of free small cell membrane components found by other methods. The red cells are collected in a vessel and prepared for the second centrifuge operation.

C. Red Cell Clarification

Once the blood has been processed and the red cells have been separated from the white cells and plasma, the mechanically disrupted red cells are diluted using pure depyrogenated water which has been maintained at low temperature, i.e., about 4° C. Typically, disrupted the red cells are diluted by at least 50%. The red cells are then introduced into the second separation step; typically a similar type of centrifuge to the first operation may be used. In a preferred embodiment, a Sharples centrifuge with a 4" bowl operating in a semi-continuous mode and spinning at 15,000 to 18,000 rpms is used. The flow rate, however, is substantially decreased: 0.5 liters per minute or less is recommended. Unlike the first processing step, this step employs a different type of top configuration to the centrifugation bowl. No separation of two layers such as the plasma white cell and red cell composition is effected at this step. This clarification step results in the separation of all cell debris from the liberated hemoglobin solution. The same care taken in the first step for depyrogenation and sterility must be employed in the second step. Once this material has been collected from this second step, it is ready for microporous filtration.

D. Microporous Filtration

The microporous filtration must be operated differently than a pressure filtration mode. In a practical sense, pressure filtration is not acceptable to industrial scale processing of hemoglobin solutions. To employ microporous filtration successfully, either a plate and frame filtration or hollow fiber filtration system may be used; however, it must be operated such that the pressure drop across the membrane (the transmembrane pressure) is carefully maintained to within about 5 pounds per square inch (psi). If the pressure drop exceeds the tolerance level by 1 to 2 psi, the membrane rapidly becomes plugged with the remaining cell debris and the flux rate across the membrane drops to an unacceptable level for industrial purification in a semi-continuous mode.

While tangential flow of this material across the membrane is at a flow rate of 2 to 5 liters per minute, the flux through the membrane is on the order of 0.1 to 0.2 liters per minute. This operational rate is maintained to eliminate cellular debris from building up on the membrane. When the concentration of solution tangential to the membrane decreases to less than 10% of the initial solution, the remaining solution is discarded or it is re-diluted with water to extract additional product and thereby produce a higher yield of hemoglobin from the system.

The filtration system may utilize lobe or peristaltic pumps with sanitary design, thus decreasing and limiting seals and shafts that may cause introduction of bacteria and pyrogen contamination. Other pump designs known to the art for sanitary pumping may be used, however. Such pumps include centrifugal, gear, and tubular diaphragm pumps.

The membrane systems are pre-treated to ensure depyrogenation and proper pH. If handled improperly, pyrogens are added at this point and it becomes more and more difficult to remove them throughout the remaining processing steps. Depyrogenation and pH control is accomplished by using standard sanitation procedures and depyrogenation procedures, i.e., typically with sodium hydroxide and voluminous washings with pyrogen-free water to bring the pH to within acceptable ranges for handling of the hemoglobin solution (<pH 9). While handling of a transmembrane pressure limitation in such a manner is not well known and has only been practiced in the last few years on a selected basis with tissue fluid processing, suitable techniques are within the skill of the art.

In a preferred embodiment, a filtrate side restriction is employed such that flux rate is limited to its steady state (non-plugging) condition. If a fluid stream is applied to a tangential flow membrane system, and the inlet pressure is approximately 20 psig, the outlet pressure is 0 psig, and the filtrate side of the membrane is 0 psig, giving an average transmembrane pressure (ATP) of 10 psi., the solution to be filtered has a tendency to fill and extrude into the porous membrane surface. It will essentially plug the membrane and will not be swept clear by the tangential shear created by the cross-flow of fluid. By restricting the outlet (filtrate) so that the ATP is only 1 to 2 psi, the tangential flow sweeps the surface clear and flux across the membrane remains constant yet low when compared to initial flux rates with high ATP. The flow under steady state conditions may be 0.2 liters per minute, with 1 to 2 psi ATP, and 1 to 1 2 liters per minute with 20 psi ATP. However, the 20 psi ATP will stay constant and cause the flux to rapidly fall to zero flux within minutes.

With the completion of this first microporous filtration step, the solution has been at least partially sterilized and substantially all cell debris above 0.45 micron has been removed. In some cases it may be required to make the solution sterile at this point. In these cases, after the 0.45 micron microporous filtration has been completed a 0.22 micron filtration may be employed in the same manner as the 0.45 micron filtration. The resulting solution is now ready for the molecular separations which follow.

E. Ultrafiltration

The next step includes the careful staging of 100,000 molecular weight filtration (measured in Daltons) using membranes which effectively retain everything greater than 100,000 molecular weight and which permit everything less than 100,000 molecular weight to pass through. Typical membranes are commercially available from Millipore Corporation, and are sold under the trade name Durapore. Everything below these levels is filtered through the membrane system. Hemoglobin (about 67–68,000 molecular weight) passes through this membrane system and is collected in tankage.

This large membrane filtration operation requires careful monitoring because, over a period of hours, the membrane will become plugged and filtration flux will decrease rapidly. It is, therefore, necessary to flush the membrane on a regular basis with a pure water solution. The flushing reduces cell debris which may otherwise coat and occlude the membrane, thereby reducing hemoglobin solution flux rate. The tangential cross-flow time cycling over this membrane can be up to 2 hours and does not affect the methemoglobin level or the viability of the hemoglobin for its intended purpose. When the fluid volume after the microporous filtration has been reduced to about 30% of its volume during ultrafiltration, sterile pyrogen free water may be added to obtain greater yield of hemoglobin solution. Maximum dilution is about 50%. This material may also be discarded. If the 30% original material is diluted, it again may be reduced to about 30%, at which time it is discarded. The filtered intermediate is held in sterile, pyrogen-free tankage for subsequent operations. A typical device for effecting the ultrafiltration step is a Millipore Pellicon cassette with a Durapore membrane; however, other devices known to the art may be used as well.

The next ultrafiltration step, requires a removal of material below 68,000 molecular weight. This isolates small molecule hemoglobin and other small proteins that may have been carried over from the whole blood plasma. In all cases the hemoglobin solution is maintained at a concentration of about 5 to 15 grams per deciliter. Filtration accomplished at this step provides some degree of concentration. At high concentration, low flux rates are exhibited. In both ultrafiltration operations where 100,000 mw and 30,000 mw membranes are employed, the necessary depyrogenation steps and subsequent checking after washing with pyrogen-free water are usually required.

In the 100,000 mw separation step pyrogens may be removed since some pyrogens are between 100,000 and 1 million mw. With the depyrogenation of the 30,000 molecular weight membrane and the preparation of this membrane packet for its filtration process, the hemoglobin solution has passed over this tangential flow system to allow the perfusion of small molecules through the membrane. Recycle may or may not be used in this operation, although it is required in the 100,000 mw filtration step. The retentate (material retained), is held in a storage tank and checked for endotoxins. In all cases the endotoxins must be below 0.5 EU per ml because subsequent operations makes removal of high levels of pyrogens quite difficult. This material is stored under a sterile nitrogen or argon atmosphere that maintains stability in the tankage system. Typically the methemoglobin level is below 1% at this point in the process. The filtration steps must be performed at low temperatures, typically at about 4° C. Following the filtration, the material is either frozen or directly aliquoted to lot sizes for large scale chromatographic processing.

F. Chromatography

Prior to the chromatographic separation, the material is in a concentrated state of not less than 2 grams per deciliter and not greater than 11 grams per deciliter. The chromatographic system includes pumps, a gradient generator, columns and detectors.

A typical pumping system comprises a diaphragm pumping system with a range of 1 to 5 liters per minute pumping capability. Such a system includes a Pulsafeeder 8480 stainless steel diaphragm pump or equivalent. For the feed system a smaller pump is used where the flow will range from 0.1 liters per minute to 1.5 liters per minute. This pump is typically a smaller volume pump and would be of a tubular diaphragm design. A typical pump for this operation is a Pulsafeeder 7120. To configure the chromatographic system such that it operates properly it is required that two large systems are assembled so that one would be used as the operating system for chromatographing the material while the other system is used for flushing, cleaning and regeneration of the column.

A solvent composition generation system has been fabricated and is comprised of flow control valves that deliver to the applicable pumping system a proportional amount of two fluids generating a fluid composition gradient over time of a specific ionic strength. Ionic interaction is used to effect an ion exchange chromatographic separation on the column system. Fabrication of this or equivalent systems is within the skill of the art.

A typical flow control valve is a Baumann flow control valve, which has been programmed to operate using a standard programmable controller, for example a Texas Instrument 530 programmable controller. All piping and tubing to the system is of sanitary nature and made of 316L tubing approximately $\frac{1}{2}$" to 1" in diameter. The feed system through the gradient generator and through the pump are presented to a separation segment or column as is known in the art.

The column is typically made from stainless pipe. The stainless pipe can be interconnected with tubing of $\frac{1}{2}$" diameter, such that it will comprise one long column for effecting a separation. The pipe or column is typically lined with teflon to give compliance to the internal surface which is helpful in effecting packing of the media internal to the column system.

The chromatographic system effluent can be monitored by a splitting of the stream and passing that small representative amount through a refractive index detector like a model R401 from Waters Associates or an ultraviolet detector, typically a 441 Waters Associates model number. These systems can be used to monitor the effluent stream from the column to detect the point at which the protein of interest is being eluted.

Once all parameters have been established and guidelines have been set, there is no need for a detector in the system and fraction collection may be achieved through simple time elution profiles.

These materials may be either fabricated or purchased from various suppliers of industrial grade piping and tubing. The column is fabricated to achieve uniform distribution of sample being presented to the top of the column and, in conjunction with that, uniform sample collection from the effluent of the column. The length to diameter ratio is significant in that creating a column that is too long or too short will significantly affect the efficiency of the separation and equilibration for doing the ion exchange.

The column is comprised of separation media which allows for some irreversible adsorption of phospholipids (irreversible in the simple operation mode) and a discrete ion exchange separation using a specified gradient elution pattern of solvent. The separation media comprise particles of silica gel of from about 50 to 150 microns in size; the flow across this material is in the range of about 2.5 liters per minute.

The silica gel is of an average pore size of 300 angstrom units, as measured by BET nitrogen absorption. This silica gel is available from various manufacturers i.e., W. R. Grace Davison Chemical Co. This gel is the preferred substrate on which to build the derivatized surface which gives the functionalized property for separation of the hemoglobin solution.

To produce the separation media, it is necessary to derivatize the silica surface first with a special silane which creates a diol chemical type surface on the silica surface. This diol can be typically achieved by creating a glycidoxypropyltrimethoxysilane coating to the surface, with techniques which are well known in the field of chromatography, typically by suspending the silica and the silane in a vessel which has been partially diluted with water. The reaction is a water bas reaction and this polymer will coat onto the surface of the silica. This reaction to coat the silica requires a 20 hour reaction time at approx. 70° C. Once this coating has been achieved on the silica, the material may be simply washed by a series of methanol and acetone washes to create a clean permanently bonded, diol coated silica. The material is then dryed and prepared for the second step or series of steps where different monomers are coated onto the surface and the surface will be derivatized to have a quaternary amine type surface property for doing or preforming the specific kind of ion exchange separation. The organic stationary phase is a thin skin of cross-linked polymer. The cross-linked polymer that is put onto the surface is built up from two different hydrophilic vinyl monomers. For example, one may use a monomer such as n-methyl/alacrylamide in 48% water solution (Silar Labs), and methylamdiopropyltrimethylamonium/chloride.

The two monomers have various capabilities; one monomer will copolymerize with another functional monomer, i.e., one having the ion exchange or absorption properties desired. It will cross-link with other polymer chains and anchor the cross-linked polymer to the silica surface.

The specific monomers chosen for this purpose have a vinyl functionality and a reactive groups that react in such a way that they can react with each other, forming the bridges that are necessary to coat to the surface and the coating of a stationary phase consisting of an amine functional group, thereby producing an ion exchange capability in the desired range.

Once these two monomers have been suspended in the aqueous solution, as well as with a methanol solution of the silica, the suspension solution is evaporated away leaving the monomers coated onto and into the silica gel. At this stage the mixture is resuspended in a new solution which also includes a radical initiation system, such as a Dupont product, Vazo 64. To initiate the reaction, the reaction mixture is heated to the point where it must be maintained at 70°-75° C., no higher and no lower.

At this temperature the reaction proceeds and the polymer is coated onto and bonded to surface, including the functional groups that produce the surface property used in the chromatographic media. When the reaction has been completed, it is necessary to remove unreacted monomer with a series of washes with several solvents, such as acetone and methanol. Following the completion of all these washes the material is dried and ready for use.

A typical column diameter is 6" and a typical column length is 2 feet. However, suitable variations are within the skill of the art. The maximum operating pressure is 500 psi. The injection is made by pumping the solution onto the column, typically at a rate of liter per minute for approximately 1 minute, then injection is terminated. Therefore, the load factor is no greater than 1 liter of material at 7 grams per deciliter. At the completion of loading the hemoglobin solution, an isocratic flow of buffer (e.g. tris buffer at pH 8.9 to 9.0) is applied to the column and continues to flow through the column until such time as the gradient or variable composition flow is started. The buffer, as the primary eluant, is then diluted over time. Typically, the eluant is made up from a Tris buffer base solution which is made in a concentration of 1.8 grams per liter Tris with a pH of about 8.6–9.2. The temperature range for elution is about 3°–10° C. These ranges are significant since changing the temperature range also changes the pH of the elution solution. The secondary solution for eluting the material of interest may be prepared using a solution of Tris buffer, highly purified in the same manner as the previous buffer. In addition, this buffer also contains salt to a 1 molar concentration. This solution is also pH adjusted to be identical to the original pH solution, which is in the range of 8.6 to 9.2. Release of phospholipids takes place prior to the elution of the hemoglobin, with endotoxins eluting after the hemoglobin peak of interest has been collected.

The chromatographic selection technique is done by UV absorption, refractive index, typically using equipment as described above, or visible observation of the effluent stream. Typically, the first portion of the eluting hemoglobin is discarded to waste; then the collection of effluent begins and continues until the peak or the response has been reduced to 20% to 10% of its peak amplitude. This constitutes the fraction to be collected and the fraction of interest for purification. If the collection point runs beyond the appropriate retention time, then other proteins and/or endotoxins may be collected and the product may be rendered unusable. Similarly, if collected before a peak retention time, the material may contain unacceptable levels of endotoxins. The phospholipid count and extraneous sub-components of hemoglobin are discarded, both the pre-retention peaks and the post-retained peaks. This collection process allows intermediate product material which has been diluted approximately 40 to 1, in a pH range of 8.9 to 9.0.

In this pH range it is necessary to concentrate the material rapidly. In this dilute state, the appearance and formation of methemoglobin occurs at a rapid rate. To effect this concentration, a membrane of 10,000 mW or less can be used. Either plate and frame tangential flow or hollow-fiber flow sytems are acceptable. Typical systems include a Millipore Pellicon cassette. When concentration levels of 7 to 10 grams per deciliter are achieved and a methemoglobin level of less than 1.5% are achieved, the fractions are collected for long-term storage. At this point the material may also be transported into a reactor system for the subsequent polymerization reaction.

Following the collection in the chromatographic system, the chromatographic column undergoes a sequence of washes to prepare it for a second loading of unpurified material. If this column preparation is not performed, various subcomponents and contaminants will elute and render subsequent runs invalid. Typically, the wash is accomplished by using a 100% pyrogen-free 0.5-1.0 molar NaCl wash for a period of at least 5 minutes, or 3 column volumes, and no more than 10 minutes, or 6 column volumes. At the completion of the buffer gradient and salt flush, the fluid phase is returned to initial conditions of 100% tris buffer which is 0.18 grams per liter of tris buffer, and pH is adjusted to approximately 8.9±0.1 for the hemoglobin elution process. Although ranges of the hemoglobin pH have been studied, the 8.9-9 pH range of the chromatographic system yields the highest and best isolation of a pure hemoglobin analogue. At lower ranges (8.6-8.4), hemoglobin is eluted in a pure state but the loadability of material onto the separation material is drastically decreased. At pH levels of 9.5-11, the formation of methemoglobin occurs at a rate which makes it untenable to maintain low methemoglobin levels. Further, there is the potential for cross-contamination. Over a period of 2 hours the methemoglobin level may increase 5% at this higher pH range. The material eluting from the column is a hemoglobin solution which is substantially free of other proteins, endotoxins, and phospholipids. This material has utility in its own right as an intermediate product in the production of a cross-linked, substantially endotoxin free, substantially phospholipid-free semi-synthetic blood substitute.

Long term storage of hemoglobin solution after concentration with sodium chloride and tris buffer has been carried out for periods of as short as 1 day and as long as 6 months. The results have shown no product degradation or increase in the methemoglobin level if the product is maintained at −20° C. The solution, however, upon thawing over a 2 to 24 hour period, may exhibit an increase in methemoglobin. If left in an unfrozen state, the methemoglobin level will continue to rise. In other studies where material had low pH (pH 7 and below) the methemoglobin level increase is dramatic, i.e., a 10 percentage point increase within 3 hours.

The hemoglobin solution typically has the following characteristics:

| HEMOGLOBIN SOLUTION SPECIFICATIONS | |
|---|---|
| Hemoglobin g/dl | 7-15 |
| Oxyhemoglobin | 90-100% |
| Carboxyhemoglobin | 0-2% |
| Methemoglobin | 0-10% |
| pH | 6.5-9.0 |
| Endotoxin EU/ml | <0.01 |
| Molecular weight daltons | 68,000 |
| Phospholipids | <1 nanomole/ml |
| TLC Plat iodine developed - clear | |
| Amino Acid Analysis | No foreign protein amino acids |
| N-Terminal sequencing | 98%+ conforms to Bovine hemoglobin sequence |
| Page Gel | Single Band? (no virus contamination) |
| Salt concentrations may vary | |
| High performance chromatography | 99.9%+ hemoglobin protein |

When material has been either specifically allocated for polymerization reaction or has been thawed from the frozen state, it is introduced into a sterile pyrogen-free reactor having impeller blades positioned to effect rapid mixing and high shear. (A typical apparatus is a 3 liter Applicon fermenter with a flat bladed impeller positioned one inch from the bottom of the reactor and with 5 one-half inch baffles positioned about the reactor. This is necessary to prevent large polymer formation when the cross-linking agent is added.) The hemoglobin solution added to the reactor is put on a recirculation system and the hemoglobin solution is withdrawn from the reactor and passed across an exclusion membrane, typically a 10,000 mw exclusion filter, and returned to the reactor in a low $O_2$ environment. (The reactor may be blanketed with an inert gas, i.e. argon.) This last procedure is accomplished by drawing a vacuum on the reactor and placing an argon blanket on the liquid in this reactor. Extreme caution is taken to eliminate introduction of bacteria at this point; the material is pyrogen-free, exhibiting no endotoxins by LAL analysis.

A sterile pyrogen-free buffer (pH 8.9-9.-1) is then added to the reactor through a depyrogenating membrane filter, typically a 10,000 molecule weight filter. Simultaneously a 10,000 mw concentration loop is cycled to balance the volume of introduced fluid and the exiting fluid from the reactor system.

The reaction buffer which is being used to neutralize the high pH is a physiologic composition of sodium, chloride, and potassium, with typical values of 120 milliequivalents sodium, 120 milliequivalents chloride and 4 milliequivalents potassium. The pH of the solution is adjusted with HCl and tris base to a pH of about 4.7 to 5.2. If the pH is too low during the pH reducing process, large amounts of methemoglobin form at the point of introduction of the neutralizing acid solution. The filtration process is maintained until the pH has dropped to a range of about 7.4 to 8.0 pH units in the reactor. At this time the introduction is terminated and the introduction of the cross-linking solution is made.

Suitable cross-linking agents are disclosed in U.S. Pat. No. 4,001,200 to Bonsen et al., incorporated by reference herein. The preferred class of cross-linking agents are those having aldehyde functionality, most preferably, dialdehydes, with glutaraldehye being the cross-linking agent of choice.

Where glutaraldehyde is used, the glutaraldehyde is added, typically at a. rate of about 100 milliliters per hour. The glutaraldehyde solution is typically prepared by thawing a high purity specification glutaraldehyde (stored at −20° C. to 4° C.) in a short, typically 2-5 minute, time frame. This solution, which preferably has about a 25% concentration of glutaraldehyde, is then added to pyrogen-free water, the proportions of which make up a solution which is preferably about 5 milliliters of a 25% solution diluted into 100 milliliters of pyrogen-free water. The solution is added at the rate specified above to the reactor and reaction mixture.

The monitoring of cross-linking solution and its effects on cross-linking (polymerization) is done by gel permeation chromatography. The gel permeation chromatography requires the use of a 300 Angstrom pore size hydrophilic packing material column with resolution capability of over 24,000 plates per meter. A typical column is available from Waters Associates; a typical packing material is Waters Protein Pak 300SW. The eluting chromatogram as recorded is integrated over the time of peak elution and quantitated against the starting material. Preferably, a cross-linking percentage of 50% to 70% is achieved. This number is determined by the percentage of material eluting from the column which is less than 600,000 molecular weight (Daltons) and greater than 68,000 molecular weight (Daltons).

H. Membrane Concentration

Once greater than 50–55% cross-linking, as calculated by gel permeation chromatography, has been achieved, the solution is ready for 100,000 molecular weight membrane concentration. During this membrane filtration the tangential flow of the reaction mixture is passed over the membrane with a permeation of material which is 68,000 or less through the membrane system. This is performed until about a 25% reduction in fluid has been achieved.

At the point when cross-linking is deemed to be complete, a quenching solution, i.e., a solution of pyrogen-free lysine, pH 7, is added. The concentration of the lysine solution is 1 gram per liter. This lysine solution is added to quench the polymerization reaction of glutaraldehyde with hemoglobin and to complex with excess glutaraldehyde. It is also believed that this material will fix to unpolymerized glutaraldehyde bound to hemoglobin molecules. At the completion of this addition, molecular weight distribution is determined and found to have been stabilized as measured by gel permeation chromatography. Filtration is then started to remove excess lysine, excess glutaraldehyde and any other molecular weight species which is below 100,000 M.W.

The gel permeation chromatogram of the initial non-cross-linked hemoglobin solution exhibits molecular weight sizes from 16,000 to 68,000 Daltons, with the largest amount at 68,000 Daltons. After filtration, there is some, not more than 50%, 68,000 Dalton hemoglobin and the appearance of material under 68,000 Dalton molecular weight is not detectable. Filtration of the material after cross-linking also provides opportunity to balance the electrolytes and pH of the solution and thereby give a balanced physiologic solution for injection.

At the completion of this filtration process the material is removed from the system and bagged ready for freezing. At the completion of all processes and during the bagging, a sample of material is withdrawn for testing.

II. THE PRODUCT

Typically, the product has the following characteristics. The molecular weight distribution of the material has greater than 90% of the material in the range of 68,000 Daltons to 500,000 Daltons. Osmolarity as measured by freezing point depression is typically from 220 to 320 milliosmoles per liter of solution. The electrophoretic pattern exhibited on gel electrophoresis shows bands in 68,000 to 500,000 molecular weight range. The final hemoglobin content can be adjusted to 5 to 25, preferably 9 to 13 grams per deciliter and the methemoglobin level is under 20%, preferably under 10%. The ion concentrations of sodium chloride and potassium are nontoxic to the animal or to the species to be tested. Thin layer chromatography developed for the detection of phospholipids exhibit a clear plate upon developing by iodine staining. Phospholipids as determined by phosphoric acid reduction are non-detectable, with less than one nanomole per milliliter as the limit of detection. Gas chromatography is used as a quantitative measure for free glutaraldehyde. With detection of 1 part per million by gas chromatography as the limit, no glutaraldehyde may be detected. No protein other than hemoglobin is present as determined by gel chromatography and iso-electric focusing techniques.

The solution generally has less than 0.01 endotoxin units per ml as measured by LAL (limulus amoebocytic lysate) assay with a 0.01 to 0.1 sensitivity scale, and is pyrogen-free by all testing. Rabbit studies have been performed on this material which exhibits the same characteristics as would be exhibited by a pyrogen free material in that no fever is exhibited by the rabbits. This material does not produce any abnormal endotoxin response and other factors in the rabbits being tested as it related to hemorrhagic conditions done on a control group of rabbits which were then supplied with a pure plasma fraction of ⅓ volume. It should be noted that in all cases, there was some elevated levels of enzymes and some histopathology that demonstrated changes in the organs. Most of these changes however, were deemed to be reversible and were, as mentioned earlier, similar to those found due to hemorrhagic conditions and replacement by a pure plasma protein fraction. This can be translated to a lack of endotoxin response and other factors in higher animals. The purity as monitored by high performance liquid chromatography using an ion exchange capacity for separation exhibits four discrete peaks which upon quantitation are consistent between batches regardless of the molecular weight distribution characterized by gel permeation chromatography. The substance produced exhibits life sustaining capabilities in oxygen transport as demonstrated by $P_{50}$ values of 20 to 28 mm of mercury. Further, importantly, the hemoglobin solutions of this invention demonstrate less clinically significant vasoconstrictive properties than those demonstrated by other prior art cross-linked hemoglobin solutions. The material further exhibits properties of increased cellular appearance of red blood cells in various mammalian species, and does not cause any of the following abnormal and detrimental chemical and physiologic functions in vivo: (1) does not activate complement; (2) does not cause hemorrhagic disorders; (3) does not cause abnormal platelet function or aggregation; (4) does not cause abnormal prothrombin times (PT); (5) does not cause abnormal partial thromboplastin times; (6) does not interfere with blood typing or cross-matching; (7) is non-toxic to the kidneys in 3.5 grams per kilogram per body weight or 8 grams per deciliter circulating blood volume; (8) exhibits circulating persistence of at least seven days; and (9) acts as a stimulus to accelerated erythropoiesis. The material is typically as characterized in the Table below.

| CHARACTERIZATION OF TYPICAL BLOOD SUBSTITUTE OF THIS INVENTION | |
|---|---|
| STERILITY | Sterile by standard culture technique |
| NON-DETECTABLE ENDOTOXIN LEVEL | <0.01 EU/ml sample when tested by LAL and compared against standard curve that ranges in sensitivity from 0.01 EU/ml to 0.125 EU/ml. |
| BAG CONTENTS | Na 120 ± 20 milliequivalent Cl 115 ± 20 milliequivalent K 4.0 ± 1 milliequivalent Hemoglobin 11 grams ± 2 per deciliter Lysine < 1 gram/liter Glutaraldehyde - none detectable Tris <1.5 gram/liter Pyrogen Free H2O volume - 450–500 ml Met Hemoglobin < 10% Phospholipid < 1 nanomole/ml Hemoglobin molecular weight distribution: % greater than 68,000 - at least 50% % greater than 500,000 - 8% ± 2% |

| CHARACTERIZATION OF TYPICAL BLOOD SUBSTITUTE OF THIS INVENTION -continued | |
|---|---|
| | Osmolarity by freezing point depression 220-320 milliosmoles per liter of solution |
| CONTAINER | Fenwal Bag Code 4R2023 600 ml sterile, nonpyrogenic fluid path Supplied by Fenwal Laboratories |
| STABILITY | −20° C. no change for greater than 8 months 4° C. 5 days with methemoglobin level under 10% |

III. UTILITY

The blood substitute of the present invention may be utilized in a manner similar to the suggested prior art blood substitutes and blood expanders. Thus the blood substitute may be used for replacing blood lost by acute hemorrhage, to replace blood loss occurring during surgical operations, in resuscitation procedures after accidental blood loss, for supplying oxygen, and generally to maintain blood volume in related conditions. As a plasma expander, the blood substitute may be utilized in volume deficiency shock, an alleviant in anaphylactic and allergic shock, for replacing plasma lost after burns, and as a result of diarrhea.

The blood substitute of the present invention may be utilized as such for all mammalian species, but is particularly useful in the treatment of humans. The blood substitute of the present invention is miscible with recipient blood and its components, is substantially non-toxic, non-antigenic, non-pyrogenic, and, especially, substantially free of endotoxins and other cell-bound and cell-free proteins. Its colloid-oncotic properties make the product especially useful for maintaining the level of the blood and plasma in the management of disease states as well. Further, the material is extremely valuable in that it may be used without an accompanying risk of transmission of disease. Further, it is believed that the blood substitute of the present invention is devoid of the immunologic problems that are associated with the administration of whole blood, and does not cause any of the following abnormal and detrimental chemical and physiologic functions in vivo: (1) does not activate complement; (2) does not cause hemorrhagic disorders; (3) does not cause abnormal platelet function or aggregation; (4) does not cause abnormal prothrombin times (PT); (5) does not cause abnormal partial thromboplastin times; (6) does not interfere with blood typing or cross-matching; (7) is non-toxic to the kidneys in 3.5 grams per kilogram per body weight or 8 grams per deciliter circulating blood volume; 8) exhibits circulating persistence of at least seven days; and (9) acts as a stimulus to accelerated erythropoiesis. The blood substitute of the present invention may be administered using techniques of administration which are conventional in the art, as disclosed in *Blood Transfusion*, by Hustis.

As a blood expander, the blood substitute of the present invention may be mixed with water-soluble physiologically acceptable polymeric plasma substitutes such as polyethylene oxide, polyacrylamide, polyvinyl pyrrolidone, polyvinyl alcohol, and ethylene oxide-propylene glycol condensate. The material may also be mixed with colloidal plasma-like substitutes and blood plasma expanders such as linear polysaccharides, including dextrans having a molecular weight of 40,000 to 70,000, gum arabic pectins, balanced fluid gelatin, and hydroxyethyl starch.

Additionally, the blood substitute of the present invention maybe used as an artifical oxygen exchange solution in conventional oxygenators. When used for assisting the circulation in ill patients, oxygenators are widely used to mechanically oxygenate venous blood extracorporeally, utilizing one or more pumps for maintaining circulation and for perfusion of oxygen by the exchange of gases between blood in an isolated vascular bed and oxygen across an oxygenation membrane.

EXAMPLES

EXAMPLE I

THE BLOOD PRODUCTION PROCESS

In the following Example, the equipment identified in parenthesis is further identified in the reference list which follows. FIGS. 1A-1H are a flow sheet for the process of this Example, with the equipment reference numbers of the Example corresponding to the Figure reference numbers.

A. Blood Collection

The starting point was approximately 5 gallons of individual collection of erythrocyte (red cells) source, from slaughtered cows. Because of its ready availability the bovine blood obtained from slaughter houses is the preferred erythrocyte source.

Collection trochars were used to extract the blood in a sterile manner; the animal hide is cut, peeled back and the trochars then inserted in the animals major vessels close to the heart. The introduction of bacteria was avoided and the maintenance of pyrogen-free or low-pyrogen level material was accomplished using individual containers of 25 liters that were precharged with depyrogenated sodium citrate as anti-coagulant (0.5 liters). The collected blood was capped off immediately to avoid exposure to the environment. Upon completion of the collection process, the material was chilled to about 4° C. to limit bacterial growth. There was no pooling of blood from different cows at this time. The blood was checked for pyrogens and sterility to ensure that (1) no one cow was sick or 2) that no contamination occurred during collection. The blood was transported in a refrigerated condition from the slaughter house to the process plant.

B. Red Cell Separation

Blood was pumped using Feed Pump (P-301) from collection containers at 2.5 to 6 liters per minute, to the Separation Centrifuge (CT-301) which was run at 15,000 to 18,000 rpm. The effluent from the centrifuge (separated red cells) was collected under sterile conditions in a 114 liter Dilution Tank (T-301). At this point the effluent was pooled and was no longer treated on an individual animal basis. Sterile nitrogen was applied at positive pressure to the centrifuge to exclude bacteria.

C. Red Cell Clarification

The red cells were diluted in Dilution Tank (T-301) using Water-For-Injection (WFI) which had been maintained at 4° C. The red cells were pumped by the Clarification Feed Pump (P-302) at less than 0.5 liters per minute from the Dilution Tank (T-301) to the Clarification Centrifuge (CT-302) which was run at 15,000 to 18,000 rpm. This clarification step resulted in the separation of all cell debris from the liberated hemoglobin solution which flowed by gravity to the Serile Holding Tank (T-302).

D. Microporous Filtration

The hemoglobin was pumped from the Sterile Holding Tank (T-302) by the Stage I Microfilter Feed Pump (P-401) at 5 liters per minute through the Stage I Microfilter (F-401) (0.45 micron). The retentate from the filter was recycled to the Sterile Holding Tank (T-302). The filtrate was pumped at 0.5 liters per minute by the Stage I Microfiltrate Pump (P-402) into the Stage I Microfiltrate Tank (T-402). Tank T-402 used in this microporous filtration stage was a glass vessel of 100 liter capacity and is equipped with Water-For-Injection (WFI) and Caustic flushing connections, with sterile vent filters. The microporous filters are of plate and frame construction (such as a Millipore Pellicon Cassette type) and were operated such that the average trans-membrane pressure (ATP) was carefully maintained to between 1 and 2 pounds per square inch. While the tangential flow of the material across the membrane was 2 to 5 liters per minute, the flux through the membrane was on the order of 0.1 to 0.2 liters per minute. This operational rate was maintained to eliminate cellular debris from building up on the membrane. When the concentration of the solution tangential to the membrane decreased to less than 10% of the initial solution, the remaining solution was discarded. (Alternatively, it is re-diluted with Water-For-Injection to achieve a high yield of hemoglobin from the system.) The solution was now ready for the molecular separations which followed.

E. Ultrafiltration

Hemoglobin was pumped from the Stage I Microfiltrate Tank (T-402) through 100,000 molecular weight Stage I Ultrafilters (F-501A & B) using the Stage I Ultrafilter Feed Pump (P-501). The retentate from the filters was recycled to the Microfiltrate Tank (T-402) and the filtrate was forwarded to the Stage I Ultrafiltrate Tank (T-501). The flow rate on the retentate side was 5 liters per minute. The filtrate flow rate was 0.2 liters per minute. Hemoglobin was then pumped from the Stage I Ultrafiltrate Tank (T-501) using the Stage II Ultrafilter Feed Pump (P-502) through the Stage II (30,000 D) Ultrafilters (F-502A & B). The retentate either recycled to the Stage I Ultrafiltrate Tank (T-501) or forwarded to the Stage II Ultrafiltrate Tank (T-502). The filtrate was sent to waste. The tanks were glass vessels of 100 liter capacity with sterile vent filters and are provided with connections for washing with WFI and Caustic. Connections were provided beneath the Stage II Ultrafiltrate Tank (T-502) for flushing the downstream system with WFI and Caustic.

F. Chromatography

The chromatography stage was automated based on a TI-530 software package. Key variables were protected by a lock ensuring repeatability of the process operations. Hemoglobin was pumped from the Stage II Ultrafiltrate Tank (T-502) and injected onto the GDT Columns (C-601A-D) at approximately 1 liter per minute for a period of I minute utilizing the GDT Feed Pump (P-601). After injection of hemoglobin the gradient or variable composition flow was started and injected onto the column using Gradient Pump (P-602). The composition of the gradient flow was established utilizing computer-controlled proportioning valves. Release of phospholipids took place prior to the elution of the hemoglobin, with endotoxins eluting after the hemoglobin peak of interest had been collected. Typically, the first portion of the eluting hemoglobin was discarded to waste. Then the collection of effluent was begun and continued until the peak or the response had been reduced to 20-10% of its peak amplitude. This constituted the fraction which was collected and the fraction of interest for purification. The gradient continued to run after hemoglobin collection to remove contaminants from the column prior to commencement of the wash cycle. The wash cycle through Wash Pump (P-603) was comprised of a wash utilizing firstly Tris/NaCl, then WFI, then Tris, which re-equilibrated the GDT column prior to the injection/elution cycle. The hemoglobin was collected in the GDT Tank (T-601), a 100 glass vessel, equipped with WFI and Caustic flushing connections and sterile vent filter. This solution is tetrameric in nature with over 99.9% in the 68,000 Dalton range as measured by native gel electrophoresis, and high performance liquid chromatography. The material is pyrogen-free and has a methemoglobin level below 2%. The concentration is 0.2 grams per deciliter before concentration and can be concentrated to 20 grams per deciliter.

G. Polymerization (Cross-linking) Reaction

Material was pumped from the GDT Tank (T-601) by the Stage I Cross-Link Pump (P-803) through the 10,000 molecular weight Stage I Cross-Link Filters. The retentate was recycled to the DGT Tank (T-601). The filtrate was sent to waste. This step was continued until a concentration of 7 to 10 grams per deciliter was obtained and methemoglobin level was less than 1.5%. This material was bagged and frozen or pumped directly by the Stage II Fermenter Feed Pump (P-904) to the Stage II Cross-Link Fermenter (FR-902). Frozen material may be thawed and fed by gravity directly to the fermenter (FR-902).

The processed material was pumped by the Stage II Cross-Linked Pump (P-605) through 10,000 molecular weight Stage II Cross-Link Filter (F-904). The retentate was recycled to the Stage II Cross-Link Fermenter (FR-902). The filtrate was sent to waste. The inside of the fermenter was maintained in a low oxygen environment by drawing a vacuum and blanketing with argon. The reactor system volume was maintained constant by simultaneously adding a sterile pyrogen-free buffer (pH 8.9-9.1) to the reactor through a depyrogenating membrane filter. This buffer was comprised of sodium, chloride, and potassium. The pH is adjusted with HCl and Tris base. The cross-linking agent (glutaraldehyde) was then added to the reactor.

H. Membrane Concentration

Once greater than 50-55% cross-linking, as calculated by gel permeation chromatography, had been achieved, the material was pumped by the Stage II Cross-Link Pump (P-904) through the 100,000 molecular weight Stage II Cross-Link Filter (F-905). The retentate was recycled to the Stage II Cross-Link Fermenter (FR-902), until about a 25% reduction is fluid volume had been attained. Electrolytes and pH were adjusted during the filtration stage to give a balanced physiologic solution for injection.

The material was then flowed by gravity to the bag filling machine. Product was bagged for freezer storage. Analysis of three separate batches of material produced by the above process, but eliminating optional step E produced cross-linked hemoglobin solutions having the properties as set forth in the "RESULTS" section of Example IV.

| REFERENCE LIST | |
|---|---|
| P-301 | ALBIN SLP 107 P51 B1 Sanitary Lobe-Rotary Pump |
| P-302 | Same as P-301 |
| P-402 | Same as P-301 |
| P-403 | Cole Parmer Masterflex Model 7019 Peristaltic Pump |
| P-501 | Same as P-301 |
| P-502 | Same as P-301 |
| P-601 | Same as P-301 |
| P-602 | Same as P-301 |
| P-603 | Same as P-301 |
| P-905 | Albin SLP 110 P51 B1 Sanitary Lobe-Rotary Pump |
| T-301 | 25 Gallon 316L Stainless Steel, Electro-Polished Interior Fab. by Thermo Electron Wisconsin, Inc. |
| T-302 | Same as T-301 |
| T-401 | O-I/Schott 100L Cylindrical Glass Vessel (GER 100) |
| T-501 | Same as P-401 |
| T-502 | Same as P-401 |
| T-601 | Same as P-401 |
| CT-301 | Sharples Model A-16 Type M-3500-520 2HHY CT-302 SAME AS CT-301 |
| F-401 | Stainless steel housing with sanitary pipe connections, fitted with millipore 5 sq. ft. filtration cassettes |
| F-402 | Same as F-401 |
| F-501A/501B | Same as F-401 |
| F-502A/502B | Same as F-401 |
| F-904 | Same as F-401 |
| F-905 | same as F-401 |
| C-601A-D | Resistoflex 6" stainless steel TFE lined pipe and flanges |
| FR-902 | 3 liter applicon fermenter (H/D = 2). Agitation: 2-6 blade paddle impellors (1.5 cm × 1 cm paddles) 3 cm and 14 cm from the tank bottom, and 4 baffles. |
| Bag Filling Machine | Model F-400-X Table Top Filling Machine, Cozzi Machine Company. |

EXAMPLE II

MOLECULAR WEIGHT DISTRIBUTION

This study was undertaken to determine molecular weight distribution of final product. Hemoglobin particles with M.W. more than 1,000,000 might cause some clinical problems in human and animals. One ul of final product (80 ug of protein) was diluted by 50, and this 50 ul was injected into Hewlett-Packard HPLC System. Water Data 740 Module Station was used to integrate results.

Since 1980 the classical gel filtration technique employing soft and semirigid organic gels for protein characterization and purification has received progressively greater competition from high-performance size-exclusion chromatography (HPSEC). The breakthrough of HPSEC is associated with the development of highly efficient buffer-compatible columns operating at elevated back pressure. The columns are packed with rigid hydrophilic porous silica gel particles of pre-determined pore size distribution and a derivatized protein-compatible surface. The proteins elute in the sequence of decreasing molecule weight and size.

Four pyrogen free batches of material with Hb concentrations below were used in the testing:

| Batch No. | Hb | MET Hb |
|---|---|---|
| 2261 | 10.3 | 3.4 |
| 2271 | 10.4 | 3.8 |
| 2311 | 11.3 | 7.2 |
| 2341 | 9.0 | 3.5 |

The following protein standards were used:
1. Blue dextran M.W. 2,000,000
2. Aldolase M.W. 158,000
3. Bovine Albumin M.W. 67,000
4. Ovalbumin - M.W. 45,000
5. Ferritin M.W. 540,000

TEST SYSTEM

Columns: One Protein-Pak, 300 sw, Waters Associates
Buffer: 0.1M k pH 7.8
Flow rate: 1 ml/min.
HPLC System: Hewlett Packard, 1090 liquid Chromatograph 280 nm Detector filter 740 Water Data Module Station

Statistical Analysis

Data was integrated using 740 Water Data Module Station. Before adding glutaraldehyde Hb solution (50 ul) was injected and retention time 9.699 was assumed for Hb with 68,000 M.W.

Retention time for blue dextran was around 4.8 min. Retention time for Hb solution 4.959 corresponds to M.W. of more than 1,000,000.

| Results | | | | |
|---|---|---|---|---|
| Distribution of Molecular Weight: Wave length: 254 Flow rate: 1 ml/min | | | | |
| Retention Time | 2261 | 2271 | 2311 | 2341 |
| 4.959 | 9.4% | 7.8% | 8.9% | 8.5% |
| 5.165 | 8.6% | 11.07% | 5.2% | 3.7% |
| 7.362 | 29.3% | 41.9% | 33.3% | 33.5% |
| 8.259 | 17.8% | 15.43% | 18.27% | 17.5% |
| 9.699 | 34.9% | 23.8% | 34.33% | 36.8% |

CONCLUSIONS

All 4 batches of material showed very consistent distribution of molecular weight from batch to batch. The best Batch was 2271 with 23.8% non-cross-linked material and 7.8% particles with high molecular weight.

The % of cross-linked material for the other 3 batches is:

| Batch No. | % Non-X-Linked | % Particles With High Molecular Weight |
|---|---|---|
| 2261 | 34.9 | 9.4 |
| 2311 | 34.3 | 8.9 |
| 2341 | 36.8 | 8.5 |

At the same time percent of particles with high molecular weight is 9.4%, 8.9% and 8.5%.

EXAMPLE III

ENDOTOXIN CONCENTRATION DETERMINATION

The detection of endotoxin concentration within a cross-linked blood ample was tested by using the Limulus Amebocyte Lysate (LAL) Assay test. The LAL has been obtained from the extracts of the amebocytes of the horseshoe crab. The sample was tested to be positive or negative and was determined as such against an end-point reaction made by a series of dilutions of a reference endotoxin. A standard regression curve was made from colorimetric readings from the above-mentioned dilutions and the endotoxin content was determined from the interpolation from the curve.

On Jan. 18, 1980 (38 FR 1404), the FDA announced that Limulus Amebocyte Lysate derived from amebocytes of the horseshoe crab is now a biologic product and can be used in place of rabbits. LAL has proved to be a sensitive indicator of bacterial endotoxin or pyrogens within the product. Because of its high sensitivity in detecting endotoxins, products can be prevented from being administered to humans which could cause fever, shock and death if found too high in pyrogens.

Test and Control Articles

Four polymerized blood samples were tested using LAL assay test and found to be less than 0.01 endotoxin units per ml.

| Batch No. | Eu/ml |
|---|---|
| 2261 | <0.01 |
| 2271 | <0.01 |
| 1311 | <0.01 |
| 2341 | <0.01 |

Materials:

1. Glass test tubes depyrogenated by baking in a 180° C. oven for no less than 4 hours, preferably 24 hours
2. Limulus Amebocyte Lysate, Lot #372, Spectrozyme substrate (Cape Code Associates)
3. Acetic acid - 50% solution, $H_2O$ used for injection, diluted sample of polymerized blood.

EXAMPLE IV

ACUTE TOXICITY DETERMINATION

Three batches of the blood substitute of the present invention (Hb-I, Hb-II and Hb-III) referred to as hemoglobin below, and human plasma protein fraction (PPF), in a controlled study, were used to replace one-third of estimated blood volume in 4 groups of 6 rabbits each.

This study was undertaken to evaluate the acute toxicity of the blood substitute of the present invention for intravenous administration in rabbits. The study is based in terms of (1) mortality, (2) morbidity, (3) pathophysiologic changes affecting the vital organs, (4) pathologic changes (gross), and (5) pathologic changes (microscopic). The study is designed to compare the effects of 3 batches of the blood substitute (Hb-I, Hb-II, and Hb-III) to those of human Plasma protein Fractions (PPF) following replacement of ⅓ estimated blood volume in 4 groups of rabbits.

EXPERIMENTAL MODEL

New Zealand male rabbits of 4.0 Kg body weight; sedated with chlorpromazine, 5 g/Kg body weight I.M.; restrained.
Instrumented with:
(a) urinary catheter
b) arterial line (one ear's artery)
(c) venous line (one ear's marginal vein)
d) needle-electrodes for ECG
(e) thermoprobe (subcutaneous)

| EXPERIMENTAL PROTOCOL |
|---|
| Sedation |
| Instrumentation |
| @ |
| $T_1$ (baseline) @ and * |
| Bleeding |
| Infusion of blood substitute |
| @ |
| $T_2$ (15 minutes post-infusion) @ and * |
| @ |
| @ |
| $T_3$ (1 hour post-infusion) @ and * |
| @ |
| @ |
| @ |
| @ |
| @ |
| @ |
| @ |
| @ |
| $T_4$ (3 hours post-infusion) @ and *; cannulae and electrodes removed; Animal returned to the cage |
| $T_5$ (24 hours post-infusion) @ and * necropsy |

@ = measurement of hemodynamic parameters
* = blood and urine samples

Anesthesia. The animals were sedated with chlorpromazine 0.5 g/kg body weight injected I.M., restrained in a metal rabbit-holder and allowed to spontaneously breathe room air. Body temperature was maintained by placing the animal on an electric heating pad.

Instrumentation. Plastic cannulae (22-gauge) were inserted into both ears' central arteries (one connected to a pressure transducer to monitor the arterial blood pressure and the other used for removal and sampling of arterial blood) and the ear veins for the infusion of hemoglobin solution. Needle electrodes were placed in the limbs to monitor the electrocardiogram. A catheter was inserted into the urinary bladder for the measurement of urinary output and the collection of urine samples. A temperature probe was inserted subcutaneously to monitor body temperature.

Procedure. Arterial blood was removed in the amount of 20 ml/kg body weight approximately ⅓ of estimated blood volume) and this amount was immediately replaced with an equal amount of hemoglobin solution. All blood subsequently removed for laboratory testing was replaced with hemoglobin, 1:1 v:v. The animal was closely observed for a period of 3 hours (time necessary for the completion of the pyrogenicity test). During this interval, additional doses of chlorpromazine were administered as necessary to maintain the animal sedated, and an intravenous infusion of 5% dextrose in ¼ normal saline was administered, 15 ml/Kg body weight/hour, to replace water losses.

Electrocardiogram, blood pressure and body temperature were monitored continuously and recorded at 15-minute intervals. Urinary output was recorded at 30-minute intervals. Blood samples were taken at baseline, and 15 minutes, 1 hour and 3 hours after completion of the hemoglobin infusion. All monitoring lines were then disconnected and the animal was returned to its cage, where it was allowed water "ad libitum". Additional blood samples were taken at 6, 12 and 24 hours, with the animal again restrained in the rabbit-holder and using the ear arteries. After 24 hours, the animal was killed with an overdose of pentobarbital and a complete necropsy was carried out. Special attention was paid to the possible presence of hemoglobin pigment in the body cavities, including the anterior chamber of the eye. Sections were taken of all organs for histologic examination.

The following tests were carried out on each blood sample:
1) Complete CBC, including platelet count (Coulter Counter),
2) PTT MLA 700); fibrinogen; fibrin split products
3) Electrolytes (sodium, potassium, chloride and bicarbonate) (ASTRA Apparatus),
4) Alakaline P-ase, LDH, SGOT and SGPT (ASTRA Apparatus)
5) BUN and creatinine (ASTRA Apparatus)
6) Osmolarity (Vapor pressure)
7) Plasma hemoglobin concentration (Benzidine)
8) Arterial Blood Gases (IL pH/Blood Gas Analyzer)
9) Total Hb, Oxy-Hb, CO-Hb, Met-Hb and 02 Content (IL 282 Co-oximeter)
10) $P_{50}$ (Aminco Hem-O-Scan)

Urine was tested for:
1) hemoglobin concentration (Benzidine)
2) creatinine (ASTRA Apparatus)
3) sodium and potassium (ASTRA Apparatus)

By the timed collection of urine and the determination of plasma and urine creatinine, a Creatinine Clearance Test was carried out at the 3-hour interval post-hemoglobin infusion.

The data will be tabulated as shown in the following tables.

Data Evaluation. The data obtained from the 6 animals in each group was tabulated as Mean Values ± Standard Errors. The statistical significance of changes related to time was evaluated by analysis of variance (Table III). Comparisons between the various groups of animals was made using Student's T-test for paired data (Table IV). The raw data for compiling Tables III and IV is presented in Tables I and II.

METHODS

(A) Mortality

(B) Morbidity

Attention was paid to the development of the following manifestations:
1=anaphylactic shock
2=seizures or development of neurologic deficits
3=bronchospasm or pulmonary edema (immediate effects)
4=fever
5=hemoglobinuria
6=hyphema
7=lack of normal activity
8=depression of normal functions (eating and drinking) at 24 hours

(C) Pathophysiologic changes

These changes were studied according to the following scheme:

1. Clinical observations:
   a. body weight
   b. body temperature
   c. heart rate
   d. arrhythmias
   e. blood pressure (systolic)
   f. blood pressure (diastolic)
   g. urinary output
2. Laboratory data reflecting respiratory function:
   a. arterial blood pH
   b. $PaO_2$
   c. $PaCO_2$
   d. $P_{50}$
3. Hematology (Coulter);
   a. hematocrit
   b. hemoglobin
   c. WBC
   d. platelets
4. Coagulation:
   a. fibrinogen
   b. fibrin split products
   c. P.T.
5. Liver function:
   a. total bilirubin
   b. SGOT
   c. LDH
   d. SGPT
6. Renal function:
   a. BUN
   b. serum creatinine
   c. serum electrolytes
   d. serum osmolality

(D) Gross Pathology

At necropsy, attention was focused on hemoglobin extravasation: into the anterior chamber of the eye, the pericardium, the pleurae and the peritoneum.

Heart, lungs, liver, spleen and kidneys were examined for gross signs of edema, congestion, hemorrhage and infarction.

(E) Histopathology

Section of heart, lungs, liver, spleen and kidneys were processed for, and examined by, light microscopy.

A method of grading the histopathologic changes was developed in order to perform a statistical analysis of the data.

The main change seen in the heart was represented by focal areas of myocardial contracture. Each focal area found on a transverse section of the left ventricle was assigned a 1+grade.

In the lungs, pathology was also patchy. The main changes were represented by interstitial edema and cell infiltration ("interstitial pneumonia"). Grading was carried out from an overall picture of tissue involvement, as well as from the severity of changes observed in each involved area, developing a scale of 1-to-4.

In the liver, the main alterations were represented by congestion and by centrolobular vacuolization. These changes were graded on a scale of 1-to-4 on the basis of both, the number of lobules involved and the extent of vacuolization starting from the centrolobular venule.

In the spleen, congestion was the main finding.

In the kidney, no glomerular alteration and no tubular necrosis or blockage by pigment casts was found. The main alteration was represented by a vacuolization of the tubular epithelium, starting at the subcapsular area and extending from there toward the corticomedullary junction. The degree of this extension was graded on a scale of 1-to-4.

STATISTICAL ANALYSIS

Analysis of the data was carried out using two tests:

(a) Analysis of variance to study changes occurring in each group of animals at various time intervals; and (b) Student's t-test for paired data to study the changes occurring at each time interval in the various groups of animals.

Results of statistical analyses performed are presented in Tables III and IV.

TABLE I

|  | T-1 [B.L.] M ± SD | T-2 [15 min.] M ± SD | T-3 [1 hr.] M ± SD | T-4 [3 hrs.] M ± SD | T-5 [24 hrs.] M ± SD |
|---|---|---|---|---|---|
| 1. BODY WEIGHT [gm] | | | | | |
| PPF | 4166 ± 262.4 | — | — | 4260 ± 309.8 | 4170 ± 292.0 |
| Hb I | 4350 ± 125.8 | — | — | 4510 ± 125.0 | 4366 ± 110.5 |
| Hb II | 4150 ± 236.2 | — | — | 4285 ± 226.8 | 4150 ± 211.9 |
| Hb III | 3966 ± 47.0 | — | — | 4092 ± 84.0 | 4014 ± 51.0 |
| 2. BODY TEMPERATURE [°C] | | | | | |
| PPF | 38.7 ± 0.42 | 38.5 ± 0.44 | 38.5 ± 0.46 | 38.5 ± 0.47 | 38.6 ± 0.45 |
| Hb I | 38.8 ± 0.38 | 38.8 ± 0.38 | 38.9 ± 0.46 | 38.9 ± 0.58 | 39.0 ± 0.58 |
| Hb II | 39.1 ± 0.09 | 38.8 ± 0.37 | 38.9 ± 0.63 | 38.9 ± 0.69 | 38.9 ± 0.18 |
| Hb III | 39.4 ± 0.40 | 39.0 ± 0.50 | 39.1 ± 0.46 | 38.9 ± 0.68 | 39.1 ± 0.71 |
| 3. HEART RATE [Beats/min] | | | | | |
| PPF | 220 ± 21.9 | 200 ± 13.20 | 195 ± 21.23* | 197 ± 16.43* | 198 ± 5.03* |
| Hb I | 230 ± 5.77 | 212 ± 8.49** | 218 ± 8.97*c | 225 ± 7.63b | 222 ± 12.13b |
| Hb II | 220 ± 17.71 | 200 ± 11.60 | 199 ± 15.60* | 203 ± 18.97 | 203 ± 9.42 |
| Hb III | 211 ± 24.00 | 190 ± 33.00 | 196 ± 33.00 | 213 ± 39.00b | 202 ± 10.00 |
| 4. BLOOD PRESSURE (SYSTOLIC) [mm Hg] | | | | | |
| PPF | 100 ± 6.32 | 95.8 ± 14.06 | 95 ± 10.00 | 96.7 ± 5.18 | 96 ± 4.18 |
| Hb I | 104.5 ± 14.8 | 113.3 ± 12.13c | 109.5 ± 10.22c | 108.3 ± 10.27c | 108.3 ± 10.27c |
| Hb II | 95.8 ± 5.33 | 111.6 ± 15.72*c | 105.8 ± 11.33 | 106.7 ± 12.13 | 105 ± 8.16 |
| Hb III | 97.3 ± 0.21 | 95.2 ± 7.00 | 102.3 ± 9.59 | 90.8 ± 7.86 | 88.3 ± 6.20* |
| 5. BLOOD PRESSURE (DIASTOLIC) [mm Hg] | | | | | |
| PPF | 60.8 ± 9.17 | 60.8 ± 14.63 | 60.8 ± 9.70 | 62.5 ± 6.89 | 65.0 ± 4.08 |
| Hb I | 70.8 ± 15.91 | 80.0 ± 14.71c | 77.5 ± 14.92c | 77.5 ± 13.96 | 74.2 ± 12.72 |
| Hb II | 60.0 ± 8.16 | 75.8 ± 15.11*c | 73.3 ± 11.05* | 70.8 ± 9.75 | 67.5 ± 6.92 |
| Hb III | 64.2 ± 3.43 | 69.2 ± 5.32 | 73.8 ± 7.53* | 63.3 ± 7.60 | 61.7 ± 6.20 |
| 6. URINARY OUTPUT [ml/30 min.] | | | | | |
| PPF | 2.60 ± 0.49 | 0.0 ± 0.00*** | 3.00 ± 0.61 | 3.10 ± 0.63 | 3.00 ± 0.53 |
| Hb I | 3.11 ± 0.29 | 0.0 ± 0.00* | 6.66 ± 1.72b | 5.66 ± 1.59c | 4.63 ± 0.96c |
| Hb II | 3.00 ± 0.57 | 0.0 ± 0.00*** | 5.30 ± 1.59*b | 5.10 ± 1.64* | 4.25 ± 1.46 |
| Hb III | 5.66 ± 1.99c | 6.50 ± 4.63*a | 10.80 ± 2.90a | 11.30 ± 4.20a | 5.40 ± 1.26b |
| 7. ARTERIAL BLOOD pH [UNITS] | | | | | |
| PPF | 7.33 ± 0.04 | 7.34 ± 0.05 | 7.33 ± 0.03 | 7.33 ± 0.33 | 7.39 ± 0.13 |
| Hb I | 7.43 ± 0.10 | 7.36 ± 0.13 | 7.37 ± 0.10 | 7.37 ± 0.10 | 7.38 ± 0.06 |
| Hb II | 7.36 ± 0.03 | 7.36 ± 0.03 | 7.34 ± 0.12 | 7.42 ± 0.11 | 7.36 ± 0.04 |
| Hb III | 7.28 ± 0.03 | 7.30 ± 0.02 | 7.28 ± 0.05 | 7.26 ± 0.06 | 7.31 ± 0.03 |
| 8. PaO$_2$ [mm Hg] | | | | | |
| PPF | 69.9 ± 8.29 | 70.8 ± 11.72 | 62.0 ± 4.67* | 59.2 ± 8.09* | 69.2 ± 5.88 |
| Hb I | 74.1 ± 16.7 | 67.5 ± 8.54 | 73.7 ± 10.2c | 71.5 ± 11.3c | 60.6 ± 7.78 |
| Hb II | 63.8 ± 2.12 | 69.2 ± 6.14 | 81.6 ± 9.66*b | 79.5 ± 5.88*a | 76.9 ± 13.0c |
| Hb III | 63.3 ± 12.2 | 76.3 ± 14.4 | 70.7 ± 7.30c | 88.1 ± 18.3*b | 69.9 ± 13.0c |
| 9. PaCO$_2$ [mm Hg] | | | | | |
| PPF | 29.8 ± 3.24 | 31.2 ± 2.77 | 33.7 ± 2.98* | 34.8 ± 2.11** | 31.9 ± 5.15 |
| Hb I | 29.8 ± 3.08 | 33.0 ± 5.27 | 34.4 ± 4.59* | 32.6 ± 5.33 | 32.5 ± 5.12 |
| Hb II | 28.8 ± 5.37 | 31.0 ± 1.89 | 31.9 ± 3.47 | 30.0 ± 4.30c | 31.2 ± 2.01 |
| Hb III | 32.8 ± 2.56 | 27.6 ± 0.62**c | 29.9 ± 2.50c | 33.0 ± 3.49 | 32.4 ± 1.45 |
| 10. BLOOD P$_{50}$ [mmHg] | | | | | |
| PPF | 34.0 ± 0.61 | 33.7 ± 1.75 | 33.8 ± 3.01 | 34.0 ± 1.80 | 34.0 ± 1.80 |
| Hb I | | | | | |
| Hb II | 33.7 ± 0.87 | 29.7 ± 0.63*b | 30.8 ± 0.47 | 32.7 ± 0.62 | 33.0 ± 1.41 |
| Hb III | 32.4 ± 1.45 | 27.7 ± 1.43*a | 29.5 ± 1.29b | 30.8 ± 1.24c | 31.6 ± 0.41c |
| 11. COLLOID OSMOTIC PRESSURE (COP) [mmHg] | | | | | |
| PPF | 18.2 ± 0.53 | 19.2 ± 0.06* | 19.3 ± 0.77* | 18.8 ± 0.60 | 18.3 ± 0.59 |
| Hb I | | | | | |
| Hb II | 17.9 ± 0.49 | 19.5 ± 0.55** | 19.5 ± 1.17* | 19.3 ± 1.21 | 18.5 ± 0.63 |
| Hb III | 17.5 ± 0.07 | 19.5 ± 0.77*** | 29.5 ± 1.29*** | 18.5 ± 0.59** | 17.9 ± 0.38* |
| 12. PLASMA Hb [g/dl] | | | | | |
| PPF | 0.00 ± 0.00 | 0.00 ± 0.00 | 0.00 ± 0.00 | 0.00 ± 0.00 | 0.00 ± 0.00 |
| Hb I | | | | | |
| Hb II | 0.00 ± 0.00 | 3.82 ± 0.71*a | 3.50 ± 0.68*a | 3.10 ± 0.40*a | 2.10 ± 0.51* |
| Hb III | 0.00 ± 0.00 | 3.16 ± 0.78*a | 2.70 ± 0.79*a | 2.60 ± 0.70*a | 2.10 ± 0.66 |
| 13. WBC [×10$^9$] | | | | | |
| PPF | 6.27 ± 2.13 | 6.48 ± 1.16 | 7.25 ± 2.15 | 6.58 ± 1.53 | 6.55 ± 1.20 |

TABLE I-continued

| | T-1 [B.L.]<br>M ± SD | T-2 [15 min.]<br>M ± SD | T-3 [1 hr.]<br>M ± SD | T-4 [3 hrs.]<br>M ± SD | T-5 [24 hrs.]<br>M ± SD |
|---|---|---|---|---|---|
| Hb I | 4.86 ± 0.85 | 3.56 ± 0.43*a | 5.70 ± 1.53 | 6.48 ± 2.11* | 8.60 ± 1.24** |
| Hb II | 4.88 ± 0.87 | 4.70 ± 1.94 | 5.05 ± 1.29 | 4.78 ± 0.69c | 6.22 ± 1.45 |
| Hb III | 5.83 ± 1.38 | 3.17 ± 0.84*a | 2.98 ± 1.06**b | 4.22 ± 2.38 | 11.50 ± 6.84 |
| 14. RBC [$\times 10^{12}$] | | | | | |
| PPF | 5.10 ± 0.42 | 3.75 ± 0.42*** | 3.90 ± 0.27*** | 3.80 ± 0.39*** | 3.79 ± 0.32** |
| Hb I | 4.86 ± 0.23 | 3.78 ± 0.30*** | 3.83 ± 0.30*** | 3.79 ± 0.33*** | 3.98 ± 0.24** |
| Hb II | 5.32 ± 0.33 | 3.86 ± 0.19*** | 3.86 ± 0.17*** | 3.87 ± 0.22*** | 4.18 ± 0.64** |
| Hb III | 5.49 ± 0.55 | 4.44 ± 0.33c | 4.47 ± 0.37c | 4.18 ± 0.63 | 3.87 ± 0.39 |
| 15. HEMOGLOBIN [g/dl] | | | | | |
| PPF | 11.6 ± 0.82 | 8.4 ± 0.93*** | 8.8 ± 0.59*** | 8.6 ± 0.72*** | 8.7 ± 0.72*** |
| Hb I | 11.3 ± 0.75 | 11.1 ± 0.30a | 11.2 ± 0.69a | 10.7 ± 0.42a | 11.1 ± 0.23a |
| Hb II | 11.6 ± 0.85 | 11.2 ± 0.68a | 11.0 ± 0.54a | 10.6 ± 0.30a | 10.2 ± 3.20a |
| HB III | 12.1 ± 1.25 | 12.1 ± 1.00a | 12.0 ± 0.96a | 11.3 ± 1.04a | 10.0 ± 0.91*a |
| 16. HEMATOCRIT [%] | | | | | |
| PPF | 33.7 ± 2.85 | 24.6 ± 2.77*** | 25.5 ± 1.77*** | 24.9 ± 2.01*** | 24.9 ± 1.98*** |
| Hb I | 32.9 ± 2.14 | 25.5 ± 2.32*** | 25.8 ± 1.64*** | 25.5 ± 1.44*** | 28.1 ± 2.01* |
| Hb II | 34.2 ± 2.23 | 24.7 ± 1.14*** | 24.8 ± 0.82*** | 24.8 ± 1.25*** | 26.8 ± 4.07** |
| Hb III | 35.4 ± 2.69 | 28.4 ± 2.24b | 28.5 ± 2.25c | 27.4 ± 2.30* | 25.3 ± 2.84* |
| 17. PLATELETS [$\times 10^9$] | | | | | |
| PPF | 388 ± 54.5 | 300 ± 45.6* | 336 ± 51.8** | 314 ± 39.8* | 376 ± 36.2 |
| Hb I | 363 ± 48.7 | 248 ± 18.7*c | 236 ± 43.5b | 256 ± 24.9**c | 367 ± 111.2 |
| Hb II | 411 ± 86.5 | 241 ± 70.9** | 263 ± 78.9** | 292 ± 69.8* | 350 ± 69.2 |
| Hb III | 461 ± 63.0 | 264 ± 111.0** | 281 ± 97.0** | 274 ± 71.0** | 402 ± 158.0 |
| 18. FIBRINOGEN [mg/dl] | | | | | |
| PPF | 226 ± 31.8 | 165 ± 19.7** | 180 ± 11.5** | 191 ± 21.5* | 334 ± 32.6*** |
| Hb I | 238 ± 35.3 | 147 ± 25.5* | 140 ± 23.8*b | 139 ± 25.7***b | 291 ± 112.7 |
| Hb II | 240 ± 83.4 | 142 ± 28.9* | 131 ± 28.2*b | 125 ± 19.3*b | 294 ± 96.3 |
| Hb III | 234 ± 39.0 | 152 ± 43.0* | 138 ± 38.0b | 126 ± 36.0b | 355 ± 149.0 |
| 19. FIBRIN SPLIT PROD. [mcg/ml] [0 = <10 mcg/ml, 1 = >10 <40 mcg/ml, 2 = >40 mcg/ml] | | | | | |
| PPF | 0.00 ± 0.0 | 0.00 ± 0.0 | 0.16 ± 0.37 | 0.00 ± 0.0 | 0.00 ± 0.0 |
| Hb I | 0.16 ± 0.37 | 1.0 ± 0.57*b | 1.16 ± 0.68*c | 1.16 ± 0.37b | 0.75 ± 0.42b |
| Hb II | 0.00 ± 0.0 | 0.50 ± 0.50*c | 0.66 ± 0.74 | 0.50 ± 0.50 | 0.50 ± 0.50 |
| Hb III | 0.00 ± 0.0 | 0.00 ± 0.0 | 0.00 ± 0.0 | 0.16 ± 0.37 | 0.16 ± 0.37 |
| 20. PROTHROMBIN TIME [sec] | | | | | |
| PPF | 10.8 ± 2.11 | 11.2 ± 1.64 | 9.25 ± 2.00 | 9.4 ± 1.00 | 8.0 ± 0.32* |
| Hb I | 10.7 ± 1.32 | 11.1 ± 2.33 | 11.5 ± 2.64 | 12.2 ± 2.72 | 10.0 ± 1.27c |
| Hb II | 9.6 ± 0.72 | 9.4 ± 0.51c | 10.6 ± 2.21 | 9.4 ± 0.36 | 8.4 ± 0.48* |
| Hb III | 10.1 ± 1.72 | 11.8 ± 2.52 | 11.2 ± 2.15 | 11.0 ± 1.36 | 9.3 ± 2.54 |
| 21. TOTAL BILIRUBIN [mg/dl] | | | | | |
| PPF | 0.33 ± 0.05 | 0.20 ± 0.08 | 0.23 ± 0.05 | 0.23 ± 0.09 | 0.27 ± 0.11 |
| Hb I | | | | | |
| Hb II | 0.17 ± 0.04 | 0.13 ± 0.04 | 0.33 ± 0.26 | 0.17 ± 0.09 | 0.63 ± 0.20 |
| Hb III | 0.18 ± 0.13 | 0.17 ± 0.10 | 0.28 ± 0.20 | 0.32 ± 0.26 | 0.42 ± 0.19* |
| 22. SGOT (AST) [Iu/L] | | | | | |
| PPF | 39.6 ± 4.96 | 38.0 ± 4.53* | 29.7 ± 5.85* | 30.0 ± 3.66* | 69.7 ± 7.49*** |
| Hb I | 28.3 ± 11.32 | 30.0 ± 8.16 | 35.0 ± 5.00 | 25.1 ± 8.37 | 108.3 ± 57.6* |
| Hb II | 39.5 ± 16.3 | 38.3 ± 2.35 | 36.6 ± 4.70 | 58.7 ± 18.7c | 38.0 ± 8.36a |
| Hb III | 41.8 ± 15.0 | 38.3 ± 8.40 | 37.5 ± 4.78 | 40.0 ± 7.10c | 493 ± 305.9**a |
| 23. LDH [Iu/L] | | | | | |
| PPF | 69.0 ± 12.0 | 50.8 ± 5.83** | 60.0 ± 14.0 | 52.6 ± 9.63* | 135.0 ± 35.5*** |
| Hb I | 66.0 ± 34.1 | 60.8 ± 19.2 | 78.0 ± 6.00c | 112 ± 32.9*b | 73.3 ± 33.1c |
| Hb II | 61.0 ± 39.3 | 69.6 ± 15.5 | 67.5 ± 10.2 | 70.6 ± 24.5 | 109.2 ± 17.9 |
| Hb III | 52.7 ± 12.3 | 46.0 ± 19.5 | 44.7 ± 81.0 | 58.0 ± 9.27 | 927.0 ± 477**c |
| 24. SGPT (ALT) [uI/L] | | | | | |
| PPF | 46.2 ± 8.67 | 31.5 ± 7.99* | 33.2 ± 8.82* | 32.5 ± 8.48* | 60.5 ± 5.44* |
| Hb I | 48.6 ± 9.92 | 43.3 ± 2.35 | 46.6 ± 2.35c | 41.0 ± 13.5 | 48.8 ± 16.8 |
| Hb II | 46.3 ± 20.2 | 48.8 ± 25.2 | 40.0 ± 4.08 | 39.0 ± 7.34 | 43.2 ± 23.1 |
| Hb III | 41.2 ± 11.6 | 43.6 ± 10.6 | 37.0 ± 9.27 | 41.2 ± 4.13 | 191.5 ± 119**c |
| 25. BUN [mg/dl] | | | | | |
| PPF | 16.2 ± 2.13 | 16.2 ± 3.37 | 14.5 ± 2.43 | 14.2 ± 2.40 | 13.5 ± 2.08 |
| Hb I | 21.0 ± 2.82c | 21.8 ± 2.88c | 21.5 ± 2.93c | 21.8 ± 3.33c | 20.6 ± 4.41b |
| Hb II | 22.5 ± 5.50c | 22.8 ± 5.39c | 22.3 ± 4.81c | 20.8 ± 5.07c | 21.0 ± 2.81b |
| Hb III | 17.0 ± 1.52 | 17.2 ± 1.67 | 17.3 ± 1.48c | 16.2 ± 1.34 | 20.7 ± 4.49b |
| 26. SERUM CREATININE [mg/dl] | | | | | |
| PPF | 1.25 ± 0.18 | 1.23 ± 0.18 | 1.05 ± 0.10 | 1.07 ± 1.16 | 1.10 ± 0.12 |
| Hb I | 1.43 ± 0.14 | 2.26 ± 1.05 | 1.85 ± 0.91c | 1.88 ± 0.44b | 1.84 ± 0.46c |
| Hb II | 1.50 ± 0.30 | 1.31 ± 0.65 | 1.24 ± 0.57 | 1.64 ± 0.31c | 1.32 ± 0.42 |
| Hb III | 1.38 ± 1.17 | 2.15 ± 1.13 | 2.32 ± 0.90c | 2.60 ± 1.35*c | 2.2 ± 0.42c |

TABLE I-continued

|  | T-1 [B.L.]<br>M ± SD | T-2 [15 min.]<br>M ± SD | T-3 [1 hr.]<br>M ± SD | T-4 [3 hrs.]<br>M ± SD | T-5 [24 hrs.]<br>M ± SD |
|---|---|---|---|---|---|
| 27. SERUM SODIUM [mEq/l] | | | | | |
| PPF | 137.0 ± 2.19 | 139.0 ± 2.86 | 140.5 ± 4.08 | 141.0 ± 4.31 | 145.0 ± 1.25*** |
| Hb I | 137.2 ± 2.26 | 134.8 ± 3.23c | 139.5 ± 10.7 | 136.6 ± 3.72 | 140.8 ± 4.31c |
| Hb II | 134.8 ± 2.11 | 131.3 ± 4.18c | 133.0 ± 1.73b | 135.5 ± 8.21 | 140.0 ± 4.05*c |
| Hb III | 130.0 ± 3.50c | 129.0 ± 5.10b | 128.6 ± 5.10a | 129.8 ± 4.00b | 138.0 ± 3.50*c |
| 28. SERUM POTASSIUM [mEq/l] | | | | | |
| PPF | 3.45 ± 0.26 | 3.30 ± 0.30 | 3.50 ± 0.27 | 3.27 ± 0.28 | 4.35 ± 0.35*** |
| Hb I | 3.71 ± 0.48 | 3.78 ± 0.35c | 4.23 ± 1.64 | 3.50 ± 0.43 | 3.84 ± 0.32 |
| Hb II | 3.61 ± 0.48 | 3.42 ± 0.34 | 3.45 ± 0.26 | 3.53 ± 0.39 | 4.32 ± 0.17* |
| Hb III | 3.60 ± 0.41 | 3.33 ± 0.43 | 3.15 ± 0.29 | 3.23 ± 0.27 | 3.60 ± 0.79 |
| 29. SERUM CHLORIDE [mEq/l] | | | | | |
| PPF | 101.2 ± 2.71 | 104.7 ± 2.50* | 107.5 ± 3.56** | 110.0 ± 2.53*** | 104.7 ± 2.75 |
| Hb I | 105.1 ± 4.56 | 105.8 ± 3.34 | 105.8 ± 4.22 | 105.2 ± 3.34c | 105.6 ± 3.20 |
| Hb II | 102.3 ± 2.75 | 103.6 ± 2.81 | 103.8 ± 1.95 | 106.3 ± 6.79 | 103.7 ± 2.16 |
| Hb III | 97.0 ± 3.60 | 95.8 ± 5.50 | 98.0 ± 3.50b | 97.5 ± 6.00b | 102.0 ± 5.60 |
| 30. SERUM BICARB. [mEq/l] | | | | | |
| PPF | 22.2 ± 2.64 | 22.7 ± 2.80 | 23.8 ± 1.60 | 24.3 ± 1.37 | 26.2 ± 4.92 |
| Hb I | 22.6 ± 1.69 | 22.2 ± 2.67 | 22.4 ± 2.13 | 22.0 ± 2.00c | 22.8 ± 1.47 |
| Hb II | 23.5 ± 2.50 | 22.5 ± 2.69 | 22.5 ± 2.21 | 20.2 ± 2.67b | 22.2 ± 2.05 |
| Hb III | 22.3 ± 1.90 | 19.5 ± 2.50 | 18.5 ± 3.25*b | 20.0 ± 2.40b | 20.6 ± 2.80 |
| 31. SERUM OSMOLALITY [mOsm/kg] | | | | | |
| PPF | 304.4 ± 11.3 | 299.5 ± 11.3 | 290.5 ± 8.65* | 292.8 ± 9.91 | 293.7 ± 3.21* |
| Hb I | 300.0 ± 5.38 | 299.5 ± 6.20 | 296.5 ± 5.70 | 295.2 ± 6.88 | 296.2 ± 5.11 |
| Hb II | 309.0 ± 18.8 | 299.0 ± 7.34 | 300.2 ± 11.0 | 294.6 ± 10.5 | 297.2 ± 5.35 |
| Hb III | 301.8 ± 8.80 | 281.4 ± 6.80c | 279.6 ± 8.20 | 279.0 ± 6.50**c | 284.6 ± 6.70* |

M: ARITHMETIC MEAN
±SD: STANDARD DEVIATION
DIFFERENCES BETWEEN T-1 TO T-2, T-3, T-4, T-5:
***significant difference $P < 0.001$
**significant difference $P < 0.01$
*significant difference $P < 0.05$
DIFFERENCES BETWEEN THE GROUPS:
PPF-HbI
PPF-HbII
PPF-HbIII:
a - significant difference $P < 0.001$
b - significant difference $P < 0.01$
c - significant difference $P < 0.05$
n = 6 rabbits

TABLE II

| 1. HISTOPATHOLOGY [after 24 hours] | | | | | |
|---|---|---|---|---|---|
|  | HEART<br>M ± SD | LUNGS<br>M ± SD | KIDNEYS<br>M ± SD | LIVER<br>M ± SD | SPLEEN<br>M ± SD |
| PPF | 1.00 ± 0.00 | 1.40 ± 0.48 | 1.60 ± 0.48 | 1.40 ± 0.48 | 1.00 ± 0.00 |
| Hb I | 1.50 ± 0.50 | 2.00 ± 0.57 | 1.83 ± 0.36 | 1.50 ± 0.76 | 1.00 ± 0.00 |
| Hb II | 1.66 ± 0.74 | 1.83 ± 0.37 | 2.16 ± 0.37 | 1.83 ± 0.68 | 1.00 ± 0.00 |
| Hb III | 1.33 ± 0.46 | 1.83 ± 0.37 | 2.66 ± 0.46** | 2.00 ± 0.57 | 1.00 ± 0.00 |

M: ARITHMETIC MEAN
±SD: STANDARD DEVIATION
DIFFERENCES BETWEEN THE GROUPS:
PPF-HbI
PPF-HbII
PPF-HbIII:
***significant difference $P < 0.001$
**significant difference $P < 0.01$
*significant difference $P < 0.05$
n = 6 rabbits

|  | T-1<br>M ± SD | T-2<br>M ± SD | T-3<br>M ± SD | T-4<br>M ± SD | T-5<br>M ± SD | T-7<br>M ± SD |
|---|---|---|---|---|---|---|
| 1. BODY WEIGHT [gm] | | | | | | |
| PPF | 4166 ± 262.4 | — | — | 4260 ± 309.8 | 4170 ± 292.0 | — |
| Hb IV | 4117 ± 146.2 | — | — | 4185 ± 147.0 | — | — |
| 2. BODY TEMPERATURE [°C] | | | | | | |
| PPF | 38.7 ± 0.42 | 38.5 ± 0.44 | 38.5 ± 0.46 | 38.5 ± 0.47 | 38.6 ± 0.45 | — |
| Hb IV | 39.0 ± 0.12 | 38.9 ± 0.34 | 38.8 ± 0.52 | 38.8 ± 0.44 | 39.0 ± 0.17 | — |
| 3. HEART RATE [Beats/min] | | | | | | |
| PPF | 220 ± 21.9 | 200 ± 13.20 | 195 ± 21.23* | 197 ± 16.43* | 198 ± 5.03* | — |
| Hb IV | 232 ± 8.97 | 191 ± 20.08** | 197 ± 15.96** | 189 ± 20.49** | 207 ± 17.94* | — |
| 4. BLOOD PRESSURE (SYSTOLIC) [mmHg] | | | | | | |
| PPF | 100 ± 6.32 | 95.8 ± 14.06 | 95 ± 10.00 | 96.7 ± 5.18 | 96 ± 4.18 | — |

TABLE II-continued

| | | | | | | |
|---|---|---|---|---|---|---|
| Hb IV | 88 ± 3.26b | 92.0 ± 4.47 | 89.6 ± 10.02 | 90.3 ± 4.67 | 88 ± 0.00c | — |
| 5. BLOOD PRESSURE (DIASTOLIC) [mmHg] | | | | | | |
| PPF | 60.8 ± 9.17 | 60.8 ± 14.63 | 60.8 ± 9.70 | 62.5 ± 6.89 | 65.0 ± 4.08 | — |
| Hb IV | 61.0 ± 3.60 | 69.3 ± 3.58** | 66.8 ± 5.60 | 67.7 ± 6.15 | 66.0 ± 0.00 | — |
| 6. URINARY OUTPUT [ml/30 min.] | | | | | | |
| PPF | 2.60 ± 0.49 | 0.0 ± 0.00*** | 3.00 ± 0.61 | 3.10 ± 0.63 | 3.00 ± 0.53 | — |
| Hb IV | 5.16 ± 0.89b | 6.58 ± 5.00a | 12.66 ± 6.49*a | 18.00 ± 8.69a | 8.67 ± 2.21a | — |
| 7. ARTERIAL BLOOD pH [UNITS] | | | | | | |
| PPF | 7.33 ± 0.04 | 7.34 ± 0.05 | 7.33 ± 0.03 | 7.33 ± 0.33 | 7.39 ± 0.13 | — |
| Hb IV | 7.31 ± 0.01 | 7.32 ± 0.01 | 7.29 ± 0.03 | 7.30 ± 0.02 | 7.32 ± 0.01 | — |
| 8. $PaO_2$ [mm Hg] | | | | | | |
| PPF | 69.9 ± 8.29 | 70.8 ± 11.72 | 62.0 ± 4.67* | 59.2 ± 8.09* | 69.2 ± 5.88 | — |
| Hb IV | 65.8 ± 4.53 | 71.5 ± 6.69 | 74.4 ± 9.66c | 65.6 ± 5.75 | 64.3 ± 2.15 | — |
| 9. $PaCO_2$ [mm Hg] | | | | | | |
| PPF | 29.8 ± 3.24 | 31.2 ± 2.77 | 33.7 ± 2.98* | 34.8 ± 2.11** | 31.9 ± 5.15 | — |
| Hb IV | 28.7 ± 4.09 | 31.3 ± 4.89 | 31.2 ± 4.87 | 31.3 ± 4.44 | 29.5 ± 3.46 | — |
| 10. BLOOD $P_{50}$ [mmHg] | | | | | | |
| PPF | 34.0 ± 0.61 | 33.7 ± 1.75 | 33.8 ± 3.01 | 34.0 ± 1.80 | 34.0 ± 1.80 | — |
| Hb IV | 32.9 ± 1.09 | 28.2 ± 2.05b | 29.2 ± 2.11c | 30.8 ± 1.46*c | 31.3 ± 0.47 | — |
| 11. COLLOID OSMOTIC PRESSURE (COP) [mmHg] | | | | | | |
| PPF | 18.2 ± 0.53 | 19.2 ± 0.06* | 19.3 ± 0.77* | 18.8 ± 0.60 | 18.3 ± 0.59 | — |
| Hb IV | 17.0 ± 0.24 | 19.2 ± 0.36*** | 19.0 ± 0.38*** | 18.5 ± 0.35*** | 17.8 ± 0.41* | — |
| 12. PLASMA Hb [g/dl] | | | | | | |
| PPF | 0.00 ± 0.00 | 0.00 ± 0.00 | 0.00 ± 0.00 | 0.00 ± 0.00 | 0.00 ± 0.00 | — |
| Hb IV | 0.00 ± 0.00 | 3.73 ± 0.24*a | 3.46 ± 0.31*a | 3.03 ± 0.32*a | 1.90 ± 0.22*a | — |
| 13. WBC [$\times 10^9$] | | | | | | |
| PPF | 6.27 ± 2.13 | 6.48 ± 1.16 | 7.25 ± 2.15 | 6.58 ± 1.53 | 6.55 ± 1.20 | — |
| Hb IV | 5.48 ± 0.87 | 3.88 ± 0.85*b | 6.21 ± 2.50 | 9.00 ± 3.43 | 12.8 ± 4.92* | 5.82 ± 1.92 |
| 14. RBC [$\times 10^{12}$] | | | | | | |
| PPF | 5.10 ± 0.42 | 3.75 ± 0.42*** | 3.90 ± 0.27*** | 3.80 ± 0.39*** | 3.79 ± 0.32** | — |
| Hb IV | 5.49 ± 0.30 | 4.12 ± 0.34*** | 4.06 ± 0.39*** | 4.15 ± 0.37*** | 3.95 ± 0.36*** | 3.89 ± 0.42** |
| 15. HEMOGLOBIN [g/dl] | | | | | | |
| PPF | 11.6 ± 0.82 | 8.4 ± 0.93*** | 8.8 ± 0.59*** | 8.6 ± 0.72*** | 8.7 ± 0.72*** | — |
| Hb IV | 12.4 ± 0.68 | 12.3 ± 0.54a | 11.8 ± 0.68a | 11.8 ± 0.84a | 10.7 ± 0.90*b | 9.5 ± 0.94*** |
| 16. HEMATOCRIT [%] | | | | | | |
| PPF | 33.7 ± 2.85 | 24.6 ± 2.77*** | 25.5 ± 1.77*** | 24.9 ± 2.01*** | 24.9 ± 1.98*** | — |
| Hb IV | 37.2 ± 1.56c | 27.9 ± 2.18*** | 27.6 ± 2.64*** | 28.1 ± 2.24*** | 26.9 ± 2.18*** | 29.0 ± 2.54*** |
| 17. PLATELETS [$\times 10^9$] | | | | | | |
| PPF | 388 ± 54.5 | 300 ± 45.6* | 336 ± 51.8** | 314 ± 39.8* | 376 ± 36.2 | — |
| Hb IV | 453 ± 50.5 | 285 ± 52.1*** | 309 ± 42.5*** | 324 ± 49.7** | 354 ± 23.6* | 400 ± 175.5 |
| 18. FIBRINOGEN [mg/dl] | | | | | | |
| PPF | 226 ± 31.8 | 165 ± 19.7** | 180 ± 11.5** | 191 ± 21.5* | 334 ± 32.6*** | — |
| Hb IV | 217 ± 33.3 | 114 ± 29.8*b | 117 ± 34.9b | 102 ± 29.6*b | 391 ± 33.2* | 500 ± 153.1* |
| 19. FIBRIN SPLIT PROD. [mcg/ml] [0 = <10 mcg/ml, 1 = >10 <40 mcg/ml, 2 = >40 mcg/ml] | | | | | | |
| PPF | 0.00 ± 0.00 | 0.00 ± 0.00 | 0.16 ± 0.37 | 0.00 ± 0.00 | 0.00 ± 0.00 | — |
| Hb IV | 0.00 ± 0.00 | 1.67 ± 0.47*a | 1.83 ± 0.37*a | 1.83 ± 0.37*a | 0.75 ± 0.43a | 0.00 ± 0.00 |
| 20. PROTHROMBIN TIME [sec] | | | | | | |
| PPF | 10.8 ± 2.11 | 11.2 ± 1.64 | 9.25 ± 2.00 | 9.4 ± 1.00 | 8.00 ± 0.32* | — |
| Hb IV | 11.0 ± 1.41 | 12.9 ± 1.92 | 15.5 ± 2.83*c | 12.6 ± 2.29c | 8.10 ± 0.10** | 8.02 ± 0.04** |
| 21. TOTAL BILIRUBIN [mg/dl] | | | | | | |
| PPF | 0.33 ± 0.05 | 0.20 ± 0.08 | 0.23 ± 0.05 | 0.23 ± 0.09 | 0.27 ± 0.11 | — |
| Hb IV | 0.17 ± 0.16 | 0.28 ± 0.07 | 0.78 ± 0.54 | 0.38 ± 0.41 | 0.53 ± 0.55 | 0.45 ± 0.11* |
| 22. SGOT (AST) [Iu/L] | | | | | | |
| PPF | 39.6 ± 4.96 | 38.0 ± 4.53* | 29.7 ± 5.85* | 30.0 ± 3.66* | 69.7 ± 7.49*** | — |
| Hb IV | 34.8 ± 9.19 | 41.0 ± 4.89b | 52.0 ± 17.2c | 62.0 ± 27.8b | 380.0 ± 137.9***b | 58.2 ± 21.2 |
| 23. LDH [Iu/L] | | | | | | |
| PPF | 69.0 ± 12.0 | 50.8 ± 5.83** | 60.0 ± 14.0 | 52.6 ± 9.63* | 135 ± 35.5*** | — |
| Hb IV | 64.5 ± 15.1 | 43.3 ± 17.9 | 60.0 ± 40.8 | 86.0 ± 49.2 | 428.8 ± 336* | 180 ± 122.5 |
| 24. SGPT [ALT] [uI/L] | | | | | | |
| PPF | 46.2 ± 8.67 | 31.5 ± 7.99* | 33.2 ± 8.82* | 32.5 ± 8.48* | 60.5 ± 5.44* | — |
| Hb IV | 48.7 ± 12.2 | 37.2 ± 4.20 | 48.0 ± 17.2 | 60.0 ± 6.32a | 191 ± 109.4*c | 58.7 ± 16.7 |
| 25. BUN [mg/dl] | | | | | | |
| PPF | 16.2 ± 2.13 | 16.2 ± 3.37 | 14.5 ± 2.43 | 14.2 ± 2.40 | 13.5 ± 2.08 | — |
| Hb IV | 15.2 ± 3.13 | 16.3 ± 3.25 | 15.8 ± 3.97 | 16.6 ± 4.53 | 20.4 ± 3.49*c | 15.2 ± 1.46 |
| 26. SERUM CREATININE [mg/dl] | | | | | | |

TABLE II-continued

| | | | | | | |
|---|---|---|---|---|---|---|
| PPF | 1.25 ± 0.18 | 1.23 ± 0.18 | 1.05 ± 0.10 | 1.07 ± 1.16 | 1.10 ± 0.12 | — |
| Hb IV | 1.42 ± 0.31 | 1.83 ± 0.62 | 1.70 ± 0.60c | 1.36 ± 0.54 | 1.40 ± 0.37 | 1.26 ± 0.15 |
| 27. SERUM SODIUM [mEq/l] | | | | | | |
| PPF | 137.0 ± 2.19 | 139.0 ± 2.86 | 140.5 ± 4.08 | 141.0 ± 4.31 | 145.0 ± 1.25*** | — |
| Hb IV | 138.6 ± 3.39 | 135.0 ± 3.07 | 135.8 ± 2.03 | 138.2 ± 2.67 | 143.0 ± 4.00 | 143.0 ± 0.00 |
| 28. SERUM POTASSIUM [mEq/l] | | | | | | |
| PPF | 3.45 ± 0.26 | 3.30 ± 0.30 | 3.50 ± 0.27 | 3.27 ± 0.28 | 4.35 ± 0.35*** | — |
| Hb IV | 3.32 ± 0.13 | 3.31 ± 0.17 | 3.55 ± 0.19 | 3.68 ± 0.30* | 3.25 ± 0.05b | 4.3 ± 0.00*** |
| 29. SERUM CHLORIDE [mEq/l] | | | | | | |
| PPF | 101.2 ± 2.71 | 104.7 ± 2.50* | 107.5 ± 3.56** | 110.0 ± 2.53*** | 104.7 ± 2.75 | — |
| Hb IV | 104.2 ± 2.47 | 104.6 ± 4.34 | 105.0 ± 5.71 | 105.6 ± 3.85 | 106.5 ± 2.50 | 106.0 ± 0.00 |
| 30. SERUM BICARB. [mEq/l] | | | | | | |
| PPF | 22.2 ± 2.64 | 22.7 ± 2.80 | 23.8 ± 1.60 | 24.3 ± 1.37 | 26.2 ± 4.92 | — |
| Hb IV | 23.2 ± 2.79 | 22.0 ± 2.08 | 22.8 ± 3.07 | 21.5 ± 3.20 | 22.0 ± 0.00 | 24.0 ± 0.00 |
| 31. SERUM OSMOLALITY [mOsm/kg] | | | | | | |
| PPF | 304.4 ± 11.3 | 299.5 ± 11.3 | 290.5 ± 8.65* | 292.8 ± 9.91 | 293.7 ± 3.21* | — |
| Hb IV | 290.5 ± 2.96 | 289.2 ± 5.15 | 288.2 ± 9.06 | 291.0 ± 6.22 | 293.5 ± 0.50 | 285.0 ± 0.00 |

M: ARITHMETIC MEAN
±SD: STANDARD DEVIATION
DIFFERENCES BETWEEN T-1 TO T-2, T-3, T-4, and T-5:
***significant difference $P < 0.001$
**significant difference $P < 0.01$
*significant difference $P < 0.05$
DIFFERENCES BETWEEN THE GROUPS PPF - Hb IV:
a - significant difference $P < 0.001$
b - significant difference $P < 0.01$
c - significant difference $P < 0.05$
n = 6 rabbits

TABLE III

Analysis of variance based on Difference in Scores
4 groups analyzed

| | Treatment Times | | | | |
|---|---|---|---|---|---|
| Parameter | T1 baseline | T2 15 min. | T3 1 hour | T4 3 hours | T5 24 hours |
| GENERAL SIGNS | | | | | |
| Body Weight | — | — | — | NS | NS |
| Body Temperature | — | NS | NS | NS | NS |
| CARDIOVASCULAR FUNCTION | | | | | |
| Heart Rate | — | NS | NS | NS | NS |
| Systolic blood pressure | — | 0.017 | NS | NS (P = 0.074) | 0.035 |
| Diastolic blood pressure | — | NS | NS | NS | NS |
| Arrhythmias | — | NS | NS | NS | — |
| Urinary output (ml/30 min) | — | <0.001 | 0.006 | 0.035 | NS |
| 1 vs. 2 | | NS | 0.013 | NS | NS (P = 0.09) |
| 3 vs. 2 | | NS | NS | NS | NS |
| 4 vs. 2 | | <0.001 | <0.001 | 0.006 | NS (P0.09) |
| RESPIRATORY FUNCTION | | | | | |
| Arterial Blood pH | — | NS | NS | NS | NS (0.09) |
| Pa O$_2$ | — | NS | 0.035 | 0.006 | NS (0.074) |
| 1 vs. 2 | | NS | NS | NS | NS |
| 3 vs. 2 | | NS | 0.006 | 0.014 | NS (0.055) |
| 4 vs. 2 | | NS | NS | 0.002 | NS |
| Pa CO2 | — | 0.004 | 0.011 | NS | NS |
| 1 vs. 2 | | NS | NS | NS | NS |
| 3 vs. 2 | | NS | NS | NS | NS |
| 4 vs. 2 | | 0.006 | 0.006 | NS | NS |
| Blood P$_{50}$ | — | 0.015 | NS | NS | — |
| HEMATOLOGY | | | | | |
| WBC | — | 0.002 | 0.002 | NS | NS |
| 1 vs. 2 | | 0.045 | NS | NS | NS |
| 3 vs. 2 | | NS | NS | NS | NS |
| 4 vs. 2 | | <0.001 | <0.001 | NS | NS |
| RBC | — | NS | NS | NS | NS |
| Hemoglobin | — | <0.001 | <0.001 | 0.003 | NS |
| 1 vs. 2 | | <0.001 | <0.001 | 0.001 | 0.021 |
| 3 vs. 2 | | <0.001 | 0.001 | 0.004 | NS |
| 4 vs. 2 | | <0.001 | <0.001 | 0.002 | NS |
| Hemocrit | — | NS | NS | NS | NS |
| Platelets | — | 0.030 | 0.037 | 0.010 | NS |
| 1 vs. 2 | | NS | NS | NS | NS |
| 3 vs. 2 | | 0.038 | 0.033 | 0.059 | NS |
| 4 vs. 2 | | 0.008 | 0.006 | 0.001 | NS |
| COAGULATION STUDIES | | | | | |

TABLE III-continued

Analysis of variance based on Difference in Scores
4 groups analyzed

| Parameter | T1 baseline | T2 15 min. | T3 1 hour | T4 3 hours | T5 24 hours |
|---|---|---|---|---|---|
| Fibrinogen | — | NS | NS | NS | NS |
| Prothombin Time | | NS | NS | NS | NS |
| LIVER FUNCTION | | | | | |
| SGOT | — | <0.001 | NS | NS | 0.043 |
| 1 vs. 2 | | <0.001 | NS (0.052) | NS | NS |
| 3 vs. 2 | | <0.001 | NS | NS | NS |
| 4 vs. 2 | | <0.001 | NS | NS | 0.016 |
| LDH | — | NS | NS | NS (0.087) | NS (0.080) |
| SGPT | — | NS | <0.001 | NS | NS |
| 1 vs. 2 | | NS | <0.001 | NS | NS |
| 3 vs. 2 | | NS | <0.001 | NS | NS |
| 4 vs. 2 | | NS | <0.001 | NS | NS |
| RENAL FUNCTION | | | | | |
| BUN | — | NS | NS | NS | NS |
| Serum creatinine | | NS | NS (0.095) | NS (0.069) | NS |
| Serum sodium | | NS | NS | NS | NS |
| Serum Potassium | — | NS | NS | NS | NS |
| Serum chloride | | NS | NS | NS | NS |
| Serum bicarbonate | | NS | 0.033 | 0.044 | NS |
| 1 vs. 2 | | NS | NS | NS | NS |
| 3 vs. 2 | | NS | NS | 0.009 | NS |
| 4 vs. 2 | | 0.043 | 0.004 | 0.030 | NS |
| Serum osmolarity | — | NS | NS | NS | NS |

TABLE IV

Students t-test For Paired Data
Comparison of 18 cases and 6 controls.

| | Time 2 5 min. baseline mean ± se (n) | | Time 3 1 hr-baseline mean ± se (n) | | Time 4 3 hr-abaseline mean ± se (n) | | Time 5 24 hr-baseline mean ± se (n) | |
|---|---|---|---|---|---|---|---|---|
| GENERAL DATA | | | | | | | | |
| Body weight | | | | | | | | |
| cases | | | | | 0.11 ± 0.02 | 16 | 0.01 ± 0.02 | 18 |
| control | | | | | 0.09 ± 0.02 | 6 | 0.01 ± 0.07 | 6 |
| | | | | | NS | | NS | |
| Body temperature | | | | | | | | |
| cases | −0.22 ± 0.07 | 18 | −0.14 ± 0.15 | 18 | −0.19 ± 0.14 | 18 | −13 ± 0.10 | 16 |
| controls | −0.23 ± 0.13 | 6 | −0.18 ± 0.15 | 6 | −0.18 ± 0.09 | 6 | 0.00 ± 0.00 | 4 |
| | NS | | NS | | NS | | NS | |
| Heart rate | | | | | | | | |
| cases | −18.7 ± 5.2 | 18 | −15.9 ± 6.1 | 18 | −6.8 ± 9.1 | 18 | −6.4 ± 4.8 | 16 |
| controls | −23.0 ± 9.2 | 5 | −25.6 ± 10.8 | 5 | −22.0 ± 11.7 | 5 | −16.3 ± 11.4 | 4 |
| | NS | | NS | | NS | | NS | |
| Systolic blood pressure | | | | | | | | |
| cases | +7.5 ± 3.2 | 18 | +6.7 ± 3.0 | 18 | +2.7 ± 3.3 | 18 | +6.5 ± 2.9 | 13 |
| controls | −4.2 ± 3.3 | 6 | −5.0 ± 3.4 | 6 | −3.3 ± 3.3 | 6 | −4.0 ± 2.9 | 5 |
| | NS ($P = 0.060$) | | 0.050 | | NS | | NS | |
| Diastolic blood pressure | | | | | | | | |
| cases | 10.0 ± 2.9 | 18 | 9.9 ± 2.8 | 18 | 5.0 ± 3.0 | 18 | 4.2 ± 2.6 | 13 |
| controls | 0.0 ± 2.9 | 6 | 0.0 ± 2.6 | 6 | 1.7 ± 3.3 | 6 | 2.0 ± 4.1 | 5 |
| | NS ($P = 0.076$) | | NS ($P = 0.063$) | | NS | | NS | |
| Arrhythmia | | | | | | | | |
| cases | 0 ± 0 | 18 | 0.18 ± 0.10 | 17 | 0.06 ± 0.06 | 17 | 0 ± 0 | 13 |
| controls | 0 ± 0 | 6 | 0 ± 0 | 6 | 0 ± 0 | 6 | 0 ± 0 | 4 |
| | NS | | NS | | NS | | NS | |
| Urinary output (ml/30 min) | | | | | | | | |
| cases | −1.6 ± 0.6 | 18 | 3.7 ± 0.5 | 18 | 3.4 ± 0.8 | 18 | 1.5 ± 0.2 | 13 |
| controls | −2.9 ± 0.2 | 4 | 0.1 ± 0.1 | 4 | 0.3 ± 0.8 | 4 | 0.1 ± 0.0 | 4 |
| | NS ($P = 0.074$) | | <0.001 | | <0.001 | | | |
| Respiratory Function Data | | | | | | | | |
| Arterial Blood pH | | | | | | | | |
| cases | −0.02 ± 0.02 | 18 | −0.04 ± 0.03 | 18 | −0.01 ± 0.03 | 18 | | |
| controls | 0.01 ± 0.01 | 6 | 0.00 ± 0.02 | 6 | 0.00 ± 0.02 | 6 | | |
| | NS | | NS | | NS | | | |
| $PaO_2$ | | | | | | | | |
| cases | 4.0 ± 3.5 | | 8.3 ± 3.9 | 18 | 12.6 ± 4.8 | 18 | 3.9 ± 3.0 | 15 |
| controls | 0.9 ± 5.6 | | −8.0 ± 4.3 | 6 | −10.8 ± 5.8 | 6 | −0.8 ± 3.6 | 4 |
| | NS | | 0.035 | | 0.017 | | NS | |

TABLE IV-continued

Students t-test For Paired Data
Comparison of 18 cases and 6 controls.

| | Time 2<br>5 min. baseline<br>mean ± se (n) | | Time 3<br>1 hr-baseline<br>mean ± se (n) | | Time 4<br>3 hr-abaseline<br>mean ± se (n) | | Time 5<br>24 hr-baseline<br>mean ± se (n) | |
|---|---|---|---|---|---|---|---|---|
| $PaCO_2$ | | | | | | | | |
| cases | 0.1 ± 1.3 | 18 | 1.6 ± 1.2 | 18 | 1.4 ± 1.2 | 18 | 1.7 ± 1.1 | 15 |
| controls | 1.4 ± 1.2 | 6 | 3.9 ± 1.2 | 6 | 5.0 ± 3.9 | 6 | 1.8 ± 1.2 | 4 |
| | NS | | NS | | NS | | NS | |
| Blood $P_{50}$ | | | | | | | | |
| cases | −4.4 ± 0.6 | 8 | −2.8 ± 0.7 | 8 | −1.4 ± 0.6 | 8 | no data for | |
| controls | −0.3 ± 0.6 | 3 | −0.2 ± 1.3 | 3 | 0.0 ± 0.6 | 3 | controls | |
| | 0.004 | | NS | | NS | | | |
| COP | | | | | | | | |
| cases | 0.10 ± 0.01 | 10 | 0.09 ± 0.01 | 10 | 0.07 ± 0.01 | 10 | 0.03 ± 0.01 | 8 |
| controls | 0.05 ± 0.004 | 3 | 0.06 ± 0.01 | 3 | 0.03 ± 0.01 | 3 | 0.00 ± 0.003 | 3 |
| | 0.007 | | NS | | NS | | 0.030 | |
| Hematology data | | | | | | | | |
| WBC | | | | | | | | |
| cases | −1.4 ± 0.3 | 18 | −0.6 ± 0.5 | 18 | 0.0 ± 0.6 | 18 | 3.6 ± 1.4 | 13 |
| controls | 0.1 ± 0.5 | 6 | 0.9 ± 0.5 | 6 | 0.2 ± 0.6 | 6 | 0.8 ± 0.5 | 4 |
| | 0.036 | | NS | | NS | | NS (P = 0.094) | |
| RBC | | | | | | | | |
| cases | −1.2 ± 0.1 | 6 | −1.2 ± 0.1 | 18 | −1.3 ± 0.1 | 18 | −1.2 ± 0.2 | 13 |
| controls | −1.4 ± 0.2 | 18 | −1.2 ± 0.2 | 6 | −1.3 ± 0.2 | 6 | −1.1 ± 0.1 | 4 |
| | NS | | NS | | NS | | NS | |
| Hemoglobin | | | | | | | | |
| cases | −0.2 ± 0.2 | 18 | −0.3 ± 0.2 | 18 | −0.8 ± 0.3 | 18 | −1.2 ± 0.4 | 13 |
| controls | −3.2 ± 0.5 | 6 | −2.8 ± 0.4 | 6 | −3.1 ± 0.4 | 6 | −2.6 ± 0.4 | 4 |
| | <0.001 | | <0.001 | | <0.001 | | NS (P = 0.099) | |
| Hematocrit | | | | | | | | |
| cases | −8.0 ± 0.7 | 18 | −7.8 ± 0.7 | 18 | −8.2 ± 0.8 | 18 | −7.6 ± 1.3 | 13 |
| controls | −9.1 ± 1.4 | 6 | −8.2 ± 1.1 | 6 | −8.8 ± 1.3 | 6 | −7.4 ± 0.9 | 4 |
| | NS | | NS | | NS | | N | |
| Platelets | | | | | | | | |
| cases | −161 ± 18 | 18 | −152 ± 16 | 18 | −143 ± 14 | 18 | −36 ± 41 | 13 |
| controls | −88 ± 14 | 6 | −53 ± 34 | 6 | −74 ± 25 | 6 | −12 ± 30 | 4 |
| | 0.035 | | 0.008 | | 0.021 | | NS | |
| COAGULATION STUDIES | | | | | | | | |
| Fibrinogen | | | | | | | | |
| cases | −89 ± 10 | 18 | −102 ± 10 | 18 | −108 ± 13 | 17 | 96 ± 36 | 13 |
| controls | −61 ± 19 | 6 | −46 ± 28 | 6 | −52 ± 11 | 5 | 91 ± 21 | 4 |
| | NS | | 0.029 | | 0.037 | | NS | |
| Prothrombin time | | | | | | | | |
| cases | 0.5 ± 0.6 | 16 | 1.0 ± 0.6 | 16 | 0.7 ± 0.4 | 16 | −1.1 ± 0.6 | 13 |
| controls | 0.5 ± 0.9 | 6 | −1.5 ± 0.4 | 6 | −0.7 ± 1.0 | 5 | −2.4 ± 0.7 | 4 |
| | NS | | 0.024 | | NS | | NS | |
| LIVER FUNCTION | | | | | | | | |
| Total B | no data | | | | | | | |
| SGOT | | | | | | | | |
| cases | 64.2 ± 6.1 | | 50.7 ± 27.8 | 13 | 61.3 ± 23.3 | 15 | 236.9 ± 80.0 | 13 |
| controls | −9.4 ± 3.7 | | −10.2 ± 7.6 | 5 | −8.2 ± 5.6 | 5 | 21.7 ± 20.7 | 3 |
| | <0.001 | | 0.050 | | 0.011 | | 0.021 | |
| LDH ( ) | | | | | | | | |
| cases | 0.34 ± 0.26 | 17 | 0.44 ± 0.29 | 17 | 0.64 ± 0.27 | 17 | 0.85 ± 0.41 | 15 |
| controls | −0.28 ± 0.21 | 6 | −0.16 ± 0.21 | 6 | −0.04 ± 0.21 | 6 | 0.54 ± 0.32 | 4 |
| | NS | | NS | | NS | | NS | |
| SGPT | | | | | | | | |
| cases | −0.9 ± 51.8 | 10 | 48.1 ± 4.4 | 9 | 13.2 ± 39.6 | 13 | 64.6 ± 35.8 | 14 |
| controls | −8.5 ± 7.3 | 6 | −6.8 ± 6.4 | 6 | −7.5 ± 65 | 6 | 22.5 ± 16.4 | 4 |
| | NS | | <0.001 | | NS | | NS | |
| RENAL FUNCTION | | | | | | | | |
| BUN | | | | | | | | |
| cases | 0.4 ± 0.4 | 18 | 0.2 ± 0.4 | 18 | −0.6 ± 0.8 | 18 | 1.8 ± 1.6 | 13 |
| controls | 0.0 ± 0.7 | 6 | −1.7 ± 0.3 | 6 | −2.0 ± 0.4 | 6 | −2.0 ± 0.8 | 4 |
| | NS | | 0.016 | | NS | | NS | |
| Serum creatinine | | | | | | | | |
| cases | 0.65 ± 0.33 | 18 | 0.84 ± 0.54 | 17 | 1.01 ± 0.47 | 17 | 0.56 ± 0.28 | 14 |
| controls | −0.02 ± 0.03 | 6 | −0.20 ± 0.05 | 6 | −0.18 ± 0.07 | 6 | −0.13 ± 0.05 | 4 |
| | NS (P = 0.059) | | NS (P = 0.076) | | 0.023 | | 0.027 | |
| Serum sodium | | | | | | | | |
| cases | −2.7 ± 1.1 | 18 | −0.8 ± 1.8 | 18 | −0.6 ± 1.5 | 18 | 5.4 ± 1.4 | 14 |
| controls | 2.7 ± 0.5 | 6 | 3.8 ± 1.5 | 6 | 4.5 ± 1.9 | 6 | 7.5 ± 0.6 | 4 |
| | <0.001 | | NS | | NS (P = 0.089) | | NS | |
| Serum potassium | | | | | | | | |
| cases | −0.14 ± 0.11 | 18 | −0.03 ± 028 | 18 | −0.23 ± 0.15 | 18 | 0.14 ± 0.23 | 14 |

TABLE IV-continued

Students t-test For Paired Data
Comparison of 18 cases and 6 controls.

|  | Time 2<br>5 min. baseline<br>mean ± se (n) | | Time 3<br>1 hr-baseline<br>mean ± se (n) | | Time 4<br>3 hr-abaseline<br>mean ± se (n) | | Time 5<br>24 hr-baseline<br>mean ± se (n) | |
|---|---|---|---|---|---|---|---|---|
| controls | −0.15 ± 0.04<br>NS | 6 | 0.05 ± 0.03<br>NS | 6 | −0.18 ± 0.14<br>NS | 6 | 1.03 ± 0.18<br>NS (P = 0.067) | 4 |
| Serum chloride | | | | | | | | |
| cases | 0.0 ± 1.3 | 18 | 0.8 ± 0.9 | 18 | 1.2 ± 2.0 | 18 | 2.4 ± 1.6 | 14 |
| controls | 3.5 ± 0.9<br>NS | 6 | 6.3 ± 1.5<br>0.007 | 6 | 8.8 ± 0.9<br>0.002 | 6 | 2.5 ± 1.9<br>NS | 4 |
| Serum bicarbonate | | | | | | | | |
| cases | −1.7 ± 0.7 | 18 | −2.0 ± 0.6 | 18 | −2.4 ± 0.8 | 18 | −1.4 ± 0.9 | 14 |
| controls | 0.5 ± 0.3<br>0.007 | 6 | 1.7 ± 1.2<br>0.010 | 6 | 2.2 ± 0.9<br>0.004 | 6 | 4.3 ± 1.9<br>0.010 | 4 |
| Serum osmolarity | | | | | | | | |
| cases | −10.1 ± 4.2 | 17 | −11.4 ± 5.0 | 16 | −14.5 ± 4.1 | 17 | −12.7 ± 44 | 14 |
| controls | −1.5 ± 2.9<br>NS | 4 | −10.5 ± 6.7<br>NS | 4 | −7.5 ± 10.6<br>NS | 4 | −19.0 ± 6.0<br>NS | 2 |

PATHOLOGY DATA
mean score n P value

|  |  |  |  | ≧1, <2 | ≧2, <3 | ≧3, <4 | ≧4 | Tot |
|---|---|---|---|---|---|---|---|---|
| Heart | | | | | | | | |
| cases | 1.44 | 18 | NS | | | | | |
| controls | 1.00 | 6 | | | | | | |
| Lungs | | | | | | | | |
| cases | 1.89 | 18 | NS (P = 0.067) | 3(17) | 14(77) | 1(6) | 0 | 18 |
| controls | 1.58 | 6 | | 4(67) | 2(33) | 0(0) | 0 | 6 |
| Liver | | | | | | | | |
| cases | 1.75 | 18 | NS | | | | | |
| controls | 1.92 | 6 | | ≧1, <2 | ≧2, <3 | ≧3, <4 | ≧4 | Tot |
| Kidneys | | | | | | | | |
| cases | 2.33 | 18 | 0.002 | 2(11) | 11(62) | 4(22) | 1(6) | 18 |
| controls | 1.33 | 6 | | 5(83) | 1(17) | 0 | 0 | 6 |
| Spleen | | | | | | | | |
| cases | 1.00 | 9 | NS | | | | | |
| controls | 1.13 | 4 | | | | | | |

DATA ANALYSIS
· RESULTS

The three batches of hemoglobin here studied were:
Hb-I = Group 1
Hb-II = Group 3
Hb-III = Group 4

The batches were characterized as follows:

|  | Hb-I | Hb-II | Hb-III |
|---|---|---|---|
| 1. Hemogobin, g/dl | 14.0 | 13.0 | 10.0 |
| 2. Oxyhemoglobin | 90.3 | 91.2 | 98.6 |
| 3. Carboxyhemoglobin | 1.6 | 0.9 | 1.7 |
| 4. Methemoglobin | 8.8 | 10.6 | 2.7 |
| 5. Oxygen Vol. % | 17.5 | 16.2 | 13.6 |
| 6. pH | 7.5 | 6.55 | 7.0 |
| 7. Sodium, mEq/L | 118.5 | 102.3 | 119.2 |
| 8. Potassium, mEq/L | 3.88 | 4.16 | 2.44 |
| 9. Chloride, mEq/L | 118.0 | 117.3 | 120.9 |
| 10. Osmolarity, mOsm/Kg | 244 | 236 | 242 |
| 11. Endotoxins, EU/ml | <0.01 | <0.01 | <0.01 |
| 12. Molecular wt. between 68,000–500,000 | 85% | 80% | 90% |
| 13. Phospholipid analysis by TLC silica gel plate developed in iodine vapor | clear | clear | clear |

These batches were compared to human Plasma Protein Fraction (Plasma-Plex--Armour Pharmaeutical Company). (Group 2=Control Group)

(A) Mortality

None of the animals in the 4 groups (6 rabbits in each group) died by the end of the 24-hour observation period.

(B) Clinical Signs

During the first 3 hours following the administration of hemoglobin, the only clinical sign was hemoglobinuria. At 24 hours, all animals appeared normal; i.e., with normal degrees of activity and eating and drinking normally. By that time, the hemoglobinuria had subsided.

No change occurred in body weight and temperature.

Gross Pathology

None of the animals presented at necropsy with hemoglobin extravasation. All the organs appeared grossly normal, with the exception of the liver, which appeared congested in about half the animals.

Histopathology

Heart: Focal areas of myocardinal "contracture" were found in the PPF group, as well as in the hemoglobin groups. The severity of the change was graded as 1+ in the PPF group, and respectively 1.5+, 1.7+ and 1.25+ in the Groups 1, 3 and 4. The difference was not statistically significant.

Lungs: Areas of interstitial edema, congestion and cellular infiltration were found in all groups, including the PPF group. The severity of changes was graded 1.4+ for the PPF group, and respectively 2+, 1.8+ and 1.8+ for Groups 1, 3 and 4. The difference, again, was not statistically significant.

Liver: Changes found in the liver were more uniform than those observed in the other organs. Centrolobular vacuolization was graded as 1.4+ in the PPF group, and respectively 1.5+, 1.8+ and 2+ in Groups 1, 3 and 4. The difference was not significant.

Kidneys: No glomerular alteration and no acute tubular necrosis or blockage by pigment casts were found. Tubular epithelial vacuolization was uniformly found in the subcapsular area. Extension from here toward the cortico-medullary junction was graded as 1.6+ for the PPF group, and respectively 1.8+, 2.15+ and 2.7+ for Groups 1, 3 and 4. The difference between PPF and the hemoglobin groups was significant only for Group 3.

DISCUSSION AND CONCLUSION

Both the chemical and histopathologic changes observed in this study were mild-to-moderate and theoretically reversible. The determination of such reversibility is currently being investigated with the period of observation being extended from 24 hours to 1 week.

EXAMPLE V

EXCHANGE TRANSFUSION OF RABBITS

Utilizing the experimental protocol set out in detail in Example IV, three groups of rabbits were hemorrhage-transfused. One group of six rabbits (Group A) had one-third of the estimated blood volume replaced with a hemoglobin solution containing 1-2 endotoxin units per ml. One group of four rabbits (Group B) had one-third of the estimated blood volume replaced with 5% PPF. Another group of six rabbits (Group C) had one-third of the estimated blood volume replaced with a hemoglobin solution of the present invention, this solution characterized as follows:

|  | Run 1 | Run 2 | Run 3 | Average |
|---|---|---|---|---|
| 1. Hemoglobin, g/dl | 11.6; | 11.6; | 11.4; | 11.5 |
| 2. Oxy-hemoglobin, % | 90.3; | 90.2; | 90.1; | 90.2 |
| 3. Carboxy-Hb, % | 0.1; | 0.3; | 0.5; | 0.3 |
| 4. Met-Hb, % | 9.6; | 9.5; | 9.7; | 9.6 |
| 5. Oxygen Vol. % | 14.7; | 14.6; | 14.4; | 14.6 |
| 6. pH, Units | 7.140; | 7.161; | 7.168; | 7.156 |
| 7. PCO$_2$, Torr | 14.1; | 10.4; | 10.2; | 11.6 |
| 8. PO$_2$, Torr | 147.5; | 147.2; | 147.0 | 147.2 |
| 9. P$_{50}$, Torr | . 28.0; |  | 28.0 |  |
| 10. Colloid Osmotic Pressure, Torr | 20.7; | 21.0; | 20.9 | 20.9 |
| 11. Sodium, mEq/L | 114.6 | 113.9 | 115.1 | 114.5 |
| 12. Potassium, Eq/L | 3.72; | 3.63; | 3.70; | 3.68 |
| 13. Chloride, mEq/L | 111.0; | 208.4; | 107.2; | 108.9 |
| 14. Phosphorus, ng % | 0.097 | 0.097 | 0.097 | 0.097 |
| 15. Endotoxins, EU/ml | 0.29 | 0.19 | 0.23 | 0.23 |
| 16. Phospholipids, by TLC |  |  | absent |  |
| 17. Polymerization, by column 85% above tetrameric form. chromatography |  |  |  |  |

Comparisons for each group of one-third transfused rabbits during the twenty-four hour period following transfusion was made with regard to platelet numbers, white blood cell numbers, serum fibrinogen levels, prothrombin levels, and serum creatinine levels. The collected data appears in FIGS. 2-6 respectively. In each of FIGS. 2-6, the triangles represent mean values (± standard error) of the Group A rabbits, the squares represent the mean values (± standard error) for the Group B rabbits, and the circles represent the means value (± standard error) for the Group C rabbits.

A comparison of the data represented by FIGS. 2-6 demonstrates the cross-linked hemoglobin solution of this invention caused no mortality and no clinically important signs. Using an analysis of variance, at 24 hours post infusion there were no significant differences among the groups except for a slight increase in systolic pressure and an elevation of SGOT. The elevation of systolic blood pressure was considered clinically unimportant because it occurred within the clinically acceptable range (+20 mm Hg). The SGOT elevation was considered spurious because of colorimetric interference by plasma hemoglobin. Although the test groups exhibited transient hemoglobinuria, no significant increase in BUN or serum creatinine was detected. Similar histopathologic changes were found in both the PPF and the cross-linked hemoglobin solution of the present invention groups. These alterations were considered to be nonspecific and appeared to be reversible in nature.

EXAMPLE VI

EXCHANGE TRANSFUSION IN DOGS

Preliminary studies on exchange transfusions in dogs were performed on beagles and mongrel hounds with total blood volume exchanges ranging between 25%-75%. Dogs one, two and three are beagles weighing approximately ten kilograms each, and dogs number four, five and six are mongrel hounds weighing approximately 20 kilograms each.

Figure 8:
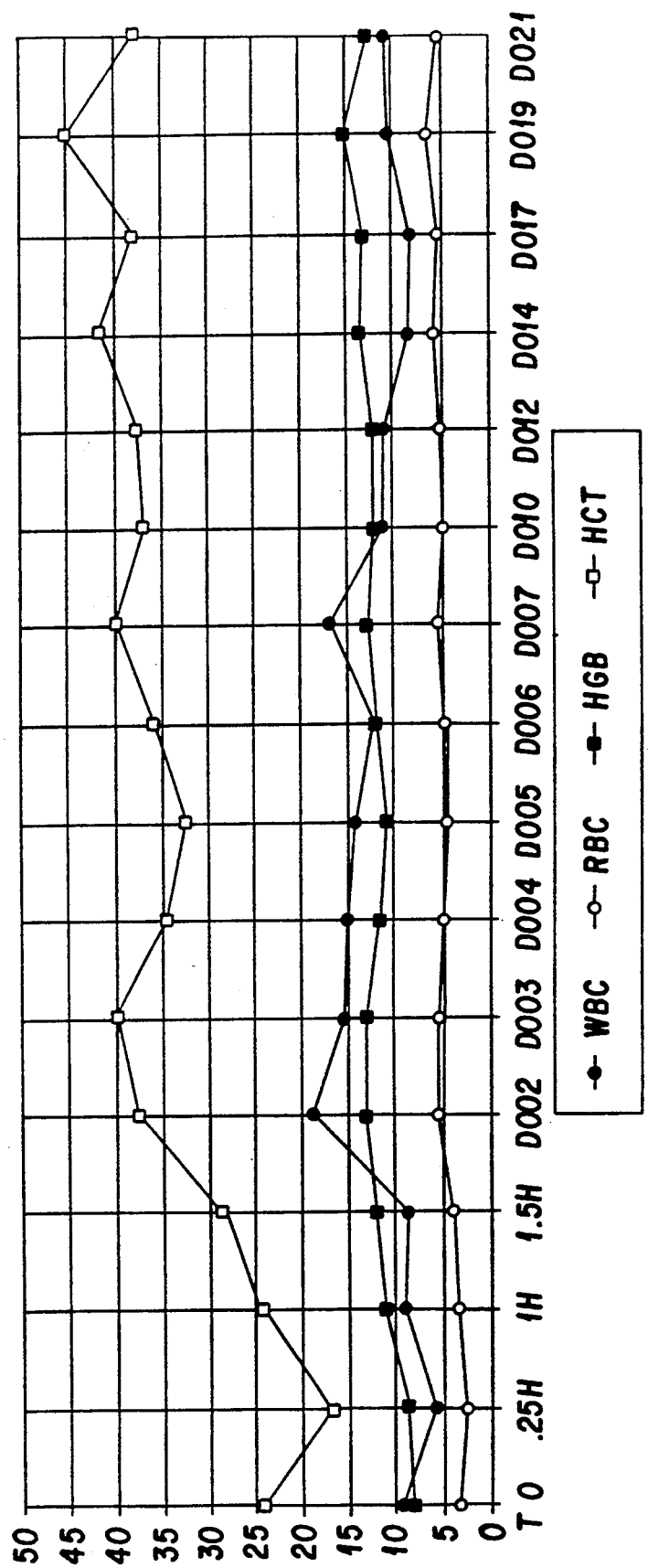
FIG. 8 is a graphic representation of white blood cell percent, red blood cell percent, hemoglobin percent, and hematocrit percent, from time 0 through day 21, of a dog which underwent a 40% exchange transfusion with a cross-linked hemoglobin solution of the present invention.

Dog number one (FIG. 8) is a beagle whose initial hematocrit of 24% indicated that he was anemic prior to transfusion. The anemia is of an undetermined type. This dog underwent a 40% exchange transfusion. Initial response was characterized by a rapid rise in hematocrit so that after 1.5 hours following exchange transfusion the hematocrit was measured at 28%. Subsequently, the hematocrit rose above 36% by the second post transfusion day and remained in the range of 40% (102 days following transfusion). There was also a sustained rise in the hemoglobin which initially represented both intracellular hemoglobin and free plasma hemoglobin as a result of the test infusion.

Chem 20 profiles obtained in a serial fashion, in general, failed to reveal any significant abnormalities although there was an indication of increased liver enzyme levels during the first nine days following infusion. Interpretation of these results is difficult because of interference produced by free hemoglobin in solution with standardized automated means of measuring liver enzymes.

Figure 9:
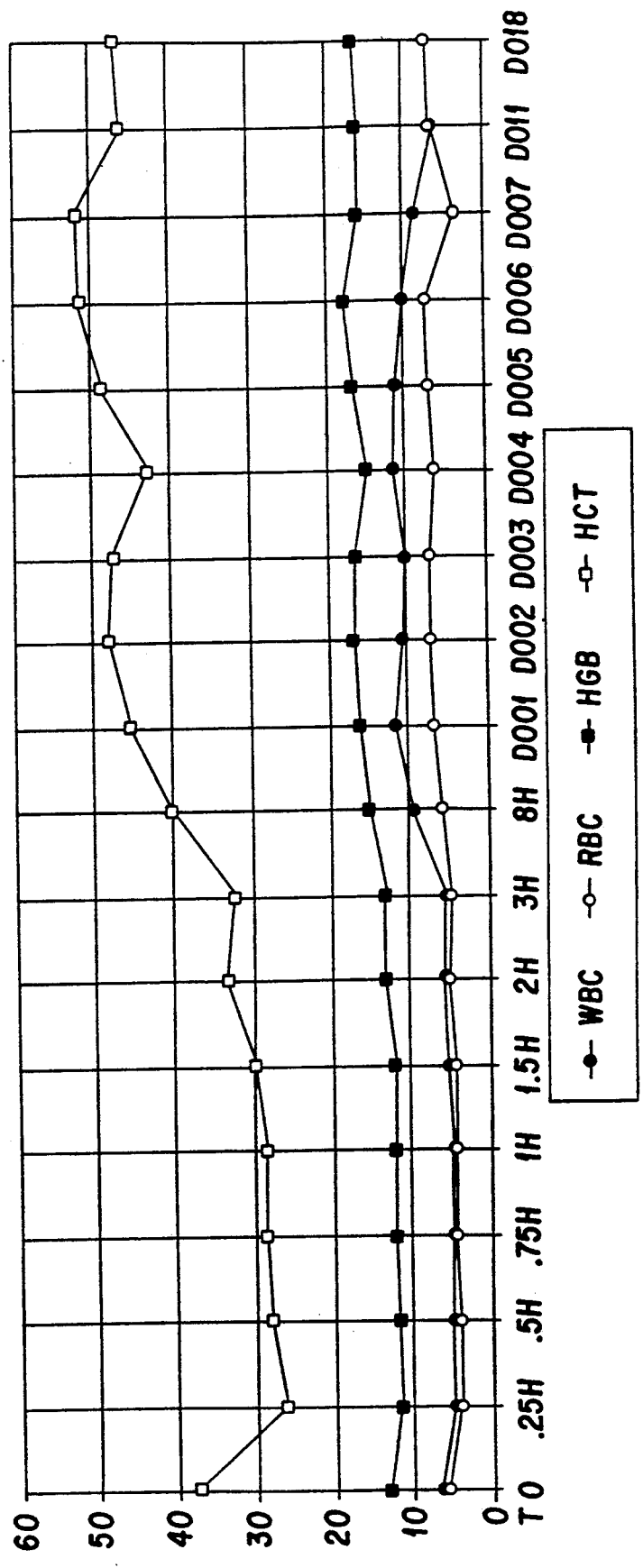
FIG. 9 is a graphic representation of white blood cell percent, red blood cell percent, hemoglobin percent, and hematocrit percent, from time 0 through day 18, of a dog which underwent a 25% exchange transfusion with a cross-linked hemoglobin solution according to the present invention.

Boston dog number two (FIG. 9) is a beagle who underwent a 25% exchange transfusion also without adverse clinical effects. The initial hematocrit was appropriately depressed after the exchange transfusion and rapidly rose to exceed the resting level of 37% after 8 hours. The elevated hematocrit level was sustained through the 92nd post transfusion day and is confirmed by appropriate parallel increases in the RBC count indicating increased red cell production. Similar liver enzyme changes were noted in the Creatanine and appeared to be slightly elevated above resting levels. The remaining Chem 20 values did not change significantly.

Figure 10:
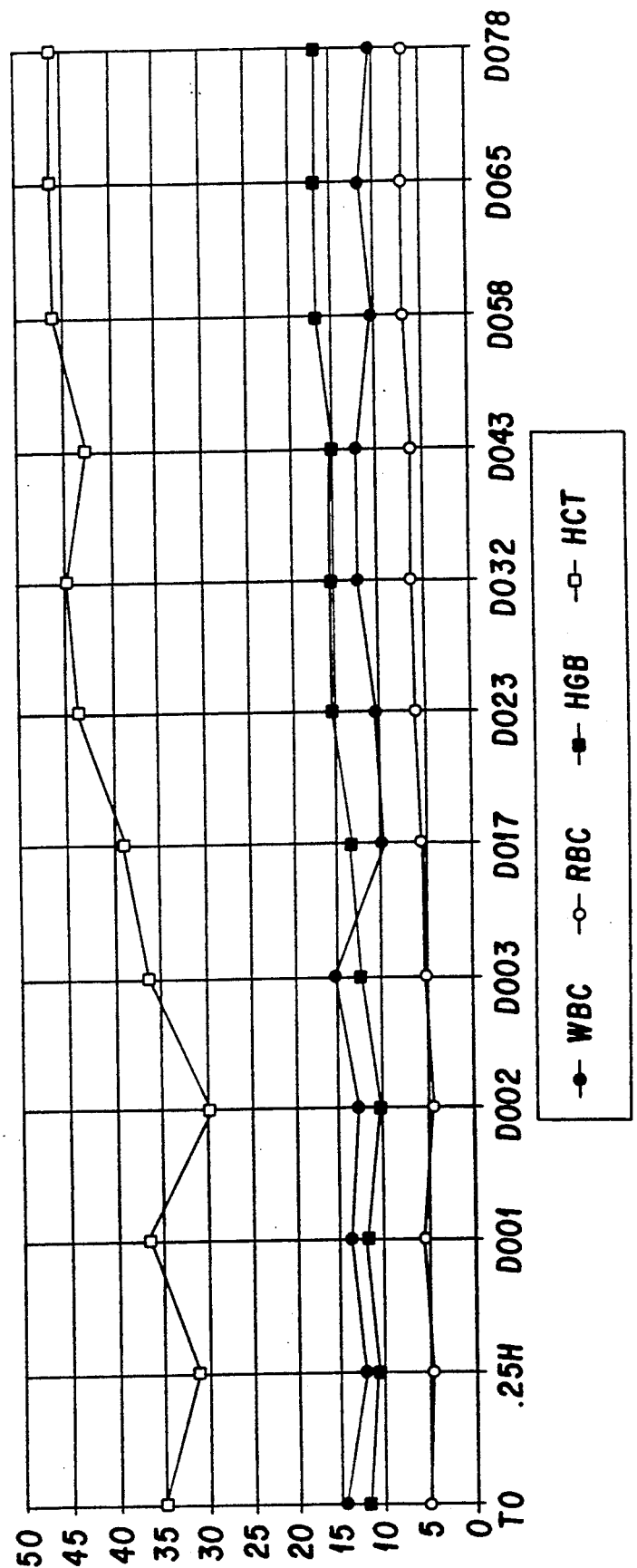
FIG. 10 is a graphic representation of white blood cell percent, red blood cell percent, hemoglobin percent, and hematocrit percent, from time 0 through day 78, of a dog which underwent a 33% exchange transfusion with a cross-linked hemoglobin solution according to the present invention.

Boston dog number three (FIG. 10) is a beagle who underwent a 33% exchange transfusion. A similar rise above resting hematocrit levels was noted after the first day and this was sustained through the 78th post transfusion day.

The liver enzymes showed a slightly different picture in this animal. Although the LDH appeared to have a transient elevation during the first two days, the LDH levels were normal thereafter. In contrast, the SGOT and SGPT values appeared to be moderately elevated over the resting levels for weeks after the initial transfusion. Clinically the animal appeared to have no adverse effects. However, the serum creatanine levels were slightly elevated following the infusion.

Figure 11:
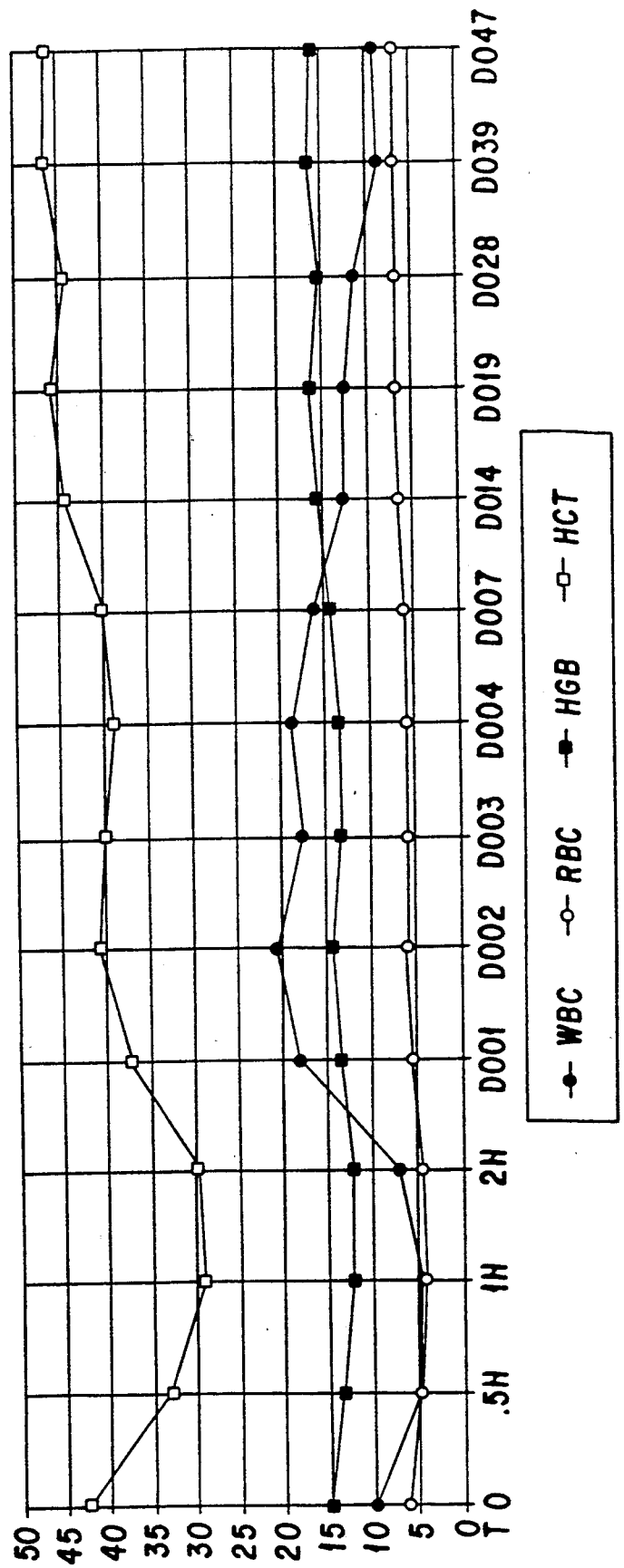
FIG. 11 is a graphic representation of white blood cell percent, red blood cell percent, hemoglobin percent, and hematocrit percent, from time 0 through day 47, of a dog which underwent a 33% transfusion with 5% human albumin solution.

Dog number four (FIG. 11) is a mongrel weighing approximately 17 kilograms and was used as a control animal. A 33% hemorrhage was induced and the extracted blood volume was replaced with an equal amount of 5% human albumin. This was followed by the hematocrit level returning to normal and slightly exceeding the resting value for the ensuing 81 days served.

Figure 12:
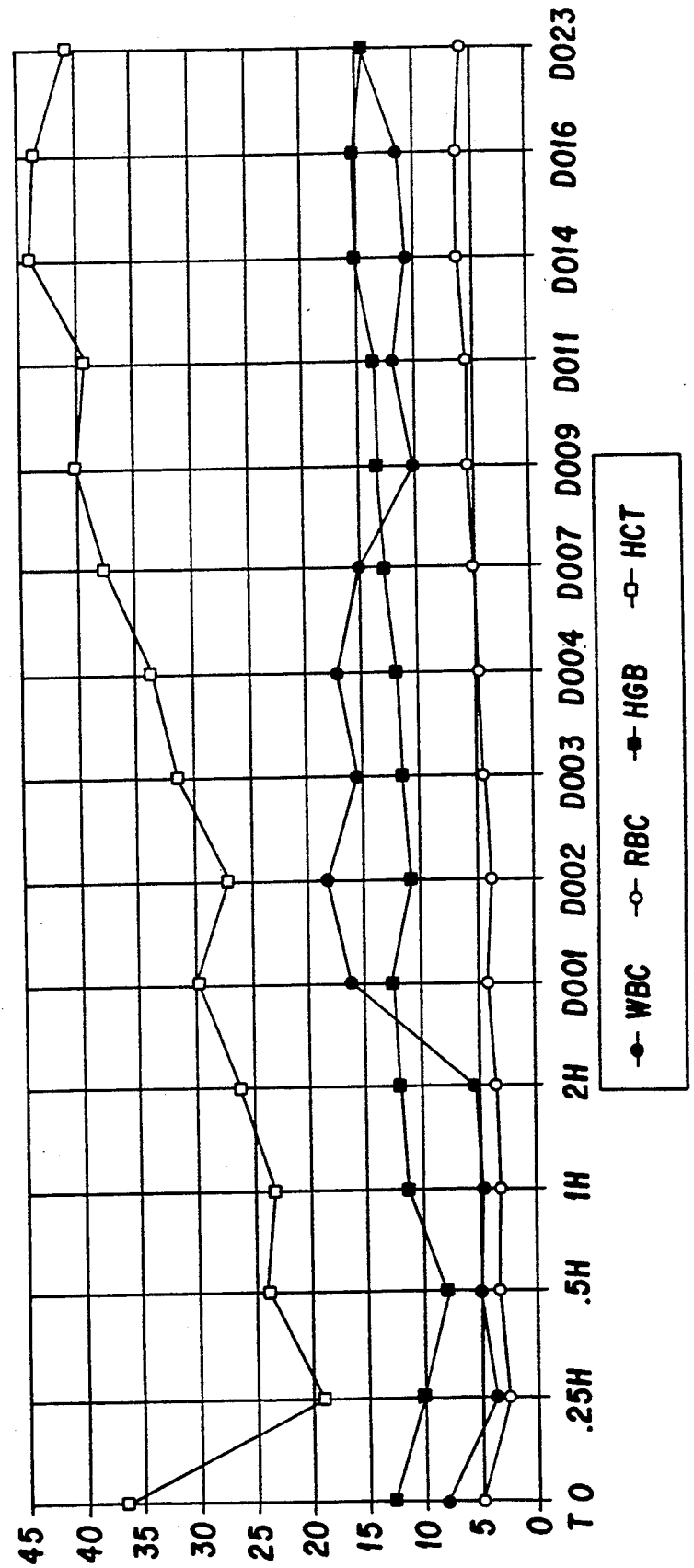
FIG. 12 is a graphic representation of white blood cell percent, red blood cell percent, hemoglobin percent, and hematocrit percent, from time 0 through day 23, of a dog which underwent a 50% blood volume hemorrhage, followed by immediate replacement with 5% albumin solution as a first step in the exchange transfusion. This was followed by a rapid removal of another 50% of the blood volume followed by replacement with a cross-linked hemoglobin solution of the present invention.

Dog number five (FIG. 12) is a mongrel hound weighing approximately 20 kilograms who underwent a 75% exchange transfusion with a significant decrease in hematocrit followed by an increase in hematocrit exceeding the resting level on the 7th post transfusion day. The animal sustained a hematocrit which exceeded the resting level for the ensuing 43 days following the transfusion.

The liver enzymes showed a transient rise in LDH and SGOT which gradually returned to the normal range. There was a single observation of an increase in SGPT which may have been aberrant data.

Figure 13:
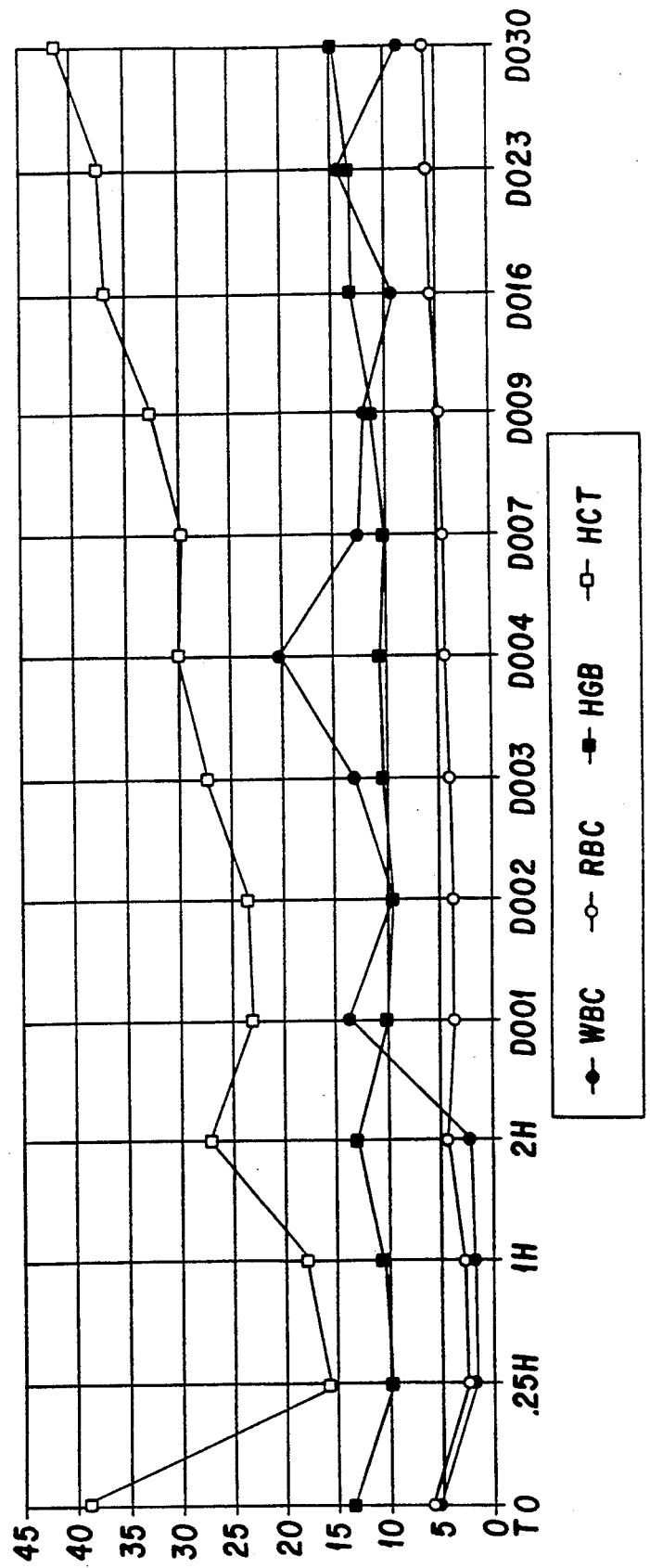
FIG. 13 is a graphic representation of white blood cell percent, red blood cell percent, hemoglobin percent, and hematocrit percent, from time 0 through day 30, of a dog which underwent a 50% hemorrhage followed by immediate replacement with an equal volume of a cross-linked hemoglobin solution of the present invention and a second 50% hemorrhage followed by replacement with an equal volume composed of a cross-linked hemoglobin solution of the present invention and a 5% albumin solution, mixed in equal parts.

Dog number six (FIG. 13) is a mongrel hound weighing approximately 20 kilograms who underwent a 75% exchange transfusion with similar findings as that found in dog number five.

All of the dogs tested appeared to be well clinically and experienced a rapid return to normal behavioral activity immediately after the acute effects of the anaesthesia subsided. There do not appear to be long term adverse effects observed in any of the tested animals.

SUMMARY

In a preliminary study of acute toxicity and efficacy of the cross-linked hemoglobin solution of the invention, five test dogs received single exchange transfusions replacing 25-75% of calculated blood volume and one control dog underwent a 33% exchange replacement with 5% albumin.

There was no mortality or clinical morbidity in any animal acutely or during an extended observation up to twelve weeks. All test dogs exhibited normal activity immediately after replacement and experienced a rapid return of RBC parameters to the normal range within two weeks. Test animal chemistry profiles remained within normal limits except for a transient elevation of liver enzymes, a finding also observed in the control dog (Dog #4). Arterial blood gas results on samples taken during and immediately after the exchange transfusions indicated that normal $PO_2$ values were maintained in all animals including the two dogs which underwent 75% exchanges.

Dogs #5 and #6 both received exchange transfusions of approximately 75% of the blood volume (calculated by body weight). Dog #5 underwent a 50% blood volume hemorrhage followed by immediate replacement with 5% albumin solution as a first step in the exchange transfusion. This was followed by a rapid removal of another 50% of the blood volume at which time Dog #5 became dyspnic manifested by a sudden increase in respiratory rate from 14 per minute to 38 per minute associated with agonal breathing pattern. Because of the obvious clinical distress exhibited by Dog #5 at this time an equal amount of the cross-linked hemoglobin solution of the invention solution was rapidly infused to restore the blood volume to normal. During the infusion of the crosslinked hemoglobin solution of the invention the respiratory rate returned to 14 associated with a cessation of the labored breathing pattern. Blood gas determinations prior to the first hemorrhage, after the first replacement and after the second replacement indicated that the $PO_2$ remained within the normal range.

Dog #6 also underwent a 75% exchange transfusion similar to Dog #5 but this time replacing the first 50% hemorrhage with an equal volume of the cross-linked hemoglobin solution of the invention and the second 50% hemorrhage with an equal volume composed of the cross-linked hemoglobin solution of the invention and 5% albumin mixed in equal parts. After the first hemorrhage and replacement, there were no signs of respiratory distress and there were no signs of respiratory distress during or after the second hemorrhage and replacement.

The arterial blood gas determinations during and after the exchange transfusion indicated a normal $PO_2$ was maintained throughout the exchange.

These data suggest that the cross-linked hemoglobin solution of the invention has both a volume expansion and an oxygen transport function. The response to a single transfusion of the cross-linked hemoglobin solution of the invention did not appear to be associated with abnormal clinical behavior or abnormal chemistry of hematologic parameters, although a transient rise in liver enzymes was seen in both the test dogs and the control.

EXAMPLE VII

IMMUNOGENICITY STUDIES

The immunogenicity of the hemoglobin solution produced in accordance with the protocol of Example I and having the properties as characterized above (Invention Hemoglobin solution) was tested in primates, subjected to three hemorrhage-transfusions of ⅓ the calculated blood volume.

Six Coebus monkeys, of 4 Kg body weight, were sedated with Ketamine, 15 mg/Kg body weight intramuscularly, and restrained. Sterile cannulae were inserted percutaneously into one femoral artery and vein. Blood was removed from the artery in an amount corresponding to 2% of body weight in kilograms (approximately ⅓ of blood volume). The Invention Hemoglobin solution was infused through the vein over a period of 30 minutes. Blood samples (2.5 ml) were taken (1) before the removal of blood, (2) 1 hour after the infusion of Invention Hemoglobin, (3) daily for week, (4) weekly for 1 month, (5) monthly for three months. The sera were tested for the presence of antibodies, using Ouchterlony's test. The same experiment was carried out after 3 and 6 months. Thus, each animal underwent 3 Invention Hemoglobin infusions at three-month intervals.

All animals survived the cycle of three hemorrhage-transfusions. No sign of toxicity was noted (all animals appeared normal). The Ouchterlony test resulted consistently negative for all sera, in all animals.

EXAMPLE VIII

MATERIAL PERSISTANCE IN THE CIRCULATION

This study was undertaken to demonstrate the unique vascular persistance of the hemoglobin product of the invention. Since the early days of hemoglobin research, it has been stated that hemoglobin is only maintained briefly in the circulation. The new technique and unique product not only works effectively but is maintained in the circulation.

To define the molecular weight of the product, we have developed data that characterizes the unique hemoglobin-based temporary blood substitute of this invention. We have measured the time elimination of the material in dog sera and have been able to characterize the blood substitute as having the following characteristics by testing protocol. In the following examples, the hemoglobin used on the test animals is the hemoglobin product produced in accordance with Example I and is referred to as Invention Hemoglobin.

1. Determination of molecular weight distribution of hemoglobin in dog sera

Beagle dog sera which had been obtained during efficacy trials of isovolemic exchange down to 5% hematocrit with Invention Hemoglobin were checked concerning their hemoglobin-molecular weight distribution by gel permeation chromatography (HP 1090 A). Changes in molecular weight distribution with time after Invention Hemoglobin application were as follows.

| 1.1 Analytical Conditions: | |
|---|---|
| HPLC-Device: | HP 1090 A |
| Integrator: | HP 3392 |
| Detector: | Diode array-UV-V/S/ (Hewlett Packard) |
| GPC-column: | TSK G 3.000 SW 300 mm × 7.5 mm |
| Eluent: | 0.1 n $K_2HPO_4$ (pH 7.0) |
| Detection wavelengths: | 260 nm (marker proteins)/ 405 nm (hemoglobin in dog sera) |

Results

These results are tabulated in the following Table V and then graphically represented in FIG. 14. It is easily seen that vascular persistance is maintained for much longer than the originally reported 24-hour period demonstrated in other solutions.

TABLE V

| | Evaluation of Beagle Dog Sera | | | | |
|---|---|---|---|---|---|
| Peak No. | % Hb | *1 | *2 | *3 | *4 |
| Dog serum, 0 value | | 3.14 | 6.62 | 5.4 | |
| 3 hr 20 min | 5.8 | 129.11 | 184.45 | 239.78 | 719.35 |
| 24 h | 5 | 170.11 | 188.34 | 230.87 | 461.74 |
| 48 h | 4.5 | 511.98 | 236.29 | 249.42 | 249.42 |
| 96 h | 3.8 | 910.38 | 165.00 | 172.50 | 127.50 |
| 120 h | 2.8 | 1,058.81 | 80.00 | 80.00 | 40.00 |
| 144 h | 1.5 | 1,837.00 | 60.00 | 60.00 | 15.00 |
| 168 h | 0.7 | 1,455.17 | 42.50 | 45.00 | 5.00 |
| 216 h | 0.08 | 11.18 | 17.74 | 18.47 | — |
| 240 h | 0.09 | 7.25 | 19.34 | 22.97 | — |
| 294 | 0.1 | 6.52 | 55.05 | 25.35 | — |

*The numbers in each column represent the peak height in centimeters times the full scale (in millivolts).

Due to the elimination of hemoglobin the concentration decreases continuously (see Table V). Therefore, it had been necessary to work with increasing amplifications ("full scale" (mV)) of the integrator system. In order to be able to compare the chromatographic peaks of different samples, peak areas or peak weights had to be recorded. This was carried out as follows:

The peak heights were multiplied by the amplification "full scale". The resulting values could be shown to be linear regarding hemoglobin concentration; this has been verified by adding Invention Hemoglobin to dog sera in hemoglobin concentrations from 1% to 7%. By plotting values log "peak height X full scale" vs. sampling time of sera (up to 294 h (Table V)), the kinetics shown in FIG. 14 can be obtained. Peak No. 1, representing the part of hemoglobin molecular weight distribution with the highest molecular weight, shows the highest retention time value, as is expected from theory. Half-life values cannot be calculated from this curve because it does not reveal an ideal exponential function.

For the hemoglobin-components, represented by peaks 2, 3, and 4, respectively, the following intravascular half-life values were found:

peak 2: ca.84 h
peak 3: ca.68 h
peak 4: ca.24 h

Decreasing half-life values, i.e., shorter intravascular retention times with decreasing molecular weight, confirm theoretical expectations.

Twenty-four hours after Invention Hemoglobin infusion, the molecular weight distribution in serum and in urine were examined. This comparison shows that exclusively peak No. 4, standing for the 68,000-Hb-component, appears in the urine after that time.

The amount of the Hb-component (peak No. 4) in percent of the total Invention Hemoglobin molecular weight distribution can be calculated by integration of the peak areas (see the following Table VI).

TABLE VI

| Sample | Peak No. 4 Area (% of Total Distribution) |
|---|---|
| Invention Hemoglobin | 48.0 |
| Serum 3 h 20 min | 44.0 |
| 24 h | 38.9 |
| 48 h | 14.6 |

Figure 14:
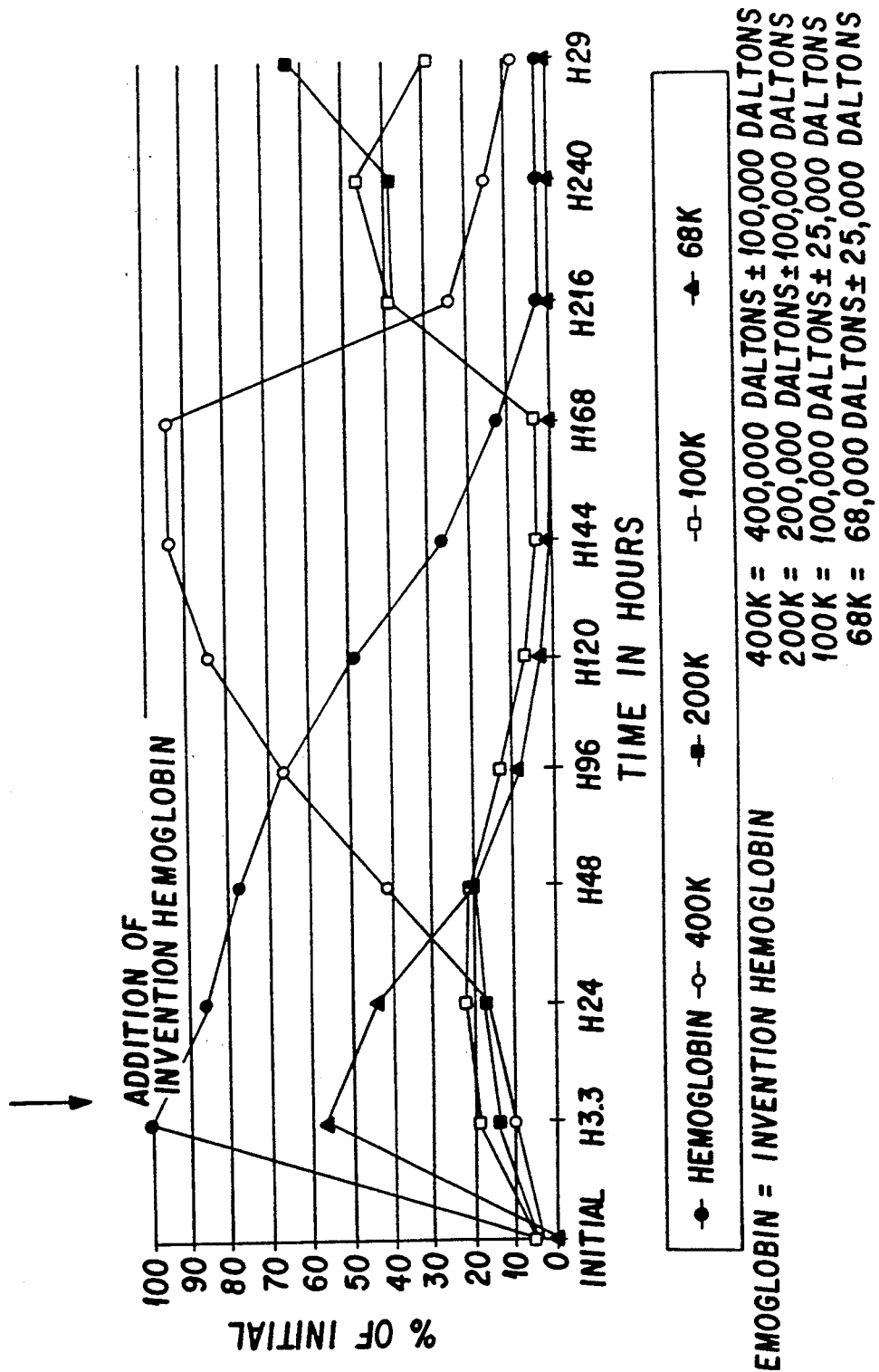
FIG. 14 is a graphic representation of Table V of Example VIII. The ordinate represents the percentage of total Invention Hemoglobin remaining in each one of its compositional subgroup molecular weights. The abscissa represents time in hours.
Figure 15:
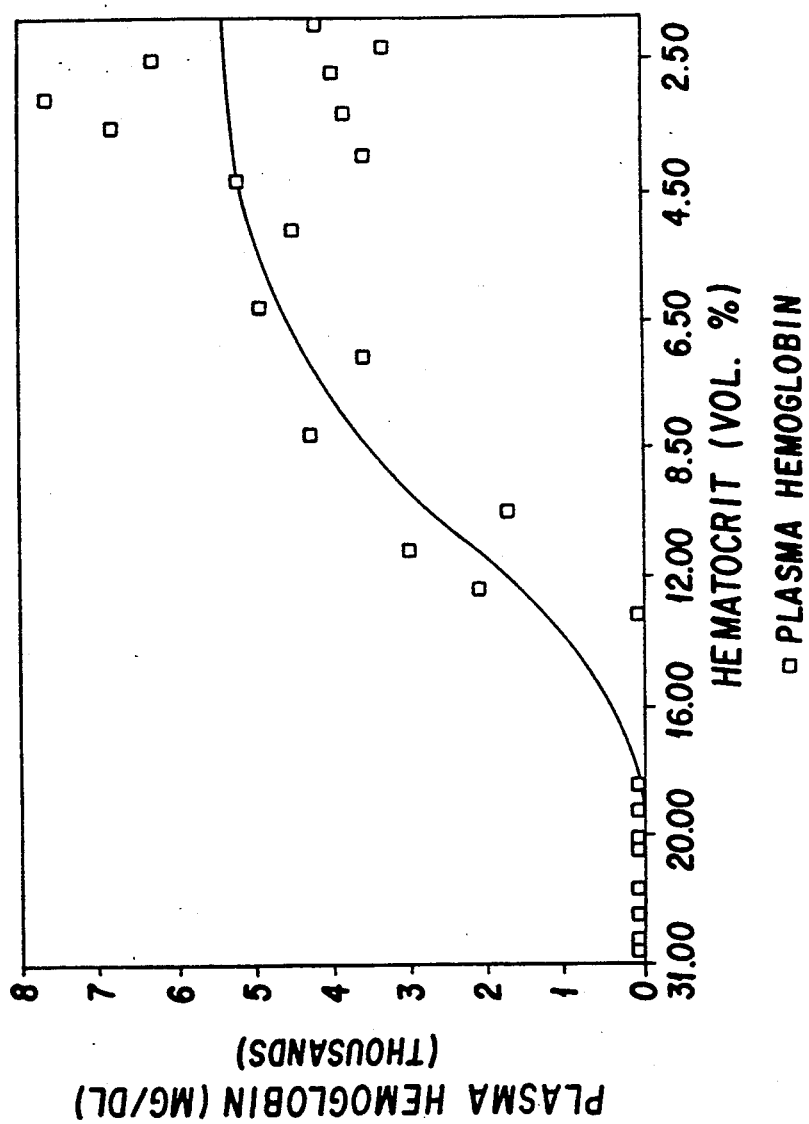
FIG. 15 is a graphic representation of the data collected from the experimental work of Example IX. The graph demonstrates that as red blood cells are progressively exchanged for Invention Hemoglobin, beginning at or below a hematocrit of 20%, there is an expected increase in the total plasma hemoglobin concentration.
Figure 16:
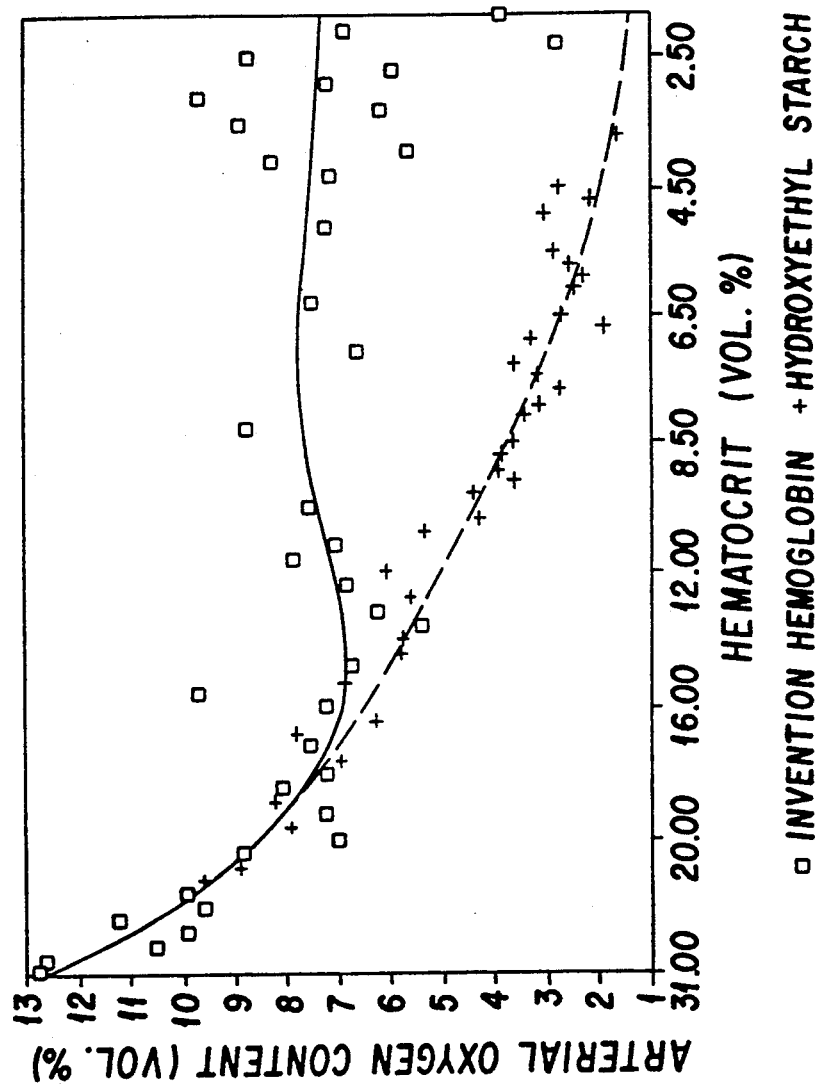
FIG. 16 is a graphic representation of data collected from the experimental work of Example IX. Seven test animals and six control animals were exchanged from initial hematocrit levels with non-oxygen bearing volume replacements (i.e., Ringer's lactate and hydroxyethyl starch solutions) down to approximately 20%. Both groups showed a similar decrease from initial values to approximately 20%. Below 20%, the control group showed a progressive decrease in arterial oxygen content associated with progressive decrease in hematocrit. The six control animals did not survive. In contrast, the test group displayed noticeably higher arterial oxygen content which was maintained despite the progressive decrease in hematocrit. The seven test animals survived and appeared clinically normal.
Figure 17:
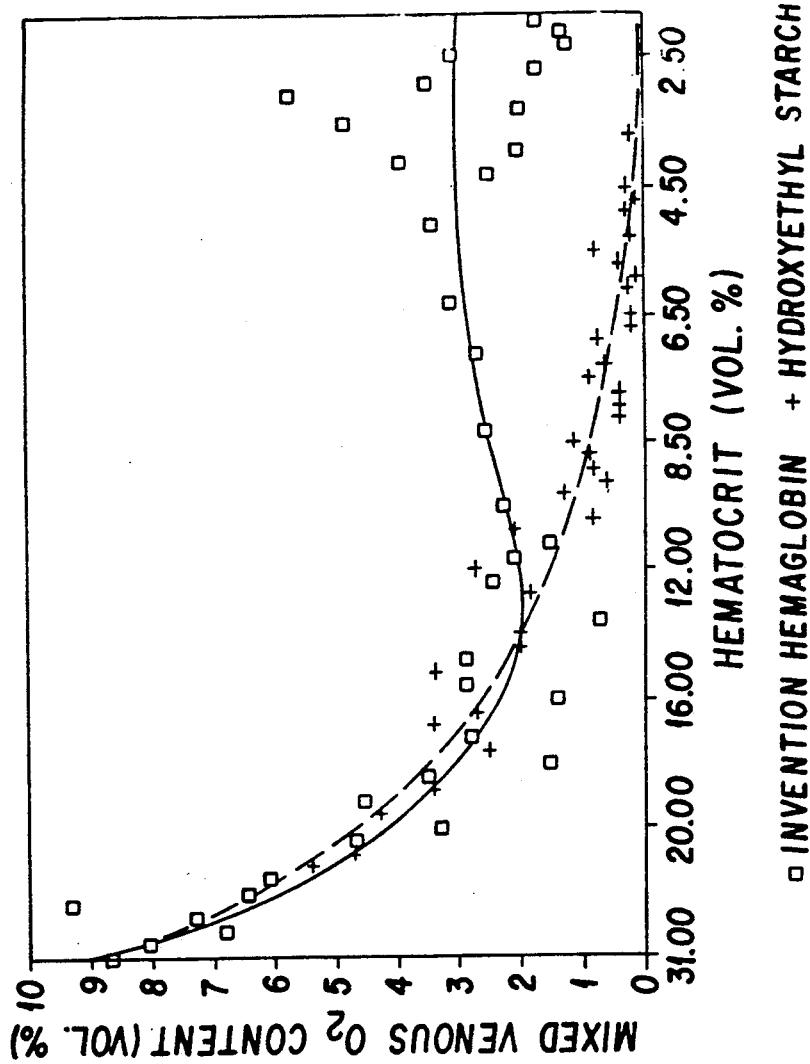
FIG. 17 is a graphic representation of experimental data collected from Example IX. The ordinate represents mixed venous oxygen content, while the abscissa represents hematocrit.

The best representation of elimination from sera is demontrated by the half-life evaluation curves in FIG. 14. In this figure, which is a graphical representation of the data of Table V, the data is a representation in percent of total Invention Hemoglobin remaining in each subgroup molecular weight percentage.

EXAMPLE IX

SHEEP EXPERIMENTS

Objective

The objective of this study was to determine the efficacy of Invention Hemoglobin solution infusion in splenectomized sheep through repeated exchange transfusion and removal of red blood cells, and lowering of hematocrit to approximately 5%. By this testing design, the potential efficacy of Invention Hemoglobin solutions may be demonstrated by survivability in the absence of red blood content sufficient to sustain life. The nature, degree, and duration of therapeutic effect was also assessed for each animal in this study.

Test Substance

Invention Hemoglobin solution as described above and as produced by Example I.

Test System

Purebred or mixed-breed sheep weighing 20.0 to 25.0 Kg were used for this study. Animals were obtained from a commercial colony whose animals have been certified for general health prior to the study and were known to be sero-negative for Q-fever. The sheep were vaccinated for common viral and bacterial pathogens; tested and treated for endo- and ectoparasites; and otherwise treated to minimize the effects of any diseases which could create a variable. Animals were housed individually in pens bedded with shavings, fed guaranteed sheep ration and had continuous access to potable water. Environmental parameters were maintained at 70° F.±3° F., 45% RH± and 12 hr/12 hr light cycle. The animal room was operated as a conventional animal room, but technicians wore gloves, lab coats, and gowns when performing procedures.

Instrumentation

At least two weeks prior to study, sheep were fasted for 24 hours, pre-anesthetized with 0.2 mg I.M. atropine sulfate, anesthetized with 4% halothane by mask, intubated and maintained with approximately 2% halothane. Splenectomy was then performed using aseptic technique through a ventral midline approach. The spleen was injected with 1:1000 epinephrine during this procedure to mobilize any stored RBCs. Following splenectomy, bone marrow and liver biopsies were taken. Animals were then allowed to recover for 14 days and monitored for continued good health. Hematology values were compared before and after splenectomy to determine any possible deleterious effects from the pre-study surgery procedure.

In order to conserve the test product Invention Hemoglobin, the initial exchanges were made with Ringer's lactate solution until a hematocrit of approximately 20% was achieved. Then additional exchanges were made using Invention Hemoglobin until the residual hematocrit was less than 5%. For this study, 7 sheep which were screened for general good health and pretreated for diseases were selected. Animals were uniquely identified for this study. In addition, 6 control sheep were tested in a similar way with Hespan ™ (hydroxyethyl starch solution) alone. During this study, one sheep was randomly selected for testing on each of eight testing days. The sheep were fasted for 24 hours prior to the study, and water was withheld approximately 16 hours. Sheep were weighed, premedicated with 0.2 mg I.M. atropine sulfate and anesthetized with 4% halothane administered by facemask. When suitably anesthetized, the sheep were intubated and maintained on approximately 2% halothane. Anesthesia was titrated to Stage III, Plane 2-3 and maintained. The femoral artery was dissected using aseptic techniques and 15-gauge catheters were placed in the vessel. Using similar techniques, the jugular was catheterized with a large bore Swan-Ganz catheter. The animal was then placed in a metabolic cage and was allowed to recover for two hours. Baseline blood pressure, measured by arterial catheter transducer, and blood samples were obtained using the implanted catheters. Twenty cc's of blood were removed each time for analysis of hematology, chemistry, and blood gas determinations. Using an isovolumetric method, the blood volume was replaced in each animal, as follows:

Procedure

1. Approximately 400 to 600 ml of the calculated circulatory volume (CV) was withdrawn from the femoral artery catheter. Blood pressure recordings were taken again and after shock was produced (BP of 60/40) saline was infused with Ringer's lactate at 5 to 10 ml/minute to replace the whole blood (equal volume). Blood pressure recordings and samples were again made following this infusion and the animal was allowed to stabilize.

2. After the stabilization period, blood pressures were recorded, followed by a second removal of another 400-600 ml of blood. Following this blood withdrawal, blood pressure values, samples, and clinical evaluation for signs of shock were performed for approximately 10 minutes.

3. After the 10 minute evaluation period, Invention Hemoglobin solution was administered at an infusion rate of 10 ml/minute. Blood pressure, samples, and clinical signs were monitored for 10 minutes to identify conditions which would represent therapeutic effects.

4. Steps 2 and 3 were repeated until the hematocrit was reduced to below 5%. Animals were observed continually and clinical signs were recorded.

5. Each animal was monitored so as to check for any signs associated with hemorrhage and treatment for a period of 2 hours. A terminal blood sample of 20 cc's was taken for hematology, chemistry, and blood gas analysis before removing the catheters and closing the catheterization sites sterilely under light halothane anesthesia.

6. Changes in urinary output were monitored in a metabolic cage and recorded througout the hemorrhage treatment and recovery periods. Blood gas values were also measured during each phase while arterial catheter was in place.

7. When animals recovered from anesthesia, they were returned to their cages and given supportive therapy as necessary indicated by their clinical condition. Comprehensive clincal monitoring and continued supportive therapy was provided for 21 days.

At the beginning of the study, baseline blood samples were drawn from the jugular vein and 24-hour urine samples were collected for urinalysis. At daily intervals and at the conclusion of the study, comparative blood samples were drawn, urine was collected and the ophthalmological examinations were repeated. On Day 14, the sheep were anesthetized as previously described and repeated liver and bone marrow biopsies were performed. Animals that died were evaluated by gross pathological and histopathological evaluations. The spectrum of tests performed were:

| Hematology | Clinical Chemistry | Blood Gases (arterial) |
|---|---|---|
| RBC | SGOT | $PO_2$ |
| WBC | SGPT | $PCO_2$ |
| Platelet Count | LDG | pH |
| Differential WBC | Alk Phos | $O_2$ saturation |
| Hemoglobin | BUN | $O_2$ content |
| Hemataocrit | Creatinine | |
| REBC Morphology | Bilirubin (I and D) | |
| Reticulocyte Count | Sodium | |
| | Potassium | |
| | Chloride | |
| | Calcium | |
| | Phosphorous | |
| | Total Protein | |
| | Albumin | |
| | Globulin | |
| | A/G/Ratio | |
| | Glucose | |
| | Cholesterol | |
| | Osmolarity | |
| | Carbon Dioxide | |

| | -continued | |
|---|---|---|
| | Triglycerides | |
| | Iron | |
| | Iron Building | |
| | Capacity | |
| | Urinalysis | |
| | Specific Gravity | |
| | pH | |
| | Protein | |
| | Glucose | |
| | Ketones | |
| | Hemoglobin | |
| | Hemoglobin Polymer | |
| | Creatinine/Sediment Exam | |
| Aqueous Humor | | |
| Hemoglobin | | |
| RBC | Serum and | |
| | Hemoglobin | |
| | Bovine Hemoglobin | |
| | Antibody | |
| CSF | Polymerized | |
| | Hemoglobin | |
| | Hemoglobin | Ferritin |
| RBC | Heptiglobin | |
| | | Gross and Histologic Pathology |
| Coagulation Tests | | |
| PT Lungs | | Heart |
| PTT Liver (biopsies included) | | Kidneys (L and R) |
| | | Brain |
| Fibrinogen | | Eyes |
| | | Adrenals (L and R) |
| | | Thyroid S |
| | | Bone Marrow (biopsies included) |
| Hemodynamics | | |
| Cardiac Output (thermal dilution) | | |
| Arterial Pressure | | |
| Central Venous Pressure | | |
| Pulmonary Artery Wedge Pressure | | |

All data from observations and tests were recorded on specific history, observation and testing report forms.

STATISTICAL ANALYSIS

Seven sheep were tested using the efficacy protocol. Each sheep has baseline blood samples and 24-hour urine samples performed. These data were obtained at daily intervals during the follow-up period. For each day of follow-up, statistical comparisons were performed using the paired test comparing each follow-up measurement with the corresponding baseline measurement. Of particular interest is a comparison of blood and measurements immediately after the completion of all exchange transfusions with the corresponding baseline measurements.

REFERENCES

1. *Blood Policy and Technology* (Washington, D.C.: U.S. Congress, Office Technology Assessment, OTA-H-260, January, pp. 133-150, 1985).
2. "Blood Groups and Blood Transfusion." In: *The Merck Veterinary Manual.* 5 ed. Merck Company, Inc., Rahway, N.J., pp. 42-49, 1979.
3. Kolata, R. J., Burrows, C. F. and Soma, L .R., "Shock: Pathophysiology and Management." In: *Current Veterinary Therapy in Small Animal Practice.* 7th ed., W.B. Saunders Company, Philadelphia, pp. 32-48, 1980.

PRELIMINARY RESULTS OF THE SHEEP EFFICACY PROTOCOL are included in this example. The raw data regarding hemodynamic parameters is presented in tabulated form in Tables VII (Test Animals) and VIII (Control Animals). The graphic presentation of the blood gas and hemodynamic data in FIGS. 15-19 show that the test animals maintained arterial and venous oxygen contents well above the levels achieved in the controls which received no oxygen-carrying volume replacement during exchange transfusions. All test animals survived the exchange.

In contrast, all six of the control animals did not survive the acute exchange transfusion. Six of the control animals showed deteriorating cardiac output as arterial and mixed venous oxygen contents, and hematocrits, fell below 10%.

Figure 18:
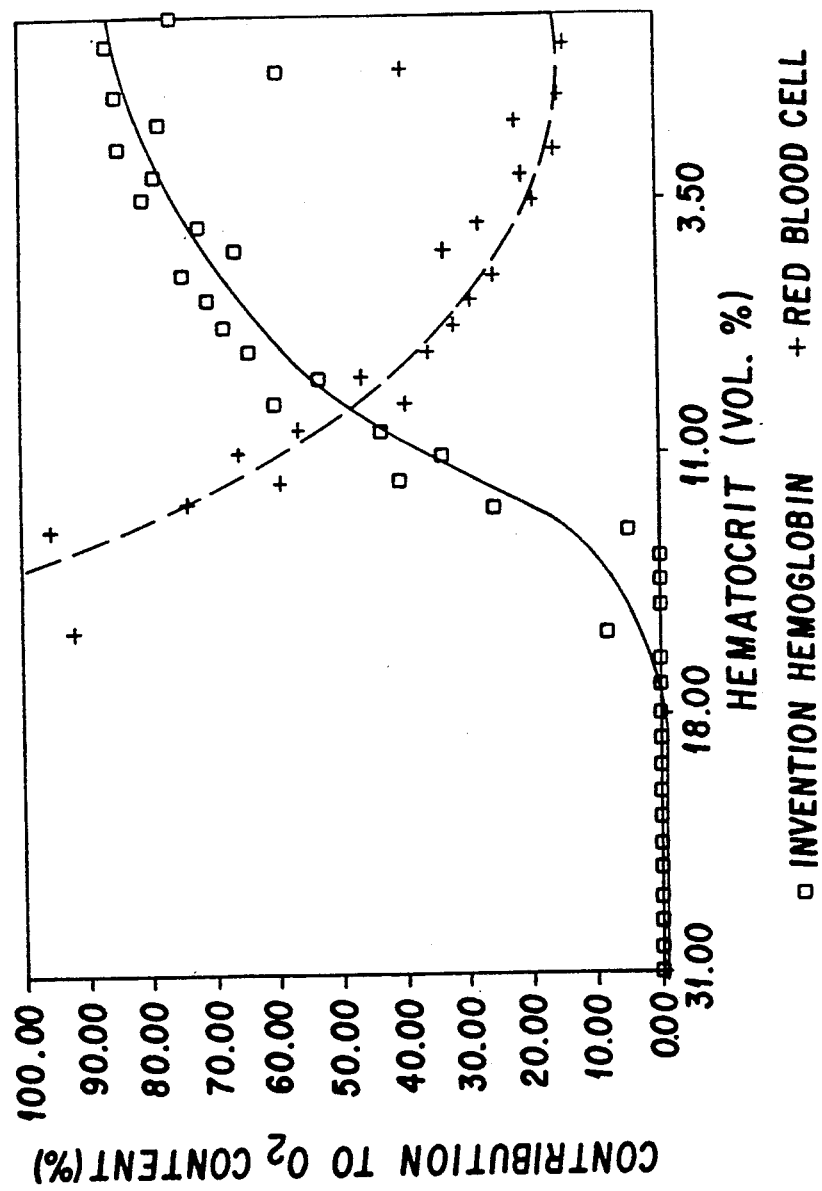
FIG. 18 is a graphic representation of data collected from Example IX. The ordinate represents contribution to oxygen content; the abscissa represents hematocrit. The graph demonstrates the contribution of Invention Hemoglobin and of sheep red blood cells to arterial oxygen content at various hematocrit levels. In the seven test animals, as Invention Hemoglobin increased and hematocrit decreased, an increase in percentage of arterial oxygen content was contributed by the Invention Hemogloin. At hematocrit levels in the range of 3%, almost 90% of arterial oxygen content is contributed by the Invention Hemoglobin, with the remainder being contributed by the residual sheep red blood cells and diluted plasma.

In FIG. 18, the contribution of the Invention Hemoglobin as compared to the sheep hematocrit is compared at decreasing hematocrit levels. FIG. 18 demonstrates that at the end of the exchanges when the residual hematocrit is below 5% that approximately 80-90% of the arterial oxygen content is contributed by the Invention Hemoglobin as compared to approximately 10-20% which is contributed by both the liquid phase of the blood and the remaining red blood cells in the test animals.

Both the test group and the control sheep breathed room air at all times during the experiment. Both the test group and the control group showed an identical decline in arterial oxygen content during the first exchange which lowered their respective groups from the baseline hematocrit down to the approximately 20% hematocrit levels. From this point on, the test group received Invention Hemoglobin in exchange for the native sheep red blood cells. At this point, the figures demonstrate that the oxygen content is well maintained in the animals where bovine hemoglobin is used to replace the removed blood. In the case of the controls, there is decrease in the venous oxygen contents which continues to parallel the decline in hematocrit since Hespan TM does not carry a significant amount of oxygen except as a dissolved gas.

Figure 19:
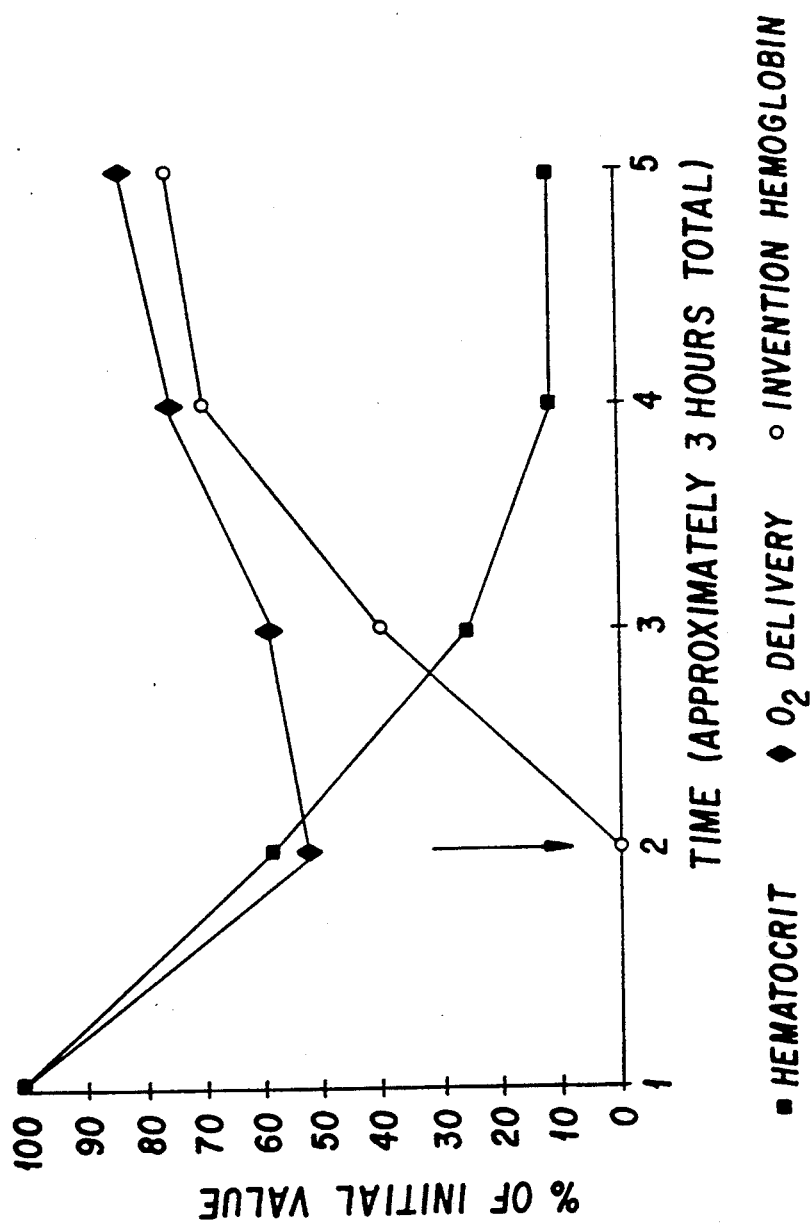
FIG. 19 is a graphic representation of oxygen delivery during exchange transfusion. The ordinate represents the percent of initial value; the abscissa represents time in hours. During the first exchange with Ringer's lactate solution, hematocrit as well as oxygen delivery decreased. At this point (→), exchanges were begun with Invention Hemoglobin solution. While sheep hematocrit decreased further, oxygen delivery increased back towards baseline levels, in association with the Invention Hemoglobin solution infusion. This demonstrates that at the end of the exchange, oxygen delivery is due principally to the Invention Hemoglobin and not to the residual hematocrit (approximately 3%).
Figure 20A:
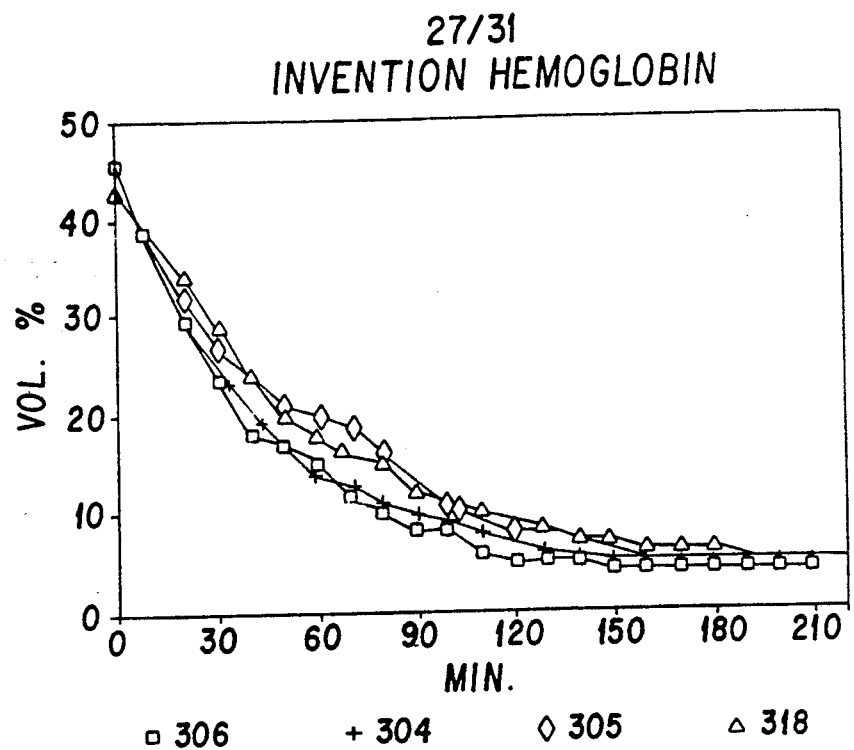
FIG. 20 is a graphic representation of data collected from Example X. In both FIGS. 20(A) and 20(B), the ordinate represents hematocrit percent to blood volume while the abscissa represents time in minutes. Both the test and control groups showed a similar decrease in hematocrit during the exchange transfusion.
Figure 20B:
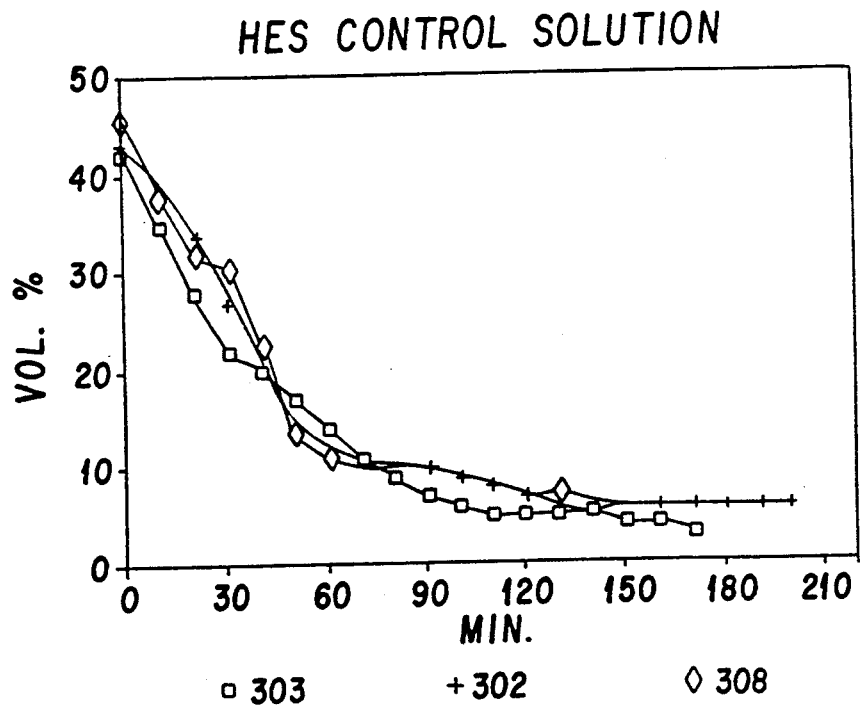
Figure 21A:
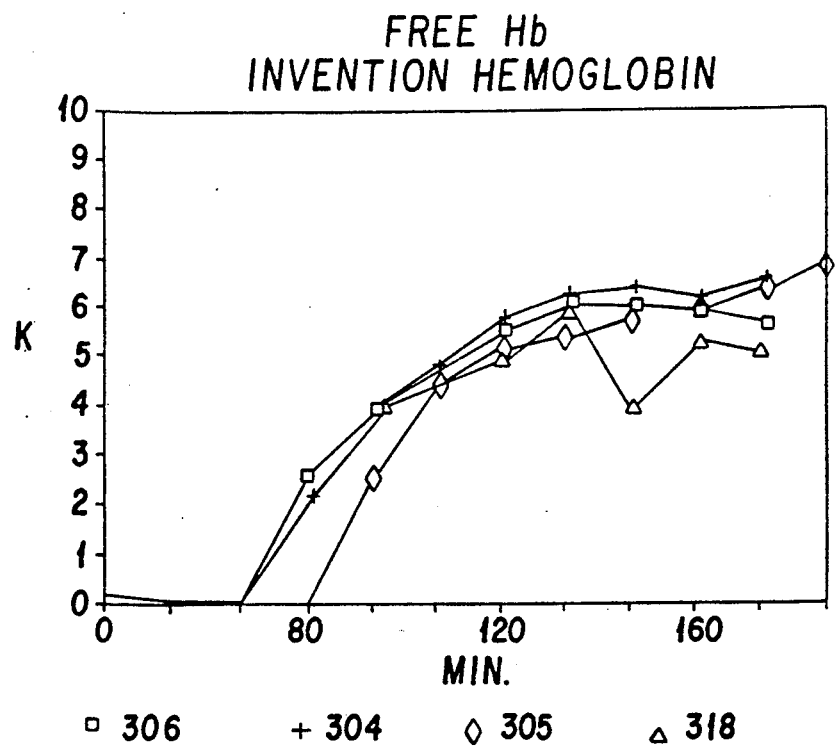
Figure 21B:
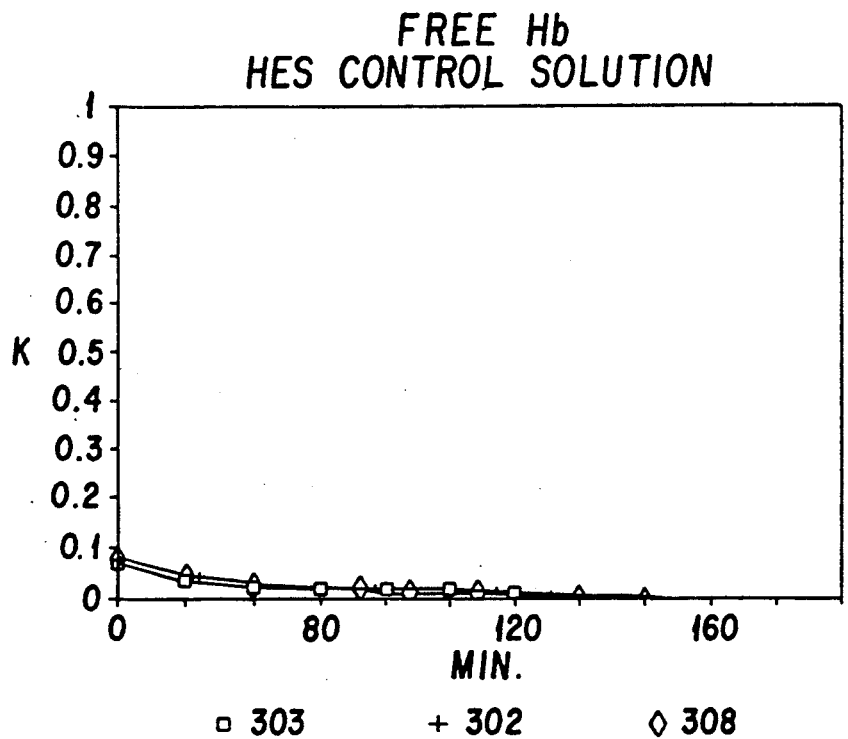
FIG. 21(B) is data collected from three control dogs transfused with hydroxyethyl starch solution (HES). The test group shows a progressive increase in plasma (free) hemoglobin to approximately 6 percent during exchange, in contrast to the control group. The ordinate represents the grams per 100 ml. of blood volume.
Figure 22:
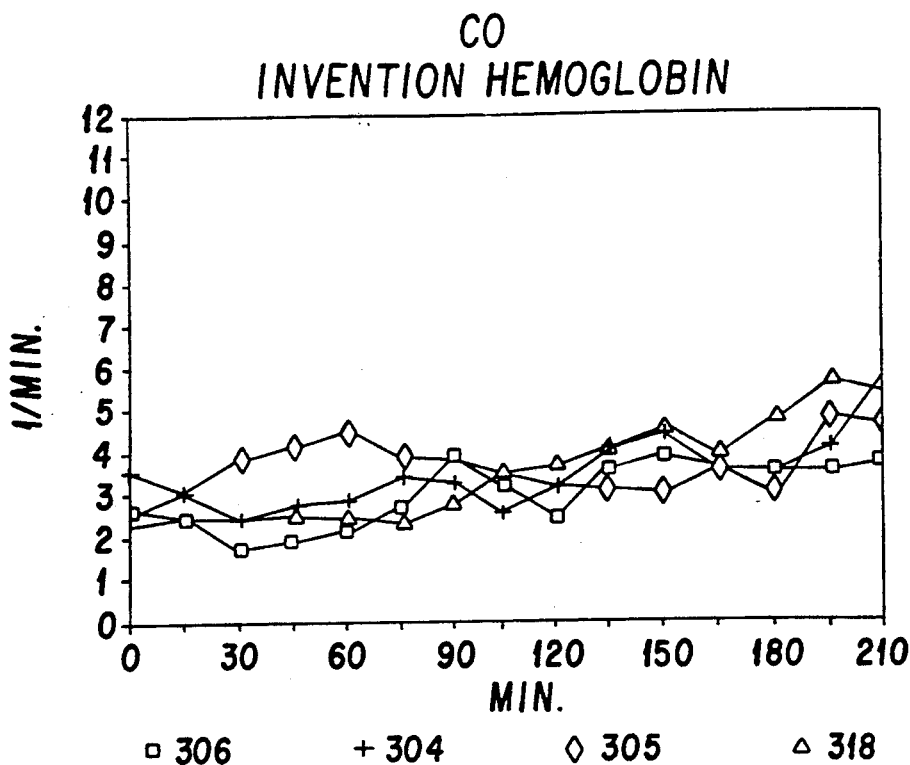
FIG. 22 is a graphic representation of data collected from Example X. Comparison of four test dogs (upper figure) and three control dogs (lower figure) demonstrates that the test animals receiving Invention Hemoglobin maintained stable cardiac outputs in contrast to the control group which showed increasing cardiac outputs associated with declining hematocrit and arterial oxygen content.
Figure 22:
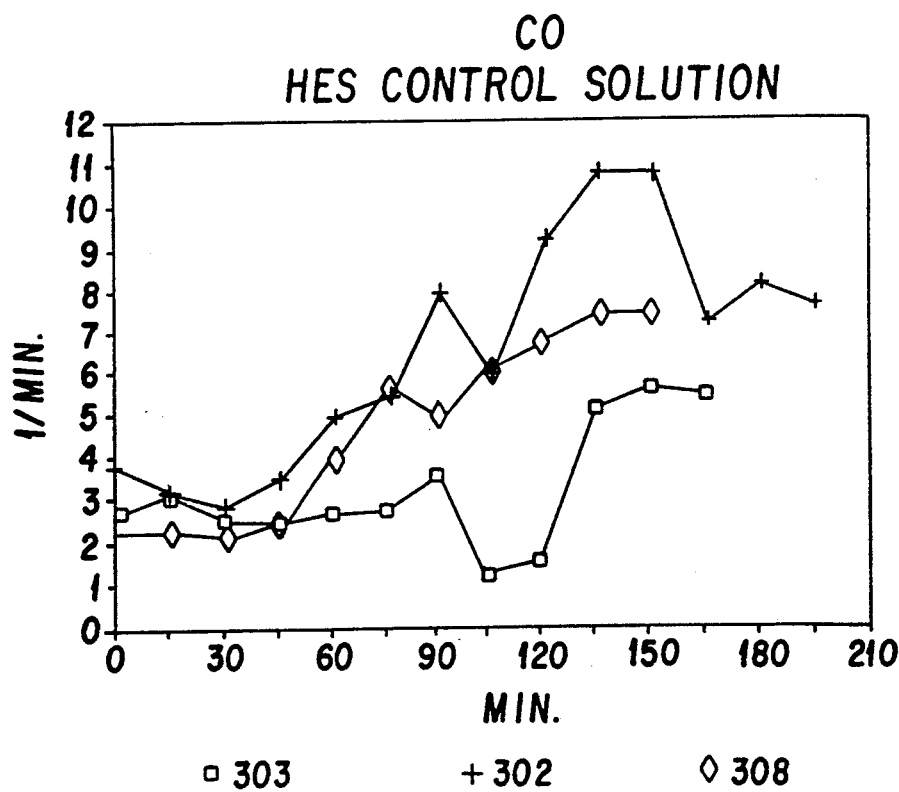
Figure 23A:
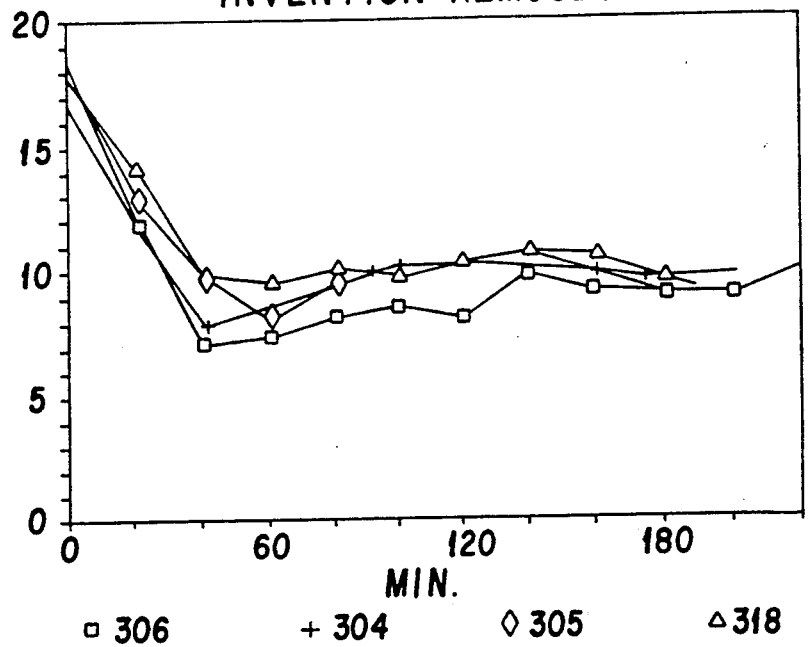
FIG. 23 represents a graphic representation of data collected during the performance of Example X. A comparison of four test dogs (23A figure) and three control dogs (23B figure) shows reduced but adequate and well-maintained arterial oxygen content during the exchange in the test group in contrast to the control group, which had progressive decline in oxygen content associated with the decreasing hematocrit.
Figure 23B:
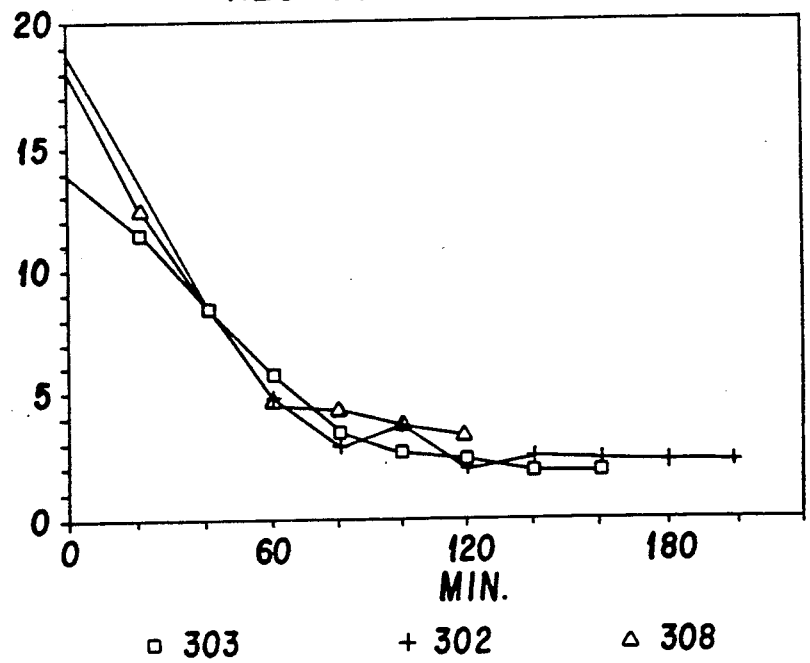
Figure 24A:
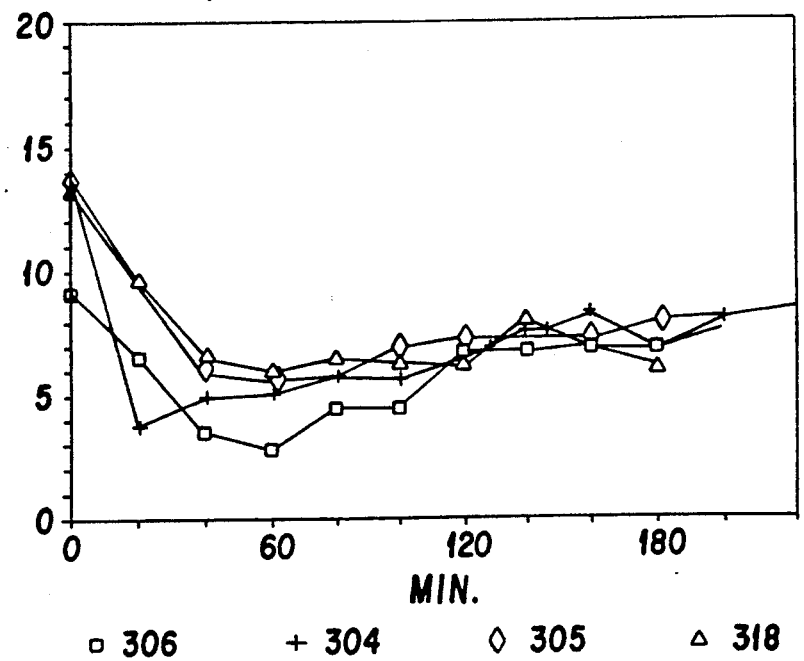
FIG. 24 represents a graphic comparison of four test dogs (24A figure) and three control dogs (24B figure). The ordinate in FIG. 23 represents venous oxygen content while the abscissa represents time in minutes. The test group shows reduced but adequate and well-maintained venous oxygen contents during the exchange in contrast to the control group which had progressive decline in oxygen content associated with the decreasing hematocrit.
Figure 24B:
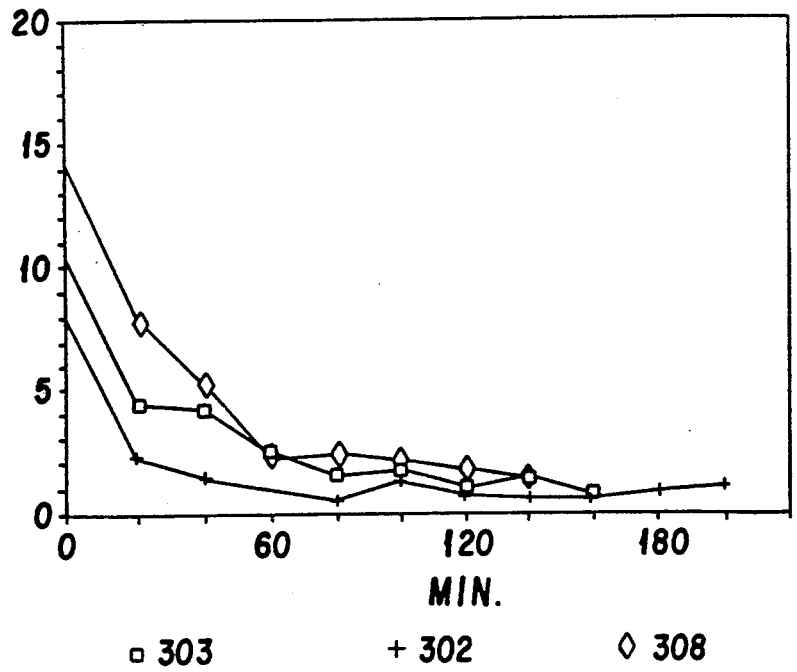

The association of oxygen delivery with the infused bovine hemoglobin is demonstrated in FIG. 19 which clearly shows the departure of the declining oxygen delivery which is at first associated with the declining hematocrit in the initial exchange and which then increases in association with the increasing concentration of bovine hemoglobin which is used to replace the sheep red blood cells during the exchange.

CONCLUSIONS

This study clearly demonstrates the efficacy of Invention Hemoglobin as an oxygen transport solution. The blood gas data and hemodynamic data are consistent with the survivability of the test animals in contrast to the control animals, none of which survived the acute exchange transfusion. Since the residual hematocrits in all of the test animals were less than 5% and, in some cases, between 1 and 2%, study clearly demonstrates Invention Hemoglobin contributed significantly to adequate oxygen transport in the test animals. Furthermore, all of the test animals survived on a long-term basis without intensive care or increased inspired oxygen.

| | | | | | | | | Ven | VEN |
|---|---|---|---|---|---|---|---|---|---|
| SHEEP | WTIKES | HCT | ART POB | VEN POB | PCOB | PH | OR CONTENT | KOR CON BASELINE | OR CONENT | HO2COM BASELINE |

Blood Gas Analysis - 7 Test Animals
EXCHANGE TRANSFUSION: OXYGEN MICE
ORIGINAL DATA

| SHEEP | WTIKES | HCT | ART POB | VEN POB | PCOB | PH | OR CONTENT | KOR CON BASELINE | Ven OR CONENT | VEN HO2COM BASELINE |
|---|---|---|---|---|---|---|---|---|---|---|
| GREEN | 25.00 | 31.00 | 62.30 | 48.00 | 37.29 | 7.47 | 12.00 | 100.00 | 8.35 | 100.00 |
| 198 | 25.00 | 18.00 | 78.30 | 25.10 | 38.90 | 7.44 | 7.45 | 50.50 | 1.55 | 18.50 |
| Feb 24 | 85.10 | 17.00 | 54.50 | 19.30 | 44.10 | 7.33 | 7.55 | 58.98 | 2.00 | 33.50 |
| hemopure | 25.00 | 16.00 | 65.70 | 80.70 | 25.20 | 7.54 | 7.85 | 56.00 | 1.00 | 16.77 |
| hemopure | 85.00 | 11.00 | 57.89 | 14.30 | 34.40 | 7.43 | 7.90 | 61.70 | 2.10 | 85.15 |
| hemopure | 25.00 | 4.50 | 70.90 | 17.00 | 38.00 | 7.52 | 8.30 | 64.84 | 3.95 | 47.21 |
| BLUE250 | 23.00 | 25.00 | 87.50 | 36.00 | 34.34 | 7.45 | 9.60 | 100.00 | 6.45 | 100.00 |
| Mar 9 | 23.00 | 15.00 | 100.00 | 30.90 | 31.64 | 7.43 | 6.75 | 70.51 | 8.90 | 64.96 |
| hemopure | 23.00 | 13.00 | 79.30 | 16.90 | 89.00 | 7.48 | 5.45 | 56.66 | 6.75 | 11.63 |
| hemopure | 23.00 | 1.60 | 95.70 | 6.70 | 88.76 | 7.30 | 6.90 | 71.00 | 1.30 | 20.16 |
| BLUE250 | 83.00 | 20.00 | 95.20 | 45.20 | 38.90 | 7.50 | 9.95 | 100.00 | 7.85 | 100.00 |
| May 12 | 23.00 | 16.00 | 95.30 | 38.60 | 38.60 | 7.44 | 9.70 | 97.49 | 8.90 | 40.00 |
| hemopure | 23.00 | 3.00 | 86.30 | 19.60 | 27.20 | 7.50 | 7.85 | 78.06 | 3.50 | 40.20 |
| BLUE598 | 87.30 | 25.00 | 90.90 | 48.50 | 31.70 | 7.69 | 9.95 | 100.00 | 6.10 | 100.00 |
| Aug 11 | 27.30 | 81.00 | 97.50 | 27.00 | 30.03 | 7.51 | 8.05 | 88.94 | 6.70 | 77.05 |
| | 87.30 | 13.00 | 85.70 | 31.40 | 36.30 | 7.45 | 6.30 | 63.32 | 1.05 | 30.33 |
| hemopure | 87.30 | 10.00 | 62.60 | 24.34 | 34.30 | 7.40 | 7.60 | 76.30 | 8.30 | 37.70 |
| hemopure | 87.30 | 4.50 | 70.00 | 19.70 | 38.90 | 7.46 | 7.89 | 78.36 | 8.50 | 40.90 |
| centblood | 87.30 | 3.50 | 61.00 | 18.79 | 23.30 | 7.51 | 6.20 | 62.31 | 2.00 | 32.79 |
| centblood | 87.30 | 8.30 | 83.00 | 13.90 | 38.40 | 7.46 | 6.09 | 60.30 | 1.75 | 20.69 |
| YELL699 | 90.00 | 20.00 | 87.00 | 47.00 | 26.90 | 7.44 | 11.25 | 100.00 | 9.30 | 100.00 |
| Sept 10 | | 19.00 | 90.00 | 30.30 | 25.00 | 7.43 | 7.25 | 64.64 | 4.55 | 48.98 |
| hemopure | | 12.00 | 96.00 | 89.00 | 25.00 | 7.29 | 6.85 | 60.09 | 8.45 | 26.34 |
| hemopure | | 7.00 | 86.00 | 25.10 | 36.50 | 7.37 | 6.65 | 59.11 | 2.70 | 29.03 |
| hemopure | | 8.09 | 95.34 | 26.30 | 29.94 | 7.43 | 7.25 | 64.44 | 3.40 | 36.54 |
| centblood | | 4.00 | 95.20 | 83.40 | 31.60 | 7.40 | 5.70 | 50.67 | 8.05 | 22.04 |
| centblood | | 8.00 | 95.30 | 16.00 | 38.70 | 7.41 | 2.60 | 24.89 | 1.25 | 13.44 |
| hemopure | | 1.50 | 95.30 | 20.70 | 23.00 | 7.43 | 3.90 | 24.67 | 1.75 | 19.00 |
| BLUE590 | 25.00 | 20.00 | 25.10 | 46.10 | 26.50 | 7.44 | 10.55 | 100.00 | 6.80 | 100.00 |
| Sept 11 | | 80.00 | 62.60 | 46.10 | 36.60 | 7.47 | 7.05 | 66.02 | 3.30 | 48.52 |
| hemopure | | 11.00 | 86.10 | 22.10 | 25.90 | 7.40 | 7.10 | 67.30 | 1.55 | 22.79 |
| hemopure | | 6.00 | 86.00 | 83.09 | 21.00 | 7.48 | 7.50 | 71.09 | 3.15 | 66.38 |
| hemopure | | 8.50 | 27.10 | 81.40 | 31.00 | 7.46 | 8.75 | 66.82 | 3.10 | 45.59 |
| BLUE209 | 34.50 | 20.00 | 92.60 | 47.00 | 38.00 | 7.60 | 18.65 | 100.00 | 9.05 | 100.00 |
| Sept 14 | | 18.00 | 89.00 | 36.10 | 33.00 | 7.44 | 8.19 | 64.3 | 3.50 | 43.90 |
| hemopure | | 8.00 | 147.90 | 89.00 | 15.60 | 7.59 | 8.90 | 64.57 | 8.10 | 38.34 |
| hemopure | | 3.56 | 82.00 | 83.00 | 27.50 | 7.40 | 9.95 | 70.75 | 4.05 | 60.35 |
| hemopure | | 3.00 | 81.50 | 83.64 | 77.00 | 9.00 | 9.45 | 77.00 | 9.73 | 71.43 |

| SHEEP | PLASMA HGP | CARDIAC OUTPUT | nC.O. BASELINE | OR DEL | HOW DEL BASELINE | AVOR | O2 CONTURE | O2 COM BASELINE | EXT FRACT |
|---|---|---|---|---|---|---|---|---|---|
| GREEN | DATA | 6.38 | 100.00 | 30.30 | 10.00 | 4.48 | 11.25 | 100.00 | 31.90 |
| 198 | NOT | 6.10 | 97.15 | 17.61 | 55.00 | 5.90 | 11.32 | 124.00 | 36.00 |
| Feb 24 | TAKEN | 6.15 | 65.60 | 18.50 | 3.73 | 4.75 | 7.00 | | |
| hemopure | | 3.50 | 55.26 | 10.15 | 31.37 | 5.05 | 8.19 | 72.00 | |
| hemopure | | 4.69 | 74.1 | 14.02 | | | | | |
| hemopure | 4.01 | 78.24 | 15.31 | 47.30 | 4.35 | 8.02 | 71.30 | 52.51 | |
| BLUE250 | DATA | 5.61 | 100.00 | 23.42 | 100.00 | 3.15 | 7.60 | 100.00 | 28.81 |
| Mar 9 | NOT | 4.40 | 115.51 | 19.00 | 61.81 | 3.05 | 10.05 | 141.20 | 57.03 |
| hemopure | TAKEN | 8.90 | 39.22 | 5.31 | 22.25 | 6.70 | 4.50 | 50.50 | 86.29 |
| hemopure | | 3.04 | 27.75 | 9.78 | 41.50 | 9.60 | 7.00 | 102.72 | 81.16 |
| BLUE250 | DATE | 4.40 | 100.00 | 19.05 | 100.00 | 2.70 | 5.17 | 100.00 | 27.11 |
| May 12 | NOT | 4.22 | 95.91 | 17.81 | 93.69 | 6.00 | 18.48 | 241.29 | 70.05 |
| hemopure | TAKEN | 3.75 | 85.83 | 11.01 | 61.99 | 3.75 | 6.11 | 110.10 | 51.77 |
| BLUE598 | 0.00 | 5.57 | 100.00 | 20.30 | 100.00 | 3.05 | 7.04 | 100.00 | 38.75 |
| Aug 11 | 0.00 | 5.09 | 91.26 | 16.50 | 81.20 | 4.15 | 7.76 | 98.67 | 48.91 |
| | 0.00 | 6.06 | 100.00 | 14.00 | 60.97 | 4.45 | 9.08 | 125.70 | 70.57 |
| hemopure | 1.72 | 6.64 | 83.30 | 18.90 | 63.55 | 5.30 | 9.61 | 114.63 | 69.84 |
| hemopure | 5.22 | 3.10 | 55.64 | 8.10 | 44.30 | 4.70 | 5.34 | 67.94 | 65.28 |
| centblood | 3.04 | 3.44 | 61.96 | 7.81 | 30.47 | 4.00 | 5.29 | 67.30 | 67.73 |
| centblood | 4.00 | 6.03 | 86.91 | 10.68 | 52.38 | 4.25 | 7.52 | 95.67 | 70.81 |
| YELL699 | 0.00 | 6.02 | 100.00 | 82.39 | 100.00 | 1.93 | 4.05 | 100.00 | 17.31 |
| Sept 10 | 0.00 | 5.54 | 91.87 | 13.05 | 59.21 | 8.70 | 5.12 | 126.62 | 34.97 |
| hemopure | 8110.00 | 3.04 | 63.02 | 8.98 | 20.39 | 4.60 | 5.76 | 162.22 | 64.16 |
| hemopure | 2600.00 | 3.03 | 63.52 | 8.70 | 27.54 | 2.95 | 5.22 | 100.09 | 59.45 |
| hemopure | 4500.00 | 4.29 | 71.16 | 10.78 | 45.03 | 3.05 | 5.70 | 100.74 | 53.17 |
| centblood | 3600.00 | 3.91 | 64.04 | 7.69 | 22.09 | 3.63 | 4.98 | 121.68 | 63.98 |
| centblood | 2340.00 | 3.89 | 64.31 | 3.76 | 16.00 | 1.55 | 2.00 | 51.36 | 55.28 |
| hemopure | 4220.00 | 4.77 | 79.01 | 6.41 | 87.40 | 2.15 | 2.54 | 87.61 | 55.22 |
| BLUE590 | 0.00 | 3.68 | 100.00 | 13.64 | 100.00 | 3.95 | 4.05 | 100.00 | 25.50 |
| Sept 11 | 0.00 | 4.13 | 114.00 | | | | | | |
| hemopure | 3000.00 | 8.08 | 77.00 | 7.15 | 52.68 | 5.58 | 5.59 | 115.26 | 78.10 |
| hemopure | 4960.00 | 4.14 | 114.30 | 11.00 | 61.30 | 4.35 | 6.43 | 128.50 | |
| hemopure | 6304.00 | 3.18 | 87.05 | | | | | | |
| BLUE209 | 0.00 | | | | | | | | |

-continued

| Blood Gas Analysis - 7 Test Animals |
|---|
| EXCHANGE TRANSFUSION: OXYGEN MICE ORIGINAL DATA |

| | |
|---|---|
| Sept 14 hemopure | 0.00 |
| hemopure | |
| hemopure | 7652.00 |

| BLOOD GAS ANALYSIS - 6 Control Animals | | | | | | | | | | | |
|---|---|---|---|---|---|---|---|---|---|---|---|
| | | | ART PO2 | VEN PO2 | PCO2 | PH | O2 CONTENT | HO2 COM BASELINE | O2 CONTENT | HO3 BASELINE | PLASMA HGD |
| 55 | 22.30 | 16.00 | 89.60 | 34.80 | 36.50 | 7.49 | 6.30 | 100.00 | 2.70 | 100.00 | |
| HESPAN | | 9.00 | 90.70 | 26.50 | 33.70 | 7.43 | 3.65 | 57.94 | 9.60 | 22.22 | |
| CONTROL | | 7.50 | 96.40 | 23.40 | 32.20 | 7.46 | 3.15 | 50.00 | 9.60 | 14.81 | |
| | | 6.50 | 121.60 | 17.20 | 27.10 | 7.43 | 1.90 | 30.16 | 0.20 | 7.41 | |
| | | 4.00 | 129.00 | 10.10 | 19.30 | 7.41 | 1.65 | 26.19 | 0.20 | 7.41 | |
| 56 | 21.40 | 19.00 | 90.00 | 37.10 | 40.70 | 7.43 | 8.25 | 100.00 | 3.40 | 100.00 | |
| HESPAN | | 14.00 | 87.70 | 31.20 | 36.90 | 7.46 | 5.85 | 70.91 | 2.00 | 50.02 | |
| CONTROL | | 10.00 | 89.00 | 25.00 | 32.40 | 7.49 | 4.35 | 52.73 | 6.05 | 25.00 | |
| | | 7.50 | 96.80 | 24.10 | 32.20 | 7.49 | 3.45 | 41.02 | 0.40 | 11.74 | |
| | | 6.50 | 108.90 | 20.10 | 32.90 | 7.45 | 2.70 | 32.73 | 0.20 | 5.88 | |
| | | 5.50 | 110.10 | 17.70 | 32.30 | 7.42 | 2.35 | 28.48 | 0.15 | 4.41 | |
| | | 5.00 | 115.00 | 15.90 | 27.00 | 7.38 | 2.15 | 26.06 | 0.15 | 4.41 | |
| 57 | 20.00 | 23.00 | 91.10 | 29.40 | 29.20 | 7.44 | 9.60 | 100.00 | 5.40 | 100.00 | |
| HESPAN | | 17.00 | 71.00 | 31.50 | 36.70 | 7.47 | 7.00 | 72.92 | 2.50 | 46.30 | |
| CONTROL | | 13.00 | 99.00 | 31.70 | 20.00 | 7.51 | 5.80 | 60.42 | 2.00 | 37.04 | |
| | | 9.00 | 91.00 | 23.60 | 34.00 | 7.45 | 3.95 | 41.15 | 0.85 | 15.74 | |
| | | 7.00 | 101.20 | 22.20 | 32.20 | 7.47 | 2.75 | 28.65 | 0.40 | 7.41 | |
| | | 6.00 | 106.30 | 17.90 | 30.70 | 7.48 | 2.50 | 26.04 | 0.25 | 4.63 | |
| | | 5.00 | 115.70 | 18.00 | 25.20 | 7.48 | 2.25 | 23.44 | 0.20 | 3.70 | |
| 58 | 10.20 | 15.00 | 90.90 | 35.00 | 37.70 | 7.48 | 6.90 | 100.00 | 3.35 | 100.00 | |
| HESPAN | | 12.00 | 89.60 | 29.00 | 35.80 | 7.47 | 5.45 | 81.00 | 1.05 | 55.22 | |
| CONTROL | | 8.50 | 94.20 | 24.00 | 34.00 | 7.46 | 3.70 | 53.62 | 1.15 | 34.33 | |
| | | 7.00 | 99.80 | 20.00 | 33.00 | 7.44 | 3.30 | 47.83 | 0.85 | 22.39 | |
| | | 5.00 | 109.60 | 19.40 | 27.00 | 7.47 | 3.05 | 44.20 | 0.30 | 0.96 | |
| | | 4.50 | 120.00 | 20.00 | 23.90 | 7.44 | 2.75 | 39.06 | 0.25 | 7.44 | |
| 89 | 19.00 | 17.00 | 86.00 | 34.90 | 39.60 | 7.44 | 7.85 | 100.00 | 3.40 | 100.00 | |
| HESPAN | | 12.00 | 103.10 | 36.20 | 30.30 | 7.53 | 6.10 | 77.71 | 2.75 | 80.88 | |
| CONTROL | | 10.00 | 96.00 | 92.50 | 33.30 | 7.47 | 4.45 | 56.69 | 1.30 | 38.24 | |
| | | 7.00 | 89.90 | 24.40 | 34.80 | 7.45 | 3.20 | 40.74 | 0.90 | 26.47 | |
| | | 5.50 | 99.90 | 18.30 | 34.80 | 7.45 | 2.55 | 32.48 | 0.40 | 11.74 | |
| 510 | 21.00 | 22.00 | 75.60 | 43.20 | 36.30 | 7.49 | 8.90 | 100.00 | 4.75 | 100.00 | |
| HESPAN | | 20.00 | 74.90 | 37.40 | 31.00 | 7.49 | 7.95 | 89.33 | 4.30 | 90.53 | |
| CONTROL | | 11.00 | 101.50 | 31.60 | 29.60 | 7.53 | 5.35 | 60.11 | 2.10 | 44.21 | |
| | | 8.50 | 100.00 | 24.20 | 25.50 | 7.49 | 3.90 | 43.82 | 0.90 | 18.95 | |
| | | 7.00 | 103.60 | 18.90 | 27.00 | 7.49 | 3.65 | 41.01 | 0.65 | 13.68 | |
| | | 5.00 | 116.50 | 17.00 | 21.10 | 7.45 | 2.85 | 32.02 | 0.80 | 16.84 | |

| | CARDIAC OUTPUT | nC.C. BASELINE | C2 DEL | HO2 DEL BASELINE | AVCOR | O2 CONTURE | BASELINE | EXT FRACT |
|---|---|---|---|---|---|---|---|---|
| 55 | 5.62 | 100.00 | 15.90 | 100.00 | 2.00 | 9.10 | 100.00 | 57.80 |
| HESPAN | 7.08 | 125.98 | 11.60 | 72.96 | 3.06 | 9.70 | 106.59 | 83.60 |
| CONTROL | 6.51 | 115.64 | 9.20 | 57.86 | 2.75 | 8.00 | 87.91 | |
| | 4.74 | 84.34 | 4.60 | 25.16 | 1.70 | 3.60 | | |
| | 3.01 | 53.50 | 2.20 | 13.84 | 1.45 | 2.00 | 21.98 | 90.90 |
| 56 | 5.77 | 100.00 | 22.24 | 100.00 | 4.05 | 13.00 | 100.00 | 58.00 |
| HESPAN | 5.78 | 100.17 | 15.00 | 71.04 | 3.05 | 10.40 | 79.51 | 65.80 |
| CONTROL | 6.06 | 105.03 | 12.32 | 25.60 | 3.50 | 9.91 | 75.76 | 80.40 |
| | 6.02 | 104.32 | 9.70 | 43.62 | 3.05 | 0.50 | 65.60 | 88.50 |
| | 5.45 | 94.45 | 4.00 | 30.94 | 2.50 | 6.37 | 48.70 | 92.60 |
| | 4.82 | 83.54 | 5.29 | 23.79 | 2.20 | 4.96 | 37.92 | 93.80 |
| | 2.76 | 47.83 | 2.77 | 12.46 | 2.00 | 2.50 | 19.78 | 93.10 |
| 57 | 4.50 | 100.00 | 21.60 | 100.00 | 4.20 | 9.45 | 100.00 | 43.00 |
| HESPAN | 4.83 | 107.33 | 16.90 | 78.24 | 4.50 | 10.07 | 115.03 | 64.60 |
| CONTROL | 5.59 | 124.22 | 16.20 | 75.00 | 3.00 | 10.62 | 112.30 | 65.60 |
| | 6.19 | 137.54 | 12.20 | 56.48 | 3.10 | 9.59 | 101.48 | 79.60 |
| | 6.91 | 153.54 | 9.50 | 43.90 | 5.25 | 0.18 | 85.93 | 85.50 |
| | 5.98 | 131.54 | 7.60 | 34.26 | 2.25 | 6.66 | 70.48 | 90.00 |
| | 6.01 | 151.33 | 7.66 | 35.46 | 2.05 | 6.98 | 73.04 | 91.10 |
| 58 | 5.71 | 100.00 | 21.60 | 100.00 | 3.85 | 11.10 | 100.00 | 51.60 |
| HESPAN | 4.07 | 106.30 | 10.04 | 87.22 | 3.80 | 12.67 | 14.14 | 47.30 |
| CONTROL | 7.31 | 128.02 | 14.86 | 68.80 | 2.55 | 10.24 | 92.25 | 68.90 |
| | 7.64 | 133.00 | 13.95 | 64.18 | 2.53 | 10.70 | 96.40 | 77.30 |
| | 4.92 | 121.02 | 11.58 | 53.61 | 2.75 | 10.44 | 94.05 | 90.20 |
| | 4.18 | 73.20 | 6.38 | 29.26 | 2.50 | 3.74 | 51.71 | 90.90 |
| 89 | 5.17 | 100.00 | 21.36 | 100.00 | 4.45 | 12.11 | 100.00 | 56.69 |
| HESPAN | 7.04 | 134.17 | 22.60 | 105.01 | 3.35 | 12.41 | 94.12 | 54.92 |
| CONTROL | 5.07 | 113.54 | 13.75 | 64.37 | 3.15 | 9.783 | 93.27 | 70.78 |

| | | -continued | | | | | | |
|---|---|---|---|---|---|---|---|---|
| | | BLOOD GAS ANALYSIS - 6 Control Animals | | | | | | |
| | 6.51 | 125.92 | 10.96 | 51.31 | 3.01 | 10.31 | 87.39 | 94.10 |
| | 5.04 | 112.96 | 7.04 | 36.70 | 2.15 | 6.61 | 70.43 | 94.29 |
| 510 | 5.54 | 100.00 | 22.62 | 100.00 | 4.15 | 10.55 | 100.00 | 44.62 |
| HESPAN | 5.93 | 107.04 | 21.63 | 95.63 | 3.65 | 9.93 | 94.12 | 45.90 |
| CONTROL | 6.60 | 119.13 | 16.20 | 71.62 | 3.25 | 9.84 | 93.27 | 60.74 |
| | 6.70 | 120.94 | 11.99 | 53.01 | 3.00 | 9.22 | 87.39 | 76.90 |
| | 5.40 | 97.47 | 9.04 | 39.96 | 3.00 | 7.43 | 70.43 | 82.20 |
| | 6.92 | 124.91 | 9.05 | 40.01 | 2.05 | 6.51 | 61.71 | 71.96 |

EXAMPLE X

DOG EXPERIMENTS

OBJECTIVE

Invention Hemoglobin was tested for efficacy, tolerability, and side effects on beagle dogs. The experimental arrangement was intended to answer the question of whether the preparation studied was able to assume the oxygen transport function and the volume replacement in case of severe losses of endogenous blood, and how rapidly the hemoglobin supplied is excreted from the body. The tolerability and the occurrence of unexpected side effects was also determined secondarily.

There is an indication for an $O_2$ transportation solution only when the remaining amount of endogenous hemoglobin is no longer able to satisfy the $O_{02}$ requirement of the tissue. From this it follows that the anemia of the experimental animals must be so severe that at least detectable injuries occur from the $O_2$ deficiency, and at the same time, the administration of the hemoglobin solution demonstrably prevents these injuries.

TEST SUBSTANCE

Invention Hemoglobin solution as described above and as produced by the process of Example I.

EXPERIMENTAL MODEL 7 purebred beagle dogs were used for study who had been splenectomized approximately 3 weeks before the beginning of the study.

INSTRUMENTATION

After premedication and the initiation of anesthesia, an isovolemic hemodilution was carried out through peristaltic pumps in controlled manner on 4 animals with invention Hemoglobin solution up to a residual hematocrit of 5%, and on 3 control animals with a hydroxyethyl starch solution (HES) whose ionic composition and colloid osmotic pressure were equivalent to those of the Invention Hemoglobin solution. A number of parameters were determined during the exchange transfusion and the follow-up period of 10 days.

DOG TEST RESULTS

In this study, 4 test dogs received exchange transfusion with Invention Hemoglobin under general anesthesia over a 3-hour period with measurements approximately every 10 minutes. All test dogs survived the acute exchange transfusion with residual hematocrits below 5%. The hemodynamic and blood gas analysis revealed that all test dogs were well oxygenated at the end of the procedure in contrast to the 3 control dogs which did not survive the exchange transfusion with the hydroxyethyl starch solution. The 3 control dogs had evidence of inadequate oxygenation associated with the decreasing hematocrit levels. FIGS. 20-24 demonstrate the differences in the test and control groups for selected parameters measured.

CONCLUSION

The preliminary results of this efficacy study demonstrate that Invention Hemoglobin solution contributes to normal oxygenation of test dogs which are severely depleted of red blood cell mass. In contrast to the control dogs which could not survive with very low residual hematocrit levels, the test animals all survived the acute exchange transfusion. The conclusion of this study is that it is evident that Invention Hemoglobin solution transports oxygen under extreme conditions of severe red blood cell loss.

Having now fully described the invention, it will be readily apparent to one skilled in the art that many changes and modifications may be made thereto without departing from the spirit or scope thereof.

We claim:

1. A hemoglobin solution for transporting and releasing oxygen to living cells, comprising bovine hemoglobin in an aqueous pharmaceutically-acceptable carrier medium, said hemoglobin solution being substantially free of red blood cell stroma and having an endotoxin level of less than about 0.5 endotoxin units per milliliter (EU/ml) determined by a chromogenic Limulus Amebocytic Lysate (LAL) assay against an end-point reaction made by a series of dilutions of a reference endotoxin solution and thereafter interpolating from a standary regression curve made from colormetric readings from said dilutions.

2. A hemoglobin solution of claim 1 wherein said hemoglobin is intermolecularly and intramolecularly crosslinked to provide polyhemoglobin with at least about 50% of said polyhemoglobin of greater than tetrameric form.

3. A blood-substitute comprising the hemoglobin solution of claim 2.

4. A plasma-expander comprising the hemoglobin solution of claim 2.

5. A resuscitation fluid comprising the hemoglobin solution of claim 2.

6. A blood-substitute comprising intramolecularly and intramolecularly crosslinked bovine hemoglobin in an aqueous pharmaceutically acceptable carrier medium, said hemoglobin being crosslinked to a sufficient degree to provide polyhemoglobin with at least about 50% of said polyhemoglobin of greater than tetrameric form, said blood-substitute being substantially free of cell stroma, non-hemoglobin proteins and pyrogens and having an endotoxin level of less than about 0.5 endotoxin units per milliliter (EU/ml) determined by a chromogenic Limulus Amebocytic Lysate (LAL) assay against an end-point reaction made by a series of dilutions of a reference endotoxin solution and thereafter interpolating from a standard regression curve made from colormetric readings from said dilutions.

7. A blood-substitute comprising an aqueous solution of hemoglobin derived from bovine red blood cells, said hemoglobin being crosslinked to a sufficient degree to provide polyhemoglobin with at least about 50% of said polyhemoglobin of greater than tetrameric form, said blood-substitute:
   a) having a $P_{50}$ measured under human physiologic conditions in the range of from about 18 to about 36 mmHg;
   b) being substantially free of red blood cell stroma and non-hemoglobin proteins; and
   c) having an endotoxin level of less than about 0.5 endotoxin units per milliliter (EU/ml) determined by a chromogenic Limulus Amebocytic Lysate (LAL) assay against an end-point reaction made by a series of dilutions of a reference endotoxin solution and thereafter interpolating from a standard regression curve made from colorometric readings from said dilutions.

8. A blood-substitute of claim 7 having an endotoxin level of less than about 0.02 EU/ml.

9. A blood-substitute comprising an aqueous solution of crosslinked hemoglobin, said hemoglobin being derived from bovine red blood cells, said blood-substitute characterized by:
   a) an endotoxin concentration of less than about 0.02 endotoxin units per milliliter (EU/ml) determined by a chromogenic Limulus Amebocytic Lysate (LAL) assay against an end-point reaction made by a series of dilutions of a reference endotoxin solution and thereafter interpolating from a standard regression curve made from colorometric readings from said dilutions;
   b) a phospholipid concentration of less than about 1 nanogram per milliliter;
   c) a hemoglobin molecular weight distribution of greater than about 90% in the range of 68,000–500,000 daltons;
   d) an osmolarity as measured by freezing point depression in the range of 180–320 millimoles per liter;
   e) a hemoglobin content of from about 5 to about 25 grams per deciliter;
   f) a methemoglobin content of less than about 20%, by weight;
   g) a $P_{50}$ in the range of about 18–36 mm Hg;
   h) an intravascular half-life of at least about four days;
   i) being substantially free of red blood cell stroma, non-hemoglobin proteins and pyrogen.

10. A mammalian blood-substitute comprising crosslinked hemoglobin suspended in an aqueous medium, said hemoglobin having been derived from mammalian blood cells, said blood-substitute having: crosslinked hemoglobin having a molecular weight distribution of greater than about 90% in the range of about 68,000 to 500,000 daltons; an osmolarity as measured by freezing point depression in the range of about 180–230 milliosmoles per liter of solution; a final hemoglobin content of from about 9 to about 13 grams per deciliter; a methamoglobin content of less than about 10%, by weight; physiologic levels of sodium chloride and potassium chloride; less than about one nanomole of phospholipid per milliliter; less than about one part per million of crosslinking agent; a $P_{50}$ in the range of about 18–36 mm Hg; an intravascular half-life of at least about four days; and an endotoxin level of less than about 0.5 endotoxin units per milliliter (EU/ml) determined by a chromogenic Limulus Amebocytic Lysate (LAL) assay against an end-point reaction made by a series of dilutions of a reference endotoxin solution and thereafter interpolating from a standard regression curve made from colorometric readings from said dilutions.

11. A blood-substitute of claim 9 further characterized by the fact that, in vivo, it:
   a) does not activate complement;
   b) does not cause hemorrhagic disorders;
   c) does not cause abnormal platelet function or aggregation;
   d) does not cause abnormal prothrombin times (PT);
   e) does not cause abnormal partial thromboplastic times;
   f) does not interfere with blood typing or cross-matching;
   g) is non-toxic to the kidneys of normal healthy mammals at concentrations of 3.5 grams per kilogram body weight and 8 grams per deciliter circulating blood volume;
   h) exhibits circulating persistence of at least seven days; and
   i) acts as a stimulus to accelerated erythropoiesis.

12. A method for producing a hemoglobin solution substantially free of endotoxins by performing the following sequence of steps under substantially endotoxin free conditions:
   a) disrupting the red blood cell fraction of bovine blood without prior washing to produce hemoglobin-containing fraction;
   b) clarifying said hemoglobin-containing solution to produce a substantially stromal-free hemoglobin-containing solution;
   c) microporously filtering said substantially stromal-free hemoglobin-containing solution to produce a partially sterilized, stromal-free, hemoglobin-containing solution;
   d) ultrafiltering said partially sterilized, stromal-free hemoglobin-containing solution to produce a size-separated, partially sterilized, stromal-free, hemoglobin-containing solution; and,
   e) chromatographically treating said size-separated, partially-sterilized, stromal-free, hemoglobin-containing solution in a high performance liquid chromatographic column containing a packing for the ion-exchange affinity separation of endotoxin from hemoglobin under conditions sufficient to produce a substantially phospholipid-free, substantially endotoxin-free hemoglobin solution.

13. A method of claim 12 including the additional steps of crosslinking hemoglobin in said substantially phospholipid-free, substantially endotoxin-free hemoglobin solution to produce a semi-synthetic blood substitute.

14. A hemoglobin solution produced by the method of claim 12.

15. A blood-substitute produced by the method of claim 13.

16. In the preparation of an ultra pure hemoglobin solution involving the steps of isolating hemoglobin from mammalian red blood cells, suspending said isolated hemoglobin in a pharmaceutically acceptable aqueous carrier medium to thereby form a hemoglobin solution, filtering said solution to remove bacteria, red blood cell stroma and phospholipids: the improvement comprising additionally chromatographically treating said hemoglobin solution by passing said solution over a chromatographic medium for the ion-exchange affinity separation of endotoxin under conditions sufficient to produce a hemoglobin solution having an endotoxin level of less than about 0.5 endotoxin units per milliliter (EU/ml) determined by a chromatographic Limulus Amebocytic Lysate (LAL) assay against an end-point reaction made by a series of dilutions of a reference endotoxin solution and thereafter interpolating from a standard regression curve made from colorometric readings from said dilutions.

17. A blood-substitute comprising intermolecularly and intramolecularly crosslinked bovine hemoglobin in an aqueous pharmaceutically acceptable carrier medium, said hemoglobin being crosslinked to a sufficient degree to provide polyhemoglobin with at least about 50% of said polyhemoglobin of greater than tetrameric form, said blood-substitute being substantially free of cell stroma, non-hemoglobin proteins and pyrogens and said blood-substitute being sufficiently purified with respect to endotoxin so that the blood-substitute does not, upon in vivo administration to a mammal in a significant dosage, cause complement activation, wherein the endotoxin level of said composition is less than about 0.5 endotoxin units per milliliter (EU/ml) determined by a chromgenic Limulus Amebocytic Lystate (LAL) assay against an end-point reaction made by a series of dilutions of a reference endotoxin solution and thereafter interpolating from a standard regression curve made from colormetric readings from said dilutions.

18. A blood-substitute of claim 17 wherein said mammal comprises a human being.

19. A blood-substitute of claim 18 having an endotoxin level of less than about 0.02 EU/ml determined by a chromogenic Limulus Amebocytic Lysate (LAL) assay against an end-point reaction made by a series of dilutions of a reference endotoxin solution and thereafter interpolating from a standard regression curve made from colormetric readings from said dilutions.

20. A blood-substitute comprising of from about 5 to about 25 grams of bovine hemoglobin per deciliter of an aqueous pharmaceutically acceptable carrier medium, said hemoglobin being intermolecularly and intramolecularly crosslinked, said blood-substitute being substantially free of cell stroma, non-hemoglobin proteins and pyrogens and said blood-substitute being sufficiently purified with respect to endotoxin so that the blood-substitute does not, upon in vivo administration to a mammal in a significant dosage, cause complement activation, wherein the endotoxin level of said composition is less than about 0.5 endotoxin units per milliliter (EU/ml) determined by a chromogenic Limulus Amebocytic Lystate (LAL) assay against an end-point reaction made by a series of dilutions of a reference endotoxin solution and thereafter interpolating from a standard regression curve made from colormetric readings from said dilutions.

* * * * *